(12) United States Patent
Wesche et al.

(10) Patent No.: US 10,543,271 B2
(45) Date of Patent: Jan. 28, 2020

(54) MESOTHELIN BINDING PROTEINS

(71) Applicant: Harpoon Therapeutics, Inc., South San Francisco, CA (US)

(72) Inventors: Holger Wesche, San Francisco, CA (US); Bryan D. Lemon, Mountain View, CA (US); Richard J. Austin, San Francisco, CA (US); Robert B. Dubridge, Belmont, CA (US)

(73) Assignee: HARPOON THERAPEUTICS, INC., South San Francisco, CA (US)

( * ) Notice: Subject to any disclaimer, the term of this patent is extended or adjusted under 35 U.S.C. 154(b) by 0 days.

(21) Appl. No.: 15/977,968

(22) Filed: May 11, 2018

(65) Prior Publication Data

US 2018/0326060 A1 Nov. 15, 2018

Related U.S. Application Data

(60) Provisional application No. 62/657,417, filed on Apr. 13, 2018, provisional application No. 62/505,719, filed on May 12, 2017.

(51) Int. Cl.
| | | |
|---|---|---|
| *A61K 39/39* | (2006.01) | |
| *A61K 39/395* | (2006.01) | |
| *A61K 39/00* | (2006.01) | |
| *A61P 35/04* | (2006.01) | |

(52) U.S. Cl.
CPC .... *A61K 39/39558* (2013.01); *A61K 39/0011* (2013.01); *A61P 35/04* (2018.01)

(58) Field of Classification Search
None
See application file for complete search history.

(56) References Cited

U.S. PATENT DOCUMENTS

| | | | |
|---|---|---|---|
| 5,061,620 A | 10/1991 | Tsukamoto et al. | |
| 5,759,808 A | 6/1998 | Casterman et al. | |
| 5,773,292 A | 6/1998 | Bander | |
| 5,800,988 A | 9/1998 | Casterman et al. | |
| 5,840,526 A | 11/1998 | Casterman et al. | |
| 5,859,205 A | 1/1999 | Adair et al. | |
| 5,874,541 A | 2/1999 | Casterman et al. | |
| 6,005,079 A | 12/1999 | Casterman et al. | |
| 6,015,695 A | 1/2000 | Casterman et al. | |
| 6,107,090 A | 8/2000 | Bander | |
| 6,136,311 A | 10/2000 | Bander | |
| 6,670,453 B2 | 12/2003 | Frenken et al. | |
| 6,759,518 B1 | 7/2004 | Kontermann et al. | |
| 6,767,711 B2 | 7/2004 | Bander | |
| 7,163,680 B2 | 1/2007 | Bander | |
| 7,262,276 B2 | 8/2007 | Huang et al. | |
| 7,666,414 B2 | 2/2010 | Bander | |
| 7,807,162 B2 | 10/2010 | Silence | |
| 7,850,971 B2 | 12/2010 | Maddon et al. | |
| 8,114,965 B2 | 2/2012 | Maddon et al. | |
| 8,188,223 B2 | 5/2012 | Beirnaert et al. | |
| 8,236,308 B2 | 8/2012 | Kischel et al. | |
| 8,470,330 B2 | 6/2013 | Schuelke et al. | |
| 8,623,356 B2 | 1/2014 | Christopherson et al. | |
| 8,629,244 B2 | 1/2014 | Kolkman et al. | |
| 8,703,135 B2 | 4/2014 | Beste et al. | |
| 8,784,821 B1 | 7/2014 | Kufer et al. | |
| 8,846,042 B2 | 9/2014 | Zhou | |
| 8,907,071 B2 | 12/2014 | Sullivan et al. | |
| 8,937,164 B2 | 1/2015 | Descamps et al. | |
| 9,169,316 B2 | 10/2015 | Baty et al. | |
| 9,309,327 B2 | 4/2016 | Humphreys et al. | |
| 9,327,022 B2 | 5/2016 | Zhang et al. | |
| 9,340,621 B2 | 5/2016 | Kufer et al. | |
| 9,708,412 B2 | 7/2017 | Baeuerle et al. | |
| 9,920,115 B2 | 3/2018 | Dubridge et al. | |
| 2006/0046971 A1 | 3/2006 | Stuhler et al. | |
| 2006/0228364 A1 | 10/2006 | Dennis et al. | |
| 2006/0252096 A1 | 11/2006 | Zha et al. | |
| 2007/0178082 A1 | 8/2007 | Silence et al. | |
| 2007/0269422 A1 | 11/2007 | Beirnaert et al. | |
| 2008/0069772 A1 | 3/2008 | Stuhler et al. | |
| 2008/0260757 A1 | 10/2008 | Holt et al. | |
| 2009/0259026 A1 | 10/2009 | Tomlinson et al. | |
| 2010/0122358 A1 | 5/2010 | Brueggemann et al. | |
| 2010/0150918 A1 | 6/2010 | Kufer et al. | |
| 2010/0189727 A1 | 7/2010 | Rodeck et al. | |
| 2010/0291112 A1 | 11/2010 | Kellner et al. | |
| 2011/0129458 A1 | 6/2011 | Dolk et al. | |
| 2011/0165621 A1 | 7/2011 | Dreier et al. | |
| 2011/0262439 A1 | 10/2011 | Kufer et al. | |
| 2011/0275787 A1 | 11/2011 | Kufer et al. | |
| 2011/0313135 A1 | 12/2011 | Vanhove et al. | |
| 2012/0231024 A1 | 9/2012 | Elsaesser-Beile et al. | |
| 2012/0328619 A1 | 12/2012 | Fey et al. | |
| 2013/0017200 A1 | 1/2013 | Scheer et al. | |
| 2013/0266568 A1 | 10/2013 | Brinkmann et al. | |
| 2013/0267686 A1 | 10/2013 | Brinkmann et al. | |
| 2013/0273055 A1 | 10/2013 | Borges et al. | |
| 2013/0330335 A1 | 12/2013 | Bremel et al. | |
| 2014/0004121 A1 | 1/2014 | Fanslow, III et al. | |
| 2014/0023664 A1 | 1/2014 | Lowman et al. | |
| 2014/0045195 A1 | 2/2014 | Daugherty et al. | |
| 2014/0073767 A1 | 3/2014 | Lee et al. | |
| 2014/0088295 A1 | 3/2014 | Smith et al. | |
| 2014/0302037 A1 | 10/2014 | Borges et al. | |
| 2014/0322218 A1 | 10/2014 | Xiao et al. | |

(Continued)

FOREIGN PATENT DOCUMENTS

| | | |
|---|---|---|
| CN | 1563092 A | 1/2005 |
| EP | 1378520 A1 | 1/2004 |

(Continued)

OTHER PUBLICATIONS

Almagro et al. Humanization of antibodies. Front Biosci 13:1619-1633 (2008).

(Continued)

*Primary Examiner* — Nelson B Moseley, II
(74) *Attorney, Agent, or Firm* — Wilson Sonsini Goodrich & Rosati

(57) ABSTRACT

Disclosed herein are MSLN binding proteins with improved binding affinities and improved ability to mediate T cell dependent killing of cancer cells expressing mesothelin. Pharmaceutical compositions comprising the binding proteins disclosed herein and methods of using such formulations are further provided.

18 Claims, 13 Drawing Sheets

Specification includes a Sequence Listing.

(56) References Cited

U.S. PATENT DOCUMENTS

| | | |
|---|---|---|
| 2015/0037334 A1 | 2/2015 | Kufer et al. |
| 2015/0056206 A1 | 2/2015 | Zhou |
| 2015/0064169 A1 | 3/2015 | Wang et al. |
| 2015/0079088 A1 | 3/2015 | Lowman et al. |
| 2015/0079093 A1 | 3/2015 | Stuhler |
| 2015/0174268 A1 | 6/2015 | Li et al. |
| 2015/0183875 A1 | 7/2015 | Cobbold et al. |
| 2015/0232557 A1 | 8/2015 | Tan et al. |
| 2015/0274836 A1 | 10/2015 | Ho et al. |
| 2015/0274844 A1 | 10/2015 | Blankenship et al. |
| 2016/0024174 A1 | 1/2016 | Odunsi et al. |
| 2016/0032019 A1 | 2/2016 | Xiao et al. |
| 2016/0039942 A1 | 2/2016 | Cobbold et al. |
| 2016/0068605 A1 | 3/2016 | Nemeth et al. |
| 2016/0215063 A1 | 7/2016 | Bernett et al. |
| 2016/0251440 A1 | 9/2016 | Roobrouck et al. |
| 2016/0319040 A1 | 11/2016 | Dreier et al. |
| 2016/0340444 A1 | 11/2016 | Baeuerle et al. |
| 2017/0029502 A1 | 2/2017 | Raum et al. |
| 2017/0152316 A1 | 6/2017 | Cobbold et al. |
| 2017/0204164 A1 | 7/2017 | Himmler et al. |
| 2017/0275373 A1 | 9/2017 | Kufer et al. |
| 2017/0298149 A1 | 10/2017 | Baeuerle et al. |
| 2017/0334979 A1 | 11/2017 | Dubridge et al. |
| 2017/0334997 A1 | 11/2017 | Dubridge et al. |
| 2017/0369575 A1 | 12/2017 | Dubridge et al. |
| 2018/0148508 A1 | 5/2018 | Wang et al. |
| 2019/0031749 A1 | 1/2019 | Dubridge et al. |
| 2019/0225702 A1 | 7/2019 | Baeuerle et al. |

FOREIGN PATENT DOCUMENTS

| | | |
|---|---|---|
| EP | 1736484 A1 | 12/2006 |
| EP | 2336179 A1 | 6/2011 |
| JP | 2005501517 A | 1/2005 |
| WO | WO-9404678 A1 | 3/1994 |
| WO | WO-9937681 A2 | 7/1999 |
| WO | WO-0043507 A1 | 7/2000 |
| WO | WO-0190190 A2 | 11/2001 |
| WO | WO-02085945 A2 | 10/2002 |
| WO | WO-03025020 A1 | 3/2003 |
| WO | WO-03035694 A2 | 5/2003 |
| WO | WO-03064606 A2 | 8/2003 |
| WO | WO-2004003019 A2 | 1/2004 |
| WO | WO-2004041867 A2 | 5/2004 |
| WO | WO-2004042404 A1 | 5/2004 |
| WO | WO-2004049794 A2 | 6/2004 |
| WO | WO-2006122787 A1 | 11/2006 |
| WO | WO-2007042261 A2 | 4/2007 |
| WO | WO-2007062466 A1 | 6/2007 |
| WO | WO-2008028977 A2 | 3/2008 |
| WO | WO-2009025846 A2 | 2/2009 |
| WO | WO-2009030285 A1 | 3/2009 |
| WO | WO-2009147248 A2 | 12/2009 |
| WO | WO-2010003118 A1 | 1/2010 |
| WO | WO-2012131053 A1 | 10/2012 |
| WO | WO-2012158818 A2 | 11/2012 |
| WO | WO-2013036130 A1 | 3/2013 |
| WO | WO-2013104804 A2 | 7/2013 |
| WO | WO-2013110531 A1 | 8/2013 |
| WO | WO-2013128027 A1 | 9/2013 |
| WO | WO-2014033304 A2 | 3/2014 |
| WO | WO-2014138306 A1 | 9/2014 |
| WO | WO-2014140358 A1 | 9/2014 |
| WO | WO-2014151910 A1 | 9/2014 |
| WO | WO-2015103072 A1 | 7/2015 |
| WO | WO-2015150447 A1 | 10/2015 |
| WO | WO-2015184207 A1 | 12/2015 |
| WO | WO-2016009029 A1 | 1/2016 |
| WO | WO-2016034044 A1 | 3/2016 |
| WO | WO-2016046778 A2 | 3/2016 |
| WO | WO-2016105450 A2 | 6/2016 |
| WO | WO-2016171999 A2 | 10/2016 |
| WO | WO-2016179003 A1 | 11/2016 |
| WO | WO-2016187594 A1 | 11/2016 |
| WO | WO-2016210447 A1 | 12/2016 |
| WO | WO-2017025698 A1 | 2/2017 |
| WO | WO-2017041749 A1 | 3/2017 |
| WO | WO-2017079528 A1 | 5/2017 |
| WO | WO-2017136549 A1 | 8/2017 |
| WO | WO-2017156178 A1 | 9/2017 |
| WO | WO-2017201488 A1 | 11/2017 |
| WO | WO-2017201493 A1 | 11/2017 |
| WO | WO-2018071777 A1 | 4/2018 |
| WO | WO-2018098354 A1 | 5/2018 |
| WO | WO-2018098356 A1 | 5/2018 |
| WO | WO-2018136725 A1 | 7/2018 |
| WO | WO-2018160671 A1 | 9/2018 |
| WO | WO-2018160754 A2 | 9/2018 |
| WO | WO-2018204717 A1 | 11/2018 |
| WO | WO-2018209298 A1 | 11/2018 |
| WO | WO-2018209304 A1 | 11/2018 |
| WO | WO-2019075359 A1 | 4/2019 |
| WO | WO-2019075378 A1 | 4/2019 |

OTHER PUBLICATIONS

Argani et al. Mesothelin is overexpressed in the vast majority of ductal adenocarcinomas of the pancreas: identification of a new pancreatic cancer marker by serial analysis of gene expression (SAGE). Clin Cancer Res 7(12):3862-3868 (2001).
Baca et al. Antibody humanization using monovalent phage display. J Biol Chem 272(16):10678-10684 (1997).
Baeuerle et al. Bispecific T-cell engaging antibodies for cancer therapy. Cancer Res 69:4941-4944 (2009).
Bedouelle et al. Diversity and junction residues as hotspots of binding energy in an antibody neutralizing the dengue virus. FEBS J 273(1):34-46 (2006).
Bracci et al. Cyclophosphamide enhances the antitumor efficacy of adoptively transferred immune cells through the induction of cytokine expression, B-cell and T-cell homeostatic proliferation, and specific tumor infiltration. Clin Cancer Res 13(2 Pt 1):644-653 (2007).
Brown et al. Tolerance of single, but not multiple, amino acid replacements in antibody VH CDR 2: a means of minimizing B cell wastage from somatic hypermutation? J Immunol 156(9):3285-3291 (1996).
Carter et al. Humanization of an anti-p185HER2 antibody for human cancer therapy. PNAS USA 89(10):4285-4289 (1992).
Casset et al. A peptide mimetic of an anti-CD4 monoclonal antibody by rational design. Biochemical and Biophysical Research Communication 307:198-205 (2003).
Chang et al. Molecular cloning of mesothelin, a differentiation antigen present on mesothelium, mesotheliomas, and ovarian cancers. PNAS USA 93:136-140 (1996).
Chatalic et al. A Novel 111 In-labeled Anti-PSMA Nanobody for Targeted SPECT/CT Imaging of Prostate Cancer. J Nucl Med 56(7):1094-1099 and Supplemental Data (2015).
Chen et al. Selection and analysis of an optimized anti-VEGF antibody: Crystal structure of an affinity-matured Fab in complex with antigen. J Mol Bio 293:865-881 (1999).
Chothia et al. Canonical structures for the hypervariable regions of immunoglobulins. J Mol Biol 196(4):901-917 (1987).
Co-pending U.S. Appl. No. 15/821,498, filed Nov. 22, 2017.
Co-pending U.S. Appl. No. 15/821,530, filed Nov. 22, 2017.
Co-pending U.S. Appl. No. 15/977,988, filed May 11, 2018.
Corso et al. Real-time detection of mesothelin in pancreatic cancer cell line supernatant using an acoustic wave immunosensor. Cancer Detect Prev 30:180-187 (2006).
Creaney et al. Detection of malignant mesothelioma in asbestos-exposed individuals: the potential role of soluble mesothelin-related protein. Hematol. Oncol. Clin. North Am. 19:1025-1040 (2005).
Cristaudo et al. Clinical significance of serum mesothelin in patients with mesothelioma and lung cancer. Clin. Cancer Res. 13:5076-5081 (2007).
De Pascalis et al. Grafting of "abbreviated" complementarity-determining regions containing specificity-determining residues essential for ligand contact to engineer a less immunogenic humanized monoclonal antibody. J Immunol. 169(6):3076-3084 (2002).

(56) References Cited

OTHER PUBLICATIONS

Document D28—Investigation of human CD3ε variants binding to monoclonal antibodies. Submitted by Pfizer to the European Patent Register on Apr. 30, 2014 in connection with their opposition to the EP2155783 patent. (3 pages) (2014).
Document D78—CD3ε N-terminal peptide bound to the CDRs of SP24. Submitted by Janssen Biotech to the European Patent Register on Mar. 18, 2016 in connection with their opposition to the EP2155783 patent (1 page) (2016).
Document D79—Interactions between CD3ε and SP34 CDR residues. CD3ε residues are in ellipses, SP34 CDR residues are in boxes. Submitted by Janssen Biotech to the European Patent Register on Mar. 18, 2016 in connection with their opposition to the EP2155783 patent (1 page) (2016).
Document D83—Alignment of variable domains from the prior art and the patent. Submitted by Janssen Biotech to the European Patent Register on Mar. 18, 2016 in connection with their opposition to the EP2155783 patent (1 page) (2016).
Frankel et al. Targeting T cells to tumor cells using bispecific antibodies. Curr Opin Chem Biol 17(3):385-392 (2013).
Goodman et al. The Pharmaceutical Basis of Therapeutics. 6th ed. pp. 21-25 (1980).
Goswami et al. Developments and Challenges for mAb-Based Therapeutics. Antibodies 2:452-500 (2013).
Gross et al. Endowing T cells with antibody specificity using chimeric T cell receptors. FASEB J. 6(15):3370-3378 (1992).
Gubbels et al. Mesothelin-MUC16 binding is a high affinity, N-glycan dependent interaction that facilitates peritoneal metastasis of ovarian tumors. Mol Cancer 5:50 (2006).
Harding et al. The immunogenicity of humanized and fully human antibodies: residual immunogenicity resides in the CDR regions. MAbs 2(3):256-265 (2010).
Hassan et al. Detection and quantitation of serum mesothelin, a tumor marker for patients with mesothelioma and ovarian cancer. Clin Cancer Res 12:447-453 (2006).
Hassan et al. Mesothelin: a new target for immunotherapy. Clin Cancer Res 10:3937-3942 (2004).
Hassan et al. Mesothelin targeted cancer immunotherapy. Eur J Cancer 44:46-53 (2008).
Hassan et al. Phase I study of SS1P, a recombinant anti-mesothelin immunotoxin given as a bolus I.V. infusion to patients with mesothelin-expressing mesothelioma, ovarian, and pancreatic cancers. Clin Cancer Res 13(17):5144-5149 (2007).
Hassan et al. Preclinical evaluation of MORAb-009, a chimeric antibody targeting tumor-associated mesothelin. Cancer Immun. 7:20 (2007).
Hellstrom et al. Mesothelin variant 1 is released from tumor cells as a diagnostic marker. Cancer Epidemiol Biomarkers Prev 15:1014-1020 (2006).
Ho et al. A novel high-affinity human monoclonal antibody to mesothelin. Int J Cancer 128:2020-2030 (2011).
Ho et al. Mesothelin expression in human lung cancer. Clin Cancer Res 13:1571-1575 (2007).
Ho et al. Mesothelin is shed from tumor cells. Cancer Epidemiol Biomarkers Prev 15:1751 (2006).
Holt et al. Anti-serum albumin domain antibodies for extending the half-lives of short lived drugs. Protien Eng Des Sel 21(5):283-288 (2008).
Hutchinson et al. Mutagenesis at a specific position in a DNA sequence. J Biol Chem 253:6551-6560 (1978).
Janssen letter—Submission under Rule 116 EPC. Submitted by Janssen Biotech to the European Patent Register on Mar. 18, 2016 in connection with their opposition to the EP2155783 patent (6 pages) (2016).
Kabat et al. Identical V region amino acid sequences and segments of sequences in antibodies of different specificities. Relative contributions of VH and VL genes, minigenes, and complementarity-determining regions to binding of antibody-combining sites. J Immunol 147:1709-1719 (1991).
Kojima et al. Molecular cloning and expression of megakaryocyte potentiating factor cDNA. J Biol Chem 270:21984-21990 (1995).
Le Gall et al. Immunosuppressive properties of anti-CD3 single-chain Fv and diabody. J Immunol Methods 285(1):111-127 (2004).
Li et al. Development of novel tetravalent anti-CD20 antibodies with potent antitumor activity. Cancer Res 68:2400-2408 (2008).
Liu et al. MGD011, a CD19 x CD3 Dual Affinity Re-Targeting Bi-specific Molecule Incorporating Extended Circulating Half-life for the Treatment of B-cell Malignancies. Clin Cancer Res 23(6):1506-1518 (epub 2016) (2017).
Lutterbuese et al. T cell-engaging BiTE antibodies specific for EGFR potently eliminate KRAS- and BRAF-mutated colorectal cancer cells. PNAS 107:12605-12610 (2007).
MacCallum et al. Antibody-antigen interactions: contact analysis and binding site topography. J Mol Biol. 262(5):732-745 (1996).
Mirsky et al. Antibody-Specific Model of Amino Acid Substitution for Immunological Inferences from Alignments of Antibody Sequences. Mol. Biol. Evol. 32(3):806-819 (2014).
Morea et al. Antibody modeling: implications for engineering and design. Methods 20(3):267-279 (2000).
Moschella et al. Unraveling cancer chemoimmunotherapy mechanisms by gene and protein expression profiling of responses to cyclophosphamide. Cancer Res 71(10):3528-3539 (2011).
Muller et al. Improving the pharmacokinetic properties of biologics by fusion to an anti-HSA shark VNAR domain. MAbs 4(6):673-685 (2012).
Muul et al. Persistence and expression of the adenosine deaminase gene for 12 years and immune reaction to gene transfer components: long-term results of the first clinical gene therapy trial. Blood 101(7):2563-2569 (2003).
Nazarian et al. Characterization of bispecific T-cell Engager (BiTE) antibodies with a high-capacity T-cell dependent cellular cytotoxicity (TDCC) assay. J Biomol Screen 20:519-527 (2015).
Nelson et al. Antibody fragments Hope and Hype. mAbs 2(1):77-83 (2010).
Ohiro et al. A homogeneous and noncompetitive immunoassay based on the enhanced fluorescence resonance energy transfer by leucine zipper interaction. Anal Chem 74(22):5786-5792 (2002).
O'Keefe et al. Chapter 18: Prostate specific membrane antigen. In: Chung L.W.K., Isaacs W.B., Simons J.W. (eds) Prostate Cancer. Contemporary Cancer Research. Humana Press, Totowa, NJ (pp. 307-326) (2001).
Ordonez. Application of mesothelin immunostaining in tumor diagnosis. Am J Surg Pathol 27:1418-1428 (2003).
Padlan. Anatomy of the Antibody Molecule. Mol Immunol 31(3):169-217 (1994).
Padlan et al. Structure of an antibody-antigen complex: Crystal structure of the HyHEL-10 Fab-lysozyme complex. PNAS USA 86:5938-5942 (1989).
Pawluczkowycz et al. Binding of submaximal C1q promotes complement-dependent cytotoxicity (CDC) of B cells opsonized with anti-CD20 mAbs ofatumumab (OFA) or rituximab (RTX): considerably higher levels of CDC are induced by OFA than by RTX. J Immunol 183:749-758 (2009).
PCT/US2016/033644 International Preliminary Report on Patentability dated Nov. 30, 2017.
PCT/US2016/33644 International Search Report and Written Opinion dated Sep. 6, 2016.
PCT/US2017/033665 International Search Report and Written Opinion dated Oct. 18, 2017.
PCT/US2017/033673 International Search Report and Written Opinion dated Oct. 18, 2017.
PCT/US2017056530 International Search Report and Written Opinion dated Jan. 23, 2018.
PCT/US2017/063121 International Search Report and Written Opinion dated Mar. 26, 2018.
PCT/US2017/063121 Invitation to Pay Additional Fees dated Feb. 1, 2018.
PCT/US2017/063126 International Search Report and Written Opinion dated Apr. 5, 2018.
PCT/US2017/063126 Invitation to Pay Additional Fees dated Feb. 1, 2018.

(56) References Cited

OTHER PUBLICATIONS

Pfizer letter—Opposition to European Patent EP2155783 (Application 08735001.3). Submitted by Pfizer to the European Patent Register on Apr. 30, 2014 in connection with their opposition to the EP2155783 patent. (pp. 1-23 and Appendix 1 on pp. 24-26) (2014).
Presta et al. Humanization of an antibody directed against IgE. J Immunol 151:2623-2632 (1993).
Riechmann et al. Single domain antibodies: comparison of camel VH and camelised human VH domains. J Immunol Methods 231(1-2):25-38 (1999).
Rosok et al. A Combinatorial Library Strategy for the Rapid Humanization of Anticarcinoma BR96 Fab. J Biol Chem 271:22611-22618 (1996).
Rudikoff et al. Single amino acid substitution altering antigen-binding Specificity. PNAS USA 79:1979-1983 (1982).
Rump et al. Binding of ovarian cancer antigen CA125/MUC16 to mesothelin mediates cell adhesion. J Biol Chem 279:9190-9198 (2004).
Sadelain et al. Targeting tumours with genetically enhanced T lymphocytes. Nat Rev Cancer 3(1):35-45 (2003).
Sims et al. A humanized CD18 antibody can block function without cell destruction. J Immunol., 151 (1993): 2296-2308.
Bortoletto et al. Optimizing anti-CD3 affinity for effective T cell targeting against tumor cells. Eur J Immunol 32:3102-3107 (2002).
Tang et al. A human single-domain antibody elicits potent antitumor activity by targeting an epitope in mesothelin close to the cancer cell surface. Mol. Cancer Thera 12(4):416-426 (2013).
Thomas et al. Mesothelin-specific CD8(+) T cell responses provide evidence of in vivo cross-priming by antigen-presenting cells in vaccinated pancreatic cancer patients. J Exp Med 200:297-306 (2004).
U.S. Appl. No. 15/160,984 Office Action dated Feb. 24, 2017.
U.S. Appl. No. 15/160,984 Office Action dated Sep. 22, 2016.
U.S. Appl. No. 15/600,264 Office Action dated Apr. 26, 2018.
U.S. Appl. No. 15/600,264 Office Action dated Oct. 3, 2017.
U.S. Appl. No. 15/600,582 Office Action dated Nov. 16, 2017.
U.S. Appl. No. 15/704,620 Office Action dated Oct. 26, 2017.
Vajdos et al. Comprehensive functional maps of the antigen-binding site of an anti-ErbB2 antibody obtained with shotgun scanning mutagenesis. J Mol Biol 320:415-428 (2002).
Van Den Beuchken et al. Building novel binding ligands to B7.1 and B7.2 based on human antibody single variable light chain domains. J Mol biol 310:591-601 (2001).
Vaughan et al. Human antibodies by design. Nature Biotech 16:535-539 (1998).
Wu et al. Humanization of a murine monoclonal antibody by simultaneous optimization of framework and CDR residues. J.Mol. Biol. 294:151-162 (1999).
Yee et al. Adoptive T cell therapy using antigen-specific CD8+ T cell clones for the treatment of patients with metastatic melanoma: in vivo persistence, migration, and antitumor effect of transferred T cells. PNAS USA 99(25):16168-16173 (2002).
PCT/US2018/020185 International Search Report and Written Opinion dated Jun. 15, 2018.
PCT/US2018/020307 International Search Report and Written Opinion dated Aug. 24, 2018.
PCT/US2018/030983 Invitation to Pay Additional Fees dated Jul. 31, 2018.
PCT/US2018/032427 International Search Report and Written Opinion dated Sep. 13, 2018.
PCT/US2018/32418 Invitation to Pay Additional Fees dated Jul. 23, 2018.
PCT/US2018/32427 Invitation to Pay Additional Fees dated Jul. 24, 2018.
Schmittgen et al. Expression of prostate specific membrane antigen and three alternatively spliced variants of PSMA in prostate cancer patients. Int J Cancer 107:323-329 (2003).
U.S. Appl. No. 15/821,530 Office Action dated Sep. 25, 2018.
Caldas et al. Humanization of the anti-CD18 antibody 6.7: an unexpected effect of a framework residue in binding to antigen. Mol Immunol. 39(15):941-952 (2003).
Chang et al. Loop-sequence features and stability determinants in antibody variable domains by high-throughput experiments. Structure 22(1):9-21 (2014).
Chien et al. Significant structural and functional change of an antigen-binding site by a distant amino acid substitution: proposal of a structural mechanism. PNAS USA 86(14):5532-5536 (1989).
Co-pending U.S. Appl. No. 16/159,554, filed Oct. 12, 2018.
Foote et al. Antibody Framework Residues Affecting the Conformation of the Hypervariable Loops. J. Mol. Biol. 224(2):487-99 (1992).
Giusti et al. Somatic diversification of S107 from an antiphosphocholine to an anti-DNA autoantibody is due to a single base change in its heavy chain variable region. PNAS USA 84(9):2926-30 (1987).
Goldman et al. Enhancing Stability of Camelid and Shark Single Domain Antibodies: An Overview. Front. Immunol. 8:865 (2017).
Gussow et al. Chapter 5: Humanization of Monoclonal Antibodies. Methods in Enzymology 203:99-121 (1991).
Holm et al. Functional mapping and single chain construction of the anti-cytokeratin 8 monoclonal antibody TS1. Mol Immunol 44(6):1075-1084 (2007).
Liu et al. A New Format of Single Chain Tri-specific Antibody with Diminished Molecular Size Efficiently Induces Ovarian Tumor Cell Killing. Biotechnology Letters 27(22):1821-1827 (2005).
Mariuzza et al. The structural basis of antigen-antibody recognition. Annu Rev Biophys Biophys Chem 16:139-159 (1987).
Mueller et al. Improved pharmacokinetics of recombinant bispecific antibody molecules by fusion to human serum albumin. J Bio Chem 282(17):12650-12660 (2007).
Nunez-Prado et al. The coming of age of engineered multivalent antibodies. Drug Discovery Today 20(5):588-594 (2015).
PCT/US2018/030983 International Search Report and Written Opinion dated Sep. 25, 2018.
PCT/US2018/032418 International Search Report and Written Opinion dated Sep. 24, 2018.
Running Deer et al. High-level expression of proteins in mammalian cells using transcription regulatory sequences from the Chinese hamster EF-1alpha gene. Biotechnol Prog. 20:880-889 (2004).
Saerens et al. Identification of a universal VHH framework to graft non-canonical antigen-binding loops of camel single-domain antibodies. J. Mol. Biol. 352(3):597-607 (2005).
Su et al. PSMA specific single chain antibody-mediated targeted knockdown of Notch1 inhibits human prostate cancer cell proliferation and tumor growth. Cancer Lett. 338 (2): 282-291 (2013).
Tiller et al. Facile Affinity Maturation of Antibody Variable Domains Using Natural Diversity Mutagenesis. Front. Immunol. 8:986 (2017).
Tutt et al. Trispecific F(Ab')3 Derivatives That Use Cooperative Signaling Via the Tcr/Cd3 Complex and Cd2 to Activate and Redirect Resting Cytotoxic T Cells. J Immunol 147(1):60-69 (1991).
U.S. Appl. No. 15/600,264 Office Action dated Nov. 27, 2018.
U.S. Appl. No. 15/821,498 Office Action dated Oct. 26, 2018.
Vincke et al. General strategy to humanize a camelid single-domain antibody and identification of a universal humanized nanobody scaffold. J. Biol. Chem. 284(5):3273-3284 (2009).
Wang et al. A New Recombinant Single Chain Trispecific Antibody Recruits T Lymphocytes to Kill CEA (Carcinoma Embryonic Antigen) Positive Tumor Cells In Vitro Efficiently. Journal of Biochemistry 135(4):555-565 (2004).
Winkler et al. Changing the antigen binding specificity by single point mutations of an anti-p24 (HIV-1) antibody. J Immunol. 165(8):4505-4514 (2000).
Yu et al. Rationalization and design of the complementarity determining region sequences in an antibody-antigen recognition interface. PLoS One 7(3):e33340 (2012).
Zare et al. Production of nanobodies against prostate-specific membrane antigen (PSMA) recognizing LnCaP cells. Int. J. Biol. Markers 29(2):e169-e179 (2014).
Zhu et al. COMBODY: one-domain antibody multimer with improved avidity. Immunology and Cell Biology 88(6):667-675 (2010).
Chen et al. Fusion protein linkers: Property, design and functionality. Advanced Drug Delivery Reviews 65:1357-1369 (2013).

(56) References Cited

OTHER PUBLICATIONS

Dennis et al. Imaging Tumors with an Albumin-Binding Fab, a Novel Tumor-Targeting Agent. Cancer Res 67(1):254-61 (2007).
Hipp et al. A novel BCMA/CD3 bispecific T-cell engager for the treatment of multiple myeloma induces selective lysis in vitro and in vivo. Leukemia 31(8):1743-1751 (2017).
Hopp et al. The effects of affinity and valency of an albumin-binding domain (ABD) on the half-life of a single-chain diabody-ABD fusion protein. Protein Eng. Des. Sel. 23(11):827-34 (2010).
Laabi et al. The BCMA gene, preferentially expressed during B lymphoid maturation, is bidirectionally transcribed. Nucleic Acids Res 22(7):1147-1154 (1994).
Müller et al. Improved Pharmacokinetics of Recombinant Bispecific Antibody Molecules by Fusion to Human Serum Albumin. J. Biol. Chem. 282(17):12650-60 (2007).
Ramadoss et al. An Anti-B Cell Maturation Antigen bispecific Antibody for Multiple Myeloma. J. Am. Chem. Soc. 137(16):5288-91 (2015).
Smirnova et al. Identification of new splice variants of the genes BAFF and BCMA. Mol. Immunol. 45 (4):1179-83 (2008).
Spiess et al. Alternative molecular formats and therapeutic applications for bispecific antibodies. Mol. Immunol. 67(2 Pt A):95-106 (2015).
Stork et al. A novel tri-functional antibody fusion protein with improved pharmacokinetic properties generated by fusing a bispecific single-chain diabody with an albumin-binding domain from streptococcal protein G. Protein Eng. Des. Sel. 20(11):569-76 (2007).
Tijink et al. Improved tumor targeting of anti-epidermal growth factor receptor nanobodies through albumin binding: taking advantage of modular Nanobody technology. Mol. Cancer Ther. 7(8):2288-97 (2008).
U.S. Appl. No. 16/159,554 Office Action dated Jun. 7, 2019.
Rozan et al. Single-domain antibody-based and linker-free bispecific antibodies targeting FcγRIII induce potent antitumor activity without recruiting regulatory T cells. Mol Cancer Ther 12(8):1481-1491 (2013).
Schmidt et al. Cloning and Characterization of Canine Prostate-Specific Membrane Antigen. The Prostate 73:642-650 (2013).
U.S. Appl. No. 15/600,264 Office Action dated Apr. 25, 2019.
U.S. Appl. No. 15/821,498 Office Action dated May 3, 2019.
U.S. Appl. No. 15/821,530 Office Action dated Apr. 3, 2019.
U.S. Appl. No. 15/977,988 Office Action dated Mar. 26, 2019.
Austin et al. Cancer Research (Jul. 2018) vol. 78, No. 13, Supp. Supplement 1. Abstract No. 1781. Meeting Info: 2018 Annual Meeting of the American Association for Cancer Research, AACR 2018. Chicago, IL, United States. Apr. 14, 2018-Apr. 18, 2018).
Cho et al. Targeting B Cell Maturation Antigen (BCMA) in Multiple Myeloma: Potential Uses of BCMA-Based Immunotherapy. Front Immunol 9:1821 (2018).
Co-pending U.S. Appl. No. 16/159,545, filed Oct. 12, 2018.
Lu et al. In vitro and in vivo antitumor effect of a trivalent bispecific antibody targeting ErbB2 and CD16. Cancer Biol Ther. 7(11):1744-1750 (2008).
PCT/US2018/014396 International Search Report and Written Opinion dated Jun. 14, 2018.
PCT/US2018/055659 International Search Report and Written Opinion dated Feb. 21, 2019.
PCT/US2018/055659 Invitation to Pay Additional Fees dated Dec. 19, 2018.
PCT/US2018/055682 International Search Report and Written Opinion dated Mar. 1, 2019.
PCT/US2018/055682 Invitation to Pay Additional Fees dated Jan. 8, 2019.
Sternjak et al. Cancer Research, (Jul. 2017) vol. 77, No. 13, Supp. Supplement 1. Abstract No. 3630. Meeting Info: American Association for Cancer Research Annual Meeting 2017. Washington, DC, United States. Apr. 1, 2017-Apr. 5, 2017.
U.S. Appl. No. 15/977,988 Preinterview First Office Action dated Jan. 25, 2019.
Muyldermans. Nanobodies: natural single-domain antibodies. Annu Rev Biochem, 82:775-797, 2013.
PCT/US2018/014396 International Preliminary Report on Patentability dated Aug. 1, 2019.
PCT/US2019/032224 International Search Report and Written Opinion dated Aug. 28, 2019.
PCT/US2019/032302 International Search Report and Written Opinion dated Aug. 22, 2019.
PCT/US2019/032306 International Search Report and Written Opinion dated Aug. 22, 2019.
PCT/US2019/032307 International Search Report and Written Opinion dated Aug. 22, 2019.
U.S. Appl. No. 15/977,988 Office Action dated Aug. 20, 2019.
U.S. Appl. No. 16/159,545 Office Action dated Aug. 6, 2019.

MESOTHELIN BINDING PROTEINS

CROSS-REFERENCE

This application claims the benefit of U.S. Provisional Application Nos. 62/505,719 filed on May 12, 2017, and 62/657,417 filed Apr. 13, 2018, each incorporated by reference herein in its entirety.

SEQUENCE LISTING

The instant application contains a Sequence Listing which has been submitted electronically in ASCII format and is hereby incorporated by reference in its entirety. Said ASCII copy, created on May 11, 2018, is named 47517-719_201_SL.txt and is 145,039 bytes in size.

INCORPORATION BY REFERENCE

All publications, patents, and patent applications mentioned in this specification are herein incorporated by reference to the same extent as if each individual publication, patent, or patent application was specifically and individually indicated to be incorporated by reference, and as if set forth in their entireties.

BACKGROUND OF THE INVENTION

The present disclosure provides mesothelin (MSLN) binding proteins which can be used for diagnosing and treating indications correlated to the expression of MSLN. Mesothelin (MSLN) is a GPI-linked membrane bound tumor antigen MSLN is overexpressed ovarian, pancreatic, lung and triple-negative breast cancers and mesothelioma. Normal tissue expression of MSLN is restricted to single-cell, mesothelial layers lining the pleural, pericardial, and peritoneal cavities. Overexpression of MSLN is associated with poor prognosis in lung adenocarcinoma and triple-negative breast cancer. MSLN has been used as cancer antigen for numerous modalities, including immunotoxins, vaccines, antibody drug conjugates and CAR-T cells. Early signs of clinical efficacy have validated MSLN as a target, but therapies with improved efficacy are needed to treat MSLN-expressing cancers.

SUMMARY OF THE INVENTION

One embodiment provides a single domain mesothelin binding protein, wherein said protein comprises one or more conserved regions comprising a sequence identical to or comprising one or more amino acid residue substitutions relative to any one of SEQ ID Nos.: 41-50. In some embodiments, said protein comprises a sequence that is at least 80% identical to a sequence selected from the group consisting of SEQ ID NOs: 1-40, 58, and 60-62. In some embodiments, said protein comprises one or more modifications that result in humanization of the binding protein. In some embodiments, said protein comprises a VHH domain that specifically binds to MSLN. In some embodiments, said protein comprises a VHH domain derived from a non-human source. In some embodiments, said protein comprises a llama VHH domain. In some embodiments, said protein comprises 111 amino acids to 124 amino acids. In some embodiments, said protein binds to an epitope of mesothelin, wherein said epitope is located in region I, comprising amino acid residues 296-390 of SEQ ID NO: 57, region II comprising amino acid residue 391-486 of SEQ ID NO: 57, or region III comprising amino acid residues 487-598 of SEQ ID NO: 57. In some embodiments, said protein comprises one or more CDRs selected from SEQ ID Nos.: 51-56 and 63-179. In some embodiments, said protein comprises an amino acid sequence as set forth in any one of SEQ ID Nos.: 1-40, 58, and 60-62. One embodiment provides a single domain mesothelin binding protein, wherein said protein comprises one or more CDRs selected from SEQ ID Nos.: 51-56 and 63-179. In some embodiments, said protein comprises the following formula:

$$f1\text{-}r1\text{-}f2\text{-}r2\text{-}f3\text{-}r3\text{-}f4$$

wherein, r1 CDR1; r2 is CDR2; and r3 CDR3; and wherein f1, f2, f3 and f4 are framework residues.

In some embodiments, said protein comprises a CDR1 comprising a sequence set forth in any one of SEQ ID Nos.: 51, 54, and 63-101. In some embodiments, said protein comprises a CDR2 comprising a sequence set forth in any one of SEQ ID Nos.: 52, 55, and 102-140. In some embodiments, said protein comprises a CDR3 comprising a sequence set forth in any one of SEQ ID Nos.: 53, 56, and 141-179. In some embodiments, f1 comprises a sequence as set forth in any one of SEQ ID Nos.: 180-218. In some embodiments, f2 comprises a sequence as set forth in any one of SEQ ID Nos.: 219-257. In some embodiments, f3 comprises a sequence as set forth in any one of SEQ ID Nos.: 258-296. In some embodiments, f4 comprises a sequence as set forth in any one of SEQ ID Nos.: 297-335. In some embodiments, said protein comprises an amino acid sequence as set forth in any one of SEQ ID Nos.: 1-40, 58, and 60-62.

One embodiment provides a method for the treatment or amelioration of a proliferative disease, or a tumorous disease, comprising the administration of a single domain mesothelin binding protein comprising one or more CDRs selected from SEQ ID Nos.: 51-56 and 63-179, to a subject in need thereof. In some embodiments, the method comprises administering the single domain mesothelin binding protein at a dose of up to 10 mg/kg. In some embodiments, the single domain mesothelin binding protein is administered once a week, twice per week, every other day, or every three weeks. In some embodiments, the subject is human. In some embodiments, the method further comprises administration of an agent in combination with the single domain mesothelin binding protein. In some embodiments, the single domain mesothelin binding protein selectively binds to tumor cells expressing mesothelin. In some embodiments, the single domain mesothelin binding protein mediates T cell killing of tumor cells expressing mesothelin. In some embodiments, the tumorous disease comprises a solid tumor disease. In some embodiments, the solid tumor disease comprises mesothelioma, lung cancer, gastric cancer, ovarian cancer, or triple negative breast cancer. In some embodiments, the solid tumor disease is metastatic.

One embodiment provides a single domain mesothelin binding protein, wherein said protein comprises one or more conserved regions comprising a sequence identical to or comprising one or more amino acid residue substitutions relative to SEQ ID NO: 41, 42, 43, or 44. In some embodiments, said protein comprises a conserved region comprising a sequence identical to or comprising one or more amino acid residue substitutions relative to SEQ ID NO: 41. In some embodiments, said protein comprises a conserved region comprising a sequence identical to or comprising one or more amino acid residue substitutions relative to SEQ ID NO: 42. In some embodiments, said protein comprises a conserved region comprising a sequence identical to or comprising one or more amino acid residue substitutions relative to SEQ ID NO: 43. In some embodiments, said protein comprises a conserved region comprising a sequence identical to or comprising one or more amino acid residue substitutions relative to SEQ ID NO: 44. In some embodiments, said protein comprises (i) a stretch of amino acids corresponding to SEQ ID NO: 41; (ii) a stretch of amino acids corresponding to SEQ ID NO: 42; (iii) a stretch of amino acids corresponding to SEQ ID NO: 43; and (iv) a stretch of amino acids corresponding to SEQ ID NO: 44.

One embodiment provides a single domain mesothelin binding protein, wherein said protein comprises the following formula:

$$f1\text{-}r1\text{-}f2\text{-}r2\text{-}f3\text{-}r3\text{-}f4$$

wherein, r1 is identical to or comprises one or more amino acid residue substitutions relative to SEQ ID NO: 51; r2 is identical to or comprises one or more amino acid residue substitutions relative to SEQ ID NO: 52; and r3 is identical to or comprises one or more amino acid residue substitutions relative to SEQ ID NO: 53; and wherein f1, f2, f3 and f4 are framework residues. In some embodiments, said protein comprises a sequence that is at least 80% identical to a sequence selected from the group consisting of SEQ ID NOs: 1-29, 30-40, 58, and 60-62. In some embodiments, said protein comprises one or more modifications that result in humanization of the binding protein. In some embodiments, the modification comprises substitutions, additions, or deletions of amino acid residues. In some embodiments, said protein comprises 111 amino acids to 124 amino acids. In some embodiments, said protein comprises a VHH domain derived from a non-human source. In some embodiments, said protein comprises a llama VHH domain. In some embodiments, said epitope is located in region I, comprising amino acid residues 296-390 of SEQ ID NO: 57, region II comprising amino acid residue 391-486 of SEQ ID NO: 57, or region III comprising amino acid residues 487-598 of SEQ ID NO: 57.

One embodiment provides a single domain mesothelin binding protein, wherein said protein comprises one or more conserved regions comprising a sequence identical to or comprising one or more amino acid residue substitutions relative to SEQ ID NO: 45, 46, 47, 48, 49, or 50. In some embodiments, said protein comprises a conserved region comprising a sequence identical to or comprising one or more amino acid residue substitutions relative to SEQ ID NO: 45. In some embodiments, said protein comprises a conserved region comprising a sequence identical to or comprising one or more amino acid residue substitutions relative to SEQ ID NO: 46. In some embodiments, said protein comprises a conserved region comprising a sequence identical to or comprising one or more amino acid substitutions residue relative to SEQ ID NO: 47. In some embodiments, said protein comprises a conserved region comprising a sequence identical to or comprising one or more amino acid residue substitutions relative to SEQ ID NO: 48. In some embodiments, said protein comprises a conserved region comprising a sequence identical to or comprising one or more amino acid residue substitutions relative to SEQ ID NO: 49. In some embodiments, said protein comprises a conserved region comprising a sequence identical to or comprising one or more amino acid residue substitutions relative to SEQ ID NO: 50. In some embodiments, said protein comprises (i) a stretch of amino acids corresponding to SEQ ID NO: 45; (ii) a stretch of amino acids corresponding to SEQ ID NO: 46; (iii) a stretch of amino acids corresponding to SEQ ID NO: 47, (iv) a stretch of amino acids corresponding to SEQ ID NO: 48, (v) a stretch of amino acids corresponding to SEQ ID NO: 49, and (vi) a stretch of amino acids corresponding to SEQ ID NO: 50.

One embodiment provides a single domain mesothelin binding protein, wherein said protein comprises the following formula:

$$f1\text{-}r1\text{-}f2\text{-}r2\text{-}f3\text{-}r3\text{-}f4$$

wherein, r1 is identical to or comprises one or more amino acid residue substitutions relative to SEQ ID NO: 54; r2 is identical to or comprises one or more amino acid residue substitutions relative to SEQ ID NO: 55; and r3 is identical to or comprises one or more amino acid residue substitutions relative to SEQ ID NO: 56; and wherein f1, f2, f3 and f4 are framework residues. In some embodiments, said protein comprises a sequence that is at least 80% identical to a sequence selected from the group consisting of SEQ ID Nos: 30-40, 58, and 60-62. In some embodiments, said protein comprises 111 amino acids to 119 amino acids. In some embodiments, said protein comprises a VHH domain derived from a non-human source. In some embodiments, said protein comprises a llama VHH domain. In some embodiments, said protein binds to a human mesothelin protein comprising the sequence set forth as SEQ ID NO: 57. In some embodiments, said protein binds to an epitope of mesothelin, wherein said epitope is located in region I, comprising amino acid residues 296-390 of SEQ ID NO: 57, region II comprising amino acid residue 391-486 of SEQ ID NO: 57, or region III comprising amino acid residues 487-598 of SEQ ID NO: 57. In some embodiments, said binding protein is a chimeric antibody, or a humanized antibody. In some embodiments, said binding protein is a single domain antibody. In some embodiments, said binding protein is a humanized single domain antibody.

One embodiment provides a single domain mesothelin binding protein, wherein said protein comprises one or more CDRs selected from SEQ ID Nos.: 51-56 and 63-179. In some embodiments, said protein comprises a CDR1 comprising a sequence set forth in any one of SEQ ID Nos.: 51, 54, and 63-101. In some embodiments, said protein comprises a CDR2 comprising a sequence set forth in any one of SEQ ID Nos.: 52, 55, and 102-140. In some embodiments, said protein comprises a CDR3 comprising a sequence set forth in any one of SEQ ID Nos.: 53, 56, and 141-179. In some embodiments, said protein comprises a framework region 1 (f1) comprising a sequence as set forth in any one of SEQ ID Nos.: 180-218. In some embodiments, said protein comprises a framework region 2 (f2) comprising a sequence as set forth in any one of SEQ ID Nos.: 219-257. In some embodiments, said protein comprises a framework region 3 (f3) comprising a sequence as set forth in any one of SEQ ID Nos.: 258-296. In some embodiments, said protein comprises a framework region 4 (f4) comprising a sequence as set forth in any one of SEQ ID Nos.: 297-335. In some embodiments, said protein comprises an amino acid sequence as set forth in any one of SEQ ID Nos.: 1-40, and 58.

One embodiment provides a polynucleotide encoding a single domain mesothelin binding protein according to any one of the above embodiments. A further embodiment provides a vector comprising the polynucleotide of the above embodiment. A further embodiment provides a host cell transformed with the vector according to the above embodiment.

One embodiment provides a pharmaceutical composition comprising (i) a single domain mesothelin binding protein according to any one of the above embodiments, the polynucleotide according to any one of the above embodiments, the vector according to any one of the above embodiments, or the host cell according to any one of the above embodiments, and (ii) a pharmaceutically acceptable carrier.

A further embodiment provides a process for the production of a single domain mesothelin binding protein according to any one of the above embodiments, said process comprising culturing a host transformed or transfected with a vector comprising a nucleic acid sequence encoding a single domain mesothelin binding protein according to any one of the above embodiments under conditions allowing the expression of the mesothelin binding protein and recovering and purifying the produced protein from the culture.

One embodiment provides a method for the treatment or amelioration of a proliferative disease, or a tumorous disease, comprising the administration of the mesothelin binding protein any one of the above embodiments, to a subject in need thereof. In some embodiments, the subject is human. In some embodiments, the method further comprises administration of an agent in combination with the single domain mesothelin binding protein according to any one of the above embodiments. In some embodiments, the single domain mesothelin binding protein selectively binds to tumor cells expressing mesothelin. In some embodiments, the single domain mesothelin binding protein mediates T cell killing of tumor cells expressing mesothelin. In some embodiments, the tumorous disease comprises a solid tumor disease. In some embodiments, the solid tumor disease comprises mesothelioma, lung cancer, gastric cancer, ovarian cancer, or triple negative breast cancer. In some embodiments, the solid tumor disease is metastatic.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 9 illustrates binding of a trispecific MSLN target antigen binding protein containing an exemplary MSLN binding domain of this disclosure (MH6T) to MSLN expressing cell lines or MSLN non-expressing cell lines.

FIG. 9A further illustrates lack of binding of a control trispecific protein (GFP TriTAC) to the same cell lines.

DETAILED DESCRIPTION OF THE INVENTION

Figure 1:
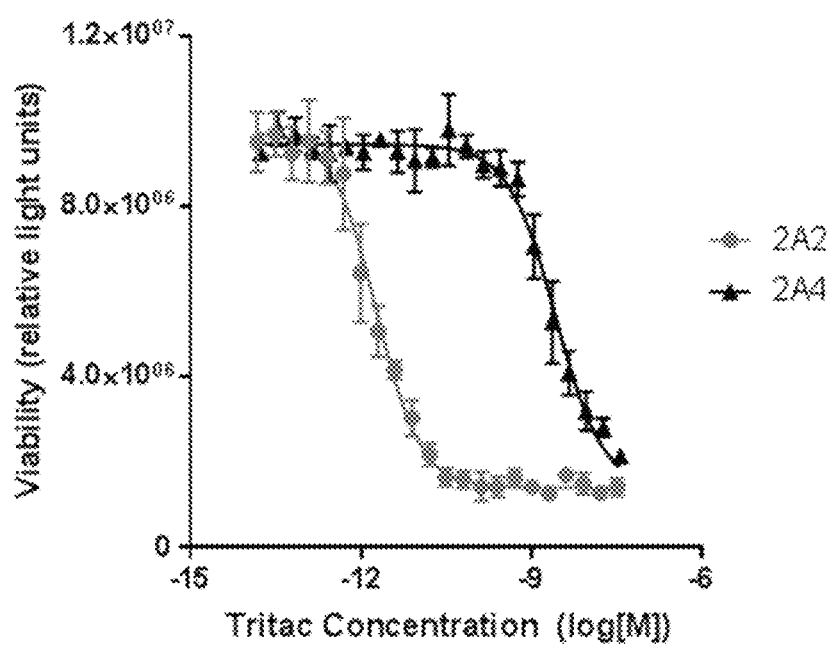
FIG. 1 illustrates the effectivity of exemplary MSLN targeting trispecific molecules (2A2 and 2A4), containing an anti-MSLN binding protein according to the present disclosure, in killing of OVCAR8 cells that expresses the target protein MSLN.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby

Certain Definitions

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the given value. Where particular values are described in the application and claims, unless otherwise stated the term "about" should be assumed to mean an acceptable error range for the particular value.

The terms "individual," "patient," or "subject" are used interchangeably. None of the terms require or are limited to situation characterized by the supervision (e.g. constant or intermittent) of a health care worker (e.g. a doctor, a registered nurse, a nurse practitioner, a physician's assistant, an orderly, or a hospice worker).

The term "Framework" or "FR" residues (or regions) refer to variable domain residues other than the CDR or hypervariable region residues as herein defined. A "human consensus framework" is a framework which represents the most commonly occurring amino acid residue in a selection of human immunoglobulin VL or VH framework sequences.

As used herein, "Variable region" or "variable domain" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity. "Variable domain residue numbering as in Kabat" or "amino acid position numbering as in Kabat," and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g., residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence. It is not intended that CDRs of the present disclosure necessarily correspond to the Kabat numbering convention.

As used herein, the term "Percent (%) amino acid sequence identity" with respect to a sequence is defined as the percentage of amino acid residues in a candidate sequence that are identical with the amino acid residues in the specific sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer softwares such as EMBOSS MATCHER, EMBOSS WATER, EMBOSS STRETCHER, EMBOSS NEEDLE, EMBOSS LALIGN, BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

As used herein, "elimination half-time" is used in its ordinary sense, as is described in *Goodman and Gillman's The Pharmaceutical Basis of Therapeutics* 21-25 (Alfred Goodman Gilman, Louis S. Goodman, and Alfred Gilman, eds., 6th ed. 1980). Briefly, the term is meant to encompass a quantitative measure of the time course of drug elimination. The elimination of most drugs is exponential (i.e., follows first-order kinetics), since drug concentrations usually do not approach those required for saturation of the elimination process. The rate of an exponential process may be expressed by its rate constant, k, which expresses the fractional change per unit of time, or by its half-time, $t_{1/2}$ the time required for 50% completion of the process. The units of these two constants are time$^{-1}$ and time, respectively. A first-order rate constant and the half-time of the reaction are simply related ($k \times t_{1/2} = 0.693$) and may be interchanged accordingly. Since first-order elimination kinetics dictates that a constant fraction of drug is lost per unit time, a plot of the log of drug concentration versus time is linear at all times following the initial distribution phase (i.e. after drug absorption and distribution are complete). The half-time for drug elimination can be accurately determined from such a graph.

As used herein, the term "binding affinity" refers to the affinity of the proteins described in the disclosure to their binding targets, and is expressed numerically using "Kd" values. If two or more proteins are indicated to have comparable binding affinities towards their binding targets, then the Kd values for binding of the respective proteins towards their binding targets, are within ±2-fold of each other. If two or more proteins are indicated to have comparable binding affinities towards single binding target, then the Kd values for binding of the respective proteins towards said single binding target, are within ±2-fold of each other. If a protein is indicated to bind two or more targets with comparable binding affinities, then the Kd values for binding of said protein to the two or more targets are within ±2-fold of each other. In general, a higher Kd value corresponds to a weaker binding. In some embodiments, the "Kd" is measured by a radiolabeled antigen binding assay (RIA) or surface plasmon resonance assays using a BIAcore™-2000 or a BIAcore™-3000 (BIAcore, Inc., Piscataway, N.J.). In certain embodiments, an "on-rate" or "rate of association" or "association rate" or "kon" and an "off-rate" or "rate of dissociation" or "dissociation rate" or "koff" are also determined with the surface plasmon resonance technique using a BIAcore™-2000 or a BIAcore™-3000 (BIAcore, Inc., Piscataway, N.J.). In additional embodiments, the "Kd", "kon", and "koff" are measured using the OCTET® Systems (Pall Life Sciences). In an exemplary method for measuring binding affinity using the OCTET® Systems, the ligand, e.g., biotinylated human or cynomolgus MSLN, is immobilized on the OCTET® streptavidin capillary sensor tip surface which streptavidin tips are then activated according to manufacturer's instructions using about 20-50 µg/ml human or cynomolgus MSLN protein. A solution of PBS/Casein is also introduced as a blocking agent. For association kinetic measurements, MSLN binding protein variants are introduced at a concentration ranging from about 10 ng/mL to about 100 µg/mL, about 50 ng/mL to about 5 µg/mL, or about 2 ng/mL to about 20 µg/mL. In some embodiments, the MSLN binding single domain proteins are used at a concentration ranging from about 2 ng/mL to about 20 µg/mL. Complete dissociation is observed in case of the negative control, assay buffer without the binding proteins. The kinetic parameters of the binding reactions are then determined using an appropriate tool, e.g., ForteBio software.

Described herein are MSLN binding proteins, pharmaceutical compositions as well as nucleic acids, recombinant expression vectors, and host cells for making such MSLN binding proteins. Also provided are methods of using the disclosed MSLN binding proteins in the prevention, and/or treatment of diseases, conditions and disorders. The MSLN binding proteins are capable specifically binding to MSLN. In some embodiments, the MSLN binding proteins include additional domains, such as a CD3 binding domain and an albumin binding domain.

Mesothelin (MSLN) and its Role in Tumorous Diseases

Contemplated herein are mesothelin binding proteins. Mesothelin is a glycoprotein present on the surface of cells of the mesothelial lining of the peritoneal, pleural and pericardial body cavities. The mesothelin gene (MSLN) encodes a 71-kilodalton (kDa) precursor protein that is processed to a 40-kDa protein termed mesothelin, which is a glycosyl-phosphatidylinositol-anchored glycoprotein present on the cell surface (Chang, et al, Proc Natl Acad Sci USA (1996) 93:136-40). The mesothelin cDNA was cloned from a library prepared from the HPC-Y5 cell line (Kojima et al. (1995) J. Biol. Chem. 270:21984-21990). The cDNA also was cloned using the monoclonal antibody K1, which recognizes mesotheliomas (Chang and Pastan (1996) Proc. Natl. Acad. Sci. USA 93:136-40). Mesothelin is a differentiation antigen whose expression in normal human tissues is limited to mesothelial cells lining the body cavity, such as the pleura, pericardium and peritoneum. Mesothelin is also highly expressed in several different human cancers, including mesotheliomas, pancreatic adenocarcinomas, ovarian cancers, stomach and lung adenocarcinomas. (Hassan, et al., Eur J Cancer (2008) 44:46-53) (Ordonez, Am J Surg Pathol (2003) 27:1418-28; Ho, et al., Clin Cancer Res (2007) 13:1571-5). Mesothelin is overexpressed in a vast majority of primary pancreatic adenocarcinomas with rare and weak expression seen in benign pancreatic tissue. Argani P, et al. Clin Cancer Res. 2001; 7(12):3862-3868. Epithelial malignant pleural mesothelioma (MPM) universally expresses mesothelin while sarcomatoid MPM likely does not express mesothelin. Most serous epithelial ovarian carcinomas, and the related primary peritoneal carcinomas, express mesothelin.

Mesothelin is also shed from tumor cells as a soluble form of the protein, as compared to the native membrane bound version (Hellstrom, et al., Cancer Epidemiol Biomarkers Prev (2006) 15:1014-20; Ho, et al., Cancer Epidemiol Biomarkers Prev (2006) 15:1751). Structurally, mesothelin is expressed on the cell surface as a 60 kDa precursor polypeptide, which is proteolytically processed into a 31 kDa shed component (corresponding to MPF) and a 40 kDa membrane bound component (Hassan et al. (2004) Clin. Cancer. Res. 10:3937-3942). Mesothelin has been shown to interact with CA125 (also known as MUC-16), a mucin-like glycoprotein present on the surface of tumor cells that previously had been identified as an ovarian cancer antigen. Further, binding of CA125 to membrane-bound mesothelin mediates heterotypic cell adhesion and CA125 and mesothelin are co-expressed in advanced grade ovarian adenocarcinoma (Rump, A. et al. (2004) J. Biol. Chem. 279:9190-9198). Expression of mesothelin in the lining of the peritoneum correlates with the preferred site of metastasis formation of ovarian cancer and mesothelin-CA125 binding is thought to facilitate peritoneal metastasis of ovarian tumors (Gubbels, J. A. et al. (2006) Mol. Cancer. 5:50).

Mesothelin is a target of a natural immune response in ovarian cancer, and has been proposed to be a target for cancer immunotherapy. Bracci L, et al. Clin Cancer Res. 2007; 13(2 Pt 1):644-653; Moschella F, et al. Cancer Res. 2011; 71(10):3528-3539; Gross G, et al. FASEB J. 1992; 6(15):3370-3378; Sadelain M, et al. Nat Rev Cancer. 2003; 3(1):35-45; Muul L M, et al. Blood. 2003; 101(7):2563-2569; Yee C, et al. Proc Natl Acad Sci USA. 2002; 99(25):16168-16173. The presence of mesothelin-specific CTLs in patients with pancreatic cancer correlates with overall survival. Thomas A M, et al. J Exp Med. 2004; 200:297-306. In addition, Pastan and coworkers have used soluble antibody fragments of an anti-mesothelin antibody conjugated to immunotoxins to treat cancer patients with mesothelin-positive tumors. This approach has demonstrated adequate safety and some clinical activity in pancreatic cancer. Hassan R, et al. Cancer Immun. 2007; 7:20 and Hassan R, et al. Clin Cancer Res. 2007; 13(17):5144-5149. In ovarian cancer, this therapeutic strategy produced one minor response by RECIST criteria and stable disease in a second patient who also had complete resolution of their ascites.

Mesothelin can also be used a marker for diagnosis and prognosis of certain types of cancer because trace amounts of mesothelin can be detected in the blood of some patients with mesothelin-positive cancers (Cristaudo et al., Clin. Cancer Res. 13:5076-5081, 2007). It has been reported that mesothelin may be released into serum through deletion at its carboxyl terminus or by proteolytic cleavage from its membrane bound form (Hassan et al., Clin. Cancer Res. 10:3937-3942, 2004). An increase in the soluble form of mesothelin was detectable several years before malignant mesotheliomas occurred among workers exposed to asbestos (Creaney and Robinson, Hematol. Oncol. Clin. North Am. 19:1025-1040, 2005). Furthermore, patients with ovarian, pancreatic, and lung cancers also have elevated soluble mesothelin in serum (Cristaudo et al., Clin. Cancer Res. 13:5076-5081, 2007; Hassan et al., Clin. Cancer Res. 12:447-453, 2006; Croso et al., Cancer Detect. Prev. 30:180-187, 2006). Accordingly, mesothelin is an appropriate target for methods of disease prevention or treatment and there is a need for effective antibodies specific for mesothelin.

It has been shown that cell surface mature mesothelin comprises three distinct domains, namely Regions I (comprising residues 296-390), II (comprising residues 391-486), and III (comprising residue 487-598). (Tang et al., A human single-domain antibody elicits potent antitumor activity by targeting an epitope in mesothelin close to the cancer cell surface, Mol. Can. Therapeutics, 12(4): 416-426, 2013).

The first antibodies generated against mesothelin for therapeutic intervention were designed to interfere with the interaction between mesothelin and CA-125. Phage display identified the Fv SS, which was affinity optimized and used to generate a recombinant immunotoxin targeting mesothelin, SS1P. The MORAb-009 antibody amatuximab, which also uses SS1, recognizes a non-linear epitope in the amino terminal 64 amino acids of mesothelin, within region I. The SS1 Fv was also used to generate chimeric antigen receptor-engineered T cells. Recently, new anti-mesothelin antibodies have been reported that recognize other regions of the mesothelin protein.

There is still a need for having available further options for the treatment of solid tumor diseases related to the overexpression of mesothelin, such as ovarian cancer, pancreatic cancer, mesothelioma, lung cancer, gastric cancer and triple negative breast cancer. The present disclosure provides, in certain embodiments, single domain proteins which specifically bind to MSLN on the surface of tumor target cells.

MSLN Binding Proteins

Provided herein in certain embodiments are binding proteins, such as anti-MSLN single domain antibodies or antibody variants, which bind to an epitope in the MSLN protein. In some embodiments, the MSLN binding protein binds to a protein comprising the sequence of SEQ ID NO: 57. In some embodiments, the MSLN binding protein binds to a protein comprising a truncated sequence compared to SEQ ID NO: 57.

In some embodiments, the MSLN binding proteins disclosed herein recognize full-length mesothelin. In certain instances, the MSLN binding proteins disclosed herein recognize an epitope in region I (comprising amino acid residues 296-390 of SEQ ID NO: 57), region II (comprising amino acid residue 391-486 of SEQ ID NO: 57), or region III (comprising amino acid residues 487-598 of SEQ ID NO: 57) of mesothelin. It is contemplated that the MSLN binding proteins of the present disclosure may, in some embodiments, recognize and bind to epitopes that are located outside regions I, II, or III of mesothelin. In yet other embodiments are disclosed MSLN binding proteins that recognize and bind to an epitope different than the MORAb-009 antibody.

In some embodiments, the MSLN binding proteins of the present disclosure are expressed within a multidomain protein that includes additional immunoglobulin domains. Such multidomain proteins can act via immunotoxin-based inhibition of tumor growth and induction of antibody-dependent cellular cytotoxicity (ADCC). In some embodiments, the multidomain proteins containing the MSLN binding proteins of the present disclosure exhibit complement-dependent cytotoxicity (CDC) activity. In some embodiments, the multidomain proteins containing the MSLN binding proteins of the present disclosure exhibit both ADCC and CDC activity, against cancer cells expressing mesothelin.

Furthermore, in some embodiments, where multidomain proteins containing the MSLN binding proteins act via CDC, the MLSN binding protein may recognize a conformational epitope at the C-terminal end of mesothelin protein, close to the cell surface. In some embodiments, the mesothelin protein comprises the sequence as set forth in SEQ ID NO: 57, and the C-terminal end comprises the amino acid residues 539-588.

In some embodiments, the MSLN binding protein is an anti-MSLN antibody or an antibody variant. As used herein, the term "antibody variant" refers to variants and derivatives of an antibody described herein. In certain embodiments, amino acid sequence variants of the anti-MSLN antibodies described herein are contemplated. For example, in certain embodiments amino acid sequence variants of anti-MSLN antibodies described herein are contemplated to improve the binding affinity and/or other biological properties of the antibodies. Exemplary method for preparing amino acid variants include, but are not limited to, introducing appropriate modifications into the nucleotide sequence encoding the antibody, or by peptide synthesis. Such modifications include, for example, deletions from, and/or insertions into and/or substitutions of residues within the amino acid sequences of the antibody.

Any combination of deletion, insertion, and substitution can be made to arrive at the final construct, provided that the final construct possesses the desired characteristics, e.g., antigen-binding. In certain embodiments, antibody variants having one or more amino acid substitutions are provided. Sites of interest for substitution mutagenesis include the CDRs and framework regions. Examples of such substitutions are described below. Amino acid substitutions may be introduced into an antibody of interest and the products screened for a desired activity, e.g., retained/improved antigen binding, decreased immunogenicity, or improved antibody-dependent cell mediated cytotoxicity (ADCC) or complement dependent cytotoxicity (CDC). Both conservative and non-conservative amino acid substitutions are contemplated for preparing the antibody variants.

In another example of a substitution to create a variant anti-MSLN antibody, one or more hypervariable region residues of a parent antibody are substituted. In general, variants are then selected based on improvements in desired properties compared to a parent antibody, for example, increased affinity, reduced affinity, reduced immunogenicity, increased pH dependence of binding. For example, an affinity matured variant antibody can be generated, e.g., using phage display-based affinity maturation techniques such as those described herein and known in the field.

In some embodiments, the MSLN binding protein described herein is a single domain antibody such as a heavy chain variable domain (VH), a variable domain (VHH) of llama derived sdAb, peptide, ligand or a small molecule entity specific for mesothelin. In some embodiments, the mesothelin binding domain of the MSLN binding protein described herein is any domain that binds to mesothelin including but not limited to domains from a monoclonal antibody, a polyclonal antibody, a recombinant antibody, a human antibody, a humanized antibody. In certain embodiments, the MSLN binding protein is a single-domain antibody. In other embodiments, the MSLN binding protein is a peptide. In further embodiments, the MSLN binding protein is a small molecule.

Generally, it should be noted that the term single domain antibody as used herein in its broadest sense is not limited to a specific biological source or to a specific method of preparation. Single domain antibodies are antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, goat, rabbit, bovine. For example, in some embodiments, the single domain antibodies of the disclosure are obtained: (1) by isolating the VHH domain of a naturally occurring heavy chain antibody; (2) by expression of a nucleotide sequence encoding a naturally occurring VHH domain; (3) by "humanization" of a naturally occurring VHH domain or by expression of a nucleic acid encoding a such humanized VHH domain; (4) by "camelization" of a naturally occurring VH domain from any animal species, and in particular from a species of mammal, such as from a human being, or by expression of a nucleic acid encoding such a camelized VH domain; (5) by "camelisation" of a "domain antibody" or "Dab", or by expression of a nucleic acid encoding such a camelized VH domain; (6) by using synthetic or semi-synthetic techniques for preparing proteins, polypeptides or other amino acid sequences; (7) by preparing a nucleic acid encoding a single domain antibody using techniques for nucleic acid synthesis known in the field, followed by expression of the nucleic acid thus obtained; and/or (8) by any combination of one or more of the foregoing.

In one embodiment, a single domain antibody corresponds to the VHH domains of naturally occurring heavy chain antibodies directed against MSLN. As further described herein, such VHH sequences can generally be generated or obtained by suitably immunizing a species of Llama with MSLN, (i.e., so as to raise an immune response and/or heavy chain antibodies directed against MSLN), by obtaining a suitable biological sample from said Llama (such as a blood sample, serum sample or sample of B-cells), and by generating VHH sequences directed against MSLN, starting from said sample, using any suitable technique known in the field.

In another embodiment, such naturally occurring VHH domains against MSLN, are obtained from naïve libraries of Camelid VHH sequences, for example by screening such a library using MSLN, or at least one part, fragment, antigenic determinant or epitope thereof using one or more screening techniques known in the field. Such libraries and techniques are for example described in WO 99/37681, WO 01/90190, WO 03/025020 and WO 03/035694. Alternatively, improved synthetic or semi-synthetic libraries derived from naïve VHH libraries are used, such as VHH libraries obtained from naïve VHH libraries by techniques such as random mutagenesis and/or CDR shuffling, as for example described in WO 00/43507.

In a further embodiment, yet another technique for obtaining VHH sequences directed against MSLN, involves suitably immunizing a transgenic mammal that is capable of expressing heavy chain antibodies (i.e., so as to raise an immune response and/or heavy chain antibodies directed against MSLN), obtaining a suitable biological sample from said transgenic mammal (such as a blood sample, serum sample or sample of B-cells), and then generating VHH sequences directed against MSLN, starting from said sample, using any suitable technique known in the field. For example, for this purpose, the heavy chain antibody-expressing rats or mice and the further methods and techniques described in WO 02/085945 and in WO 04/049794 can be used.

In some embodiments, an anti-MSLN antibody, as described herein comprises single domain antibody with an amino acid sequence that corresponds to the amino acid sequence of a naturally occurring VHH domain, but that has been "humanized", i.e., by replacing one or more amino acid residues in the amino acid sequence of said naturally occurring VHH sequence (and in particular in the framework sequences) by one or more of the amino acid residues that occur at the corresponding position(s) in a VH domain from a conventional 4-chain antibody from a human being (e.g., as indicated above). This can be performed in a manner known in the field, which will be clear to the skilled person, for example on the basis of the further description herein. Again, it should be noted that such humanized anti-MSLN single domain antibodies of the disclosure are obtained in any suitable manner known per se (i.e., as indicated under points (1)-(8) above) and thus are not strictly limited to polypeptides that have been obtained using a polypeptide that comprises a naturally occurring VHH domain as a starting material. In some additional embodiments, a single domain MSLN antibody, as described herein, comprises a single domain antibody with an amino acid sequence that corresponds to the amino acid sequence of a naturally occurring VH domain, but that has been "camelized", i.e., by replacing one or more amino acid residues in the amino acid sequence of a naturally occurring VH domain from a conventional 4-chain antibody by one or more of the amino acid residues that occur at the corresponding position(s) in a VHH domain of a heavy chain antibody. Such "camelizing" substitutions are preferably inserted at amino acid positions that form and/or are present at the VH-VL interface, and/or at the so-called Camelidae hallmark residues (see for example WO 94/04678 and Davies and Riechmann (1994 and 1996)). Preferably, the VH sequence that is used as a starting material or starting point for generating or designing the camelized single domain is preferably a VH sequence from a mammal, more preferably the VH sequence of a human being, such as a VH3 sequence. However, it should be noted that such camelized anti-MSLN single domain antibodies of the disclosure, in certain embodiments, is obtained in any suitable manner known in the field (i.e., as indicated under points (1)-(8) above) and thus are not strictly limited to polypeptides that have been obtained using a polypeptide that comprises a naturally occurring VH domain as a starting material. For example, as further described herein, both "humanization" and "camelization" is performed by providing a nucleotide sequence that encodes a naturally occurring VHH domain or VH domain, respectively, and then changing, one or more codons in said nucleotide sequence in such a way that the new nucleotide sequence encodes a "humanized" or "camelized" single domain antibody, respectively. This nucleic acid can then be expressed, so as to provide the desired anti-MSLN single domain antibody of the disclosure. Alternatively, in other embodiments, based on the amino acid sequence of a naturally occurring VHH domain or VH domain, respectively, the amino acid sequence of the desired humanized or camelized anti-MSLN single domain antibody of the disclosure, respectively, are designed and then synthesized de novo using known techniques for peptide synthesis. In some embodiments, based on the amino acid sequence or nucleotide sequence of a naturally occurring VHH domain or VH domain, respectively, a nucleotide sequence encoding the desired humanized or camelized anti-MSLN single domain antibody of the disclosure, respectively, is designed and then synthesized de novo using known techniques for nucleic acid synthesis, after which the nucleic acid thus obtained is expressed in using known expression techniques, so as to provide the desired anti-MSLN single domain antibody of the disclosure.

Other suitable methods and techniques for obtaining the anti-MSLN single domain antibody of the disclosure and/or nucleic acids encoding the same, starting from naturally occurring VH sequences or VHH sequences for example comprises combining one or more parts of one or more naturally occurring VH sequences (such as one or more framework (FR) sequences and/or complementarity determining region (CDR) sequences), one or more parts of one or more naturally occurring VHH sequences (such as one or more FR sequences or CDR sequences), and/or one or more synthetic or semi-synthetic sequences, in a suitable manner, so as to provide an anti-MSLN single domain antibody of the disclosure or a nucleotide sequence or nucleic acid encoding the same.

It is contemplated that in some embodiments the MSLN binding protein is fairly small and no more than 25 kD, no more than 20 kD, no more than 15 kD, or no more than 10 kD in some embodiments. In certain instances, the MSLN binding protein is 5 kD or less if it is a peptide or small molecule entity.

In some embodiments, the MSLN binding protein is an anti-MSLN specific antibody comprising a heavy chain variable complementarity determining region CDR1, a heavy chain variable CDR2, a heavy chain variable CDR3, a light chain variable CDR1, a light chain variable CDR2, and a light chain variable CDR3. In some embodiments, the MSLN binding protein comprises any domain that binds to MSLN including but not limited to domains from a monoclonal antibody, a polyclonal antibody, a recombinant antibody, a human antibody, a humanized antibody, or antigen binding fragments such as single domain antibodies (sdAb), Fab, Fab', F(ab)2, and Fv fragments, fragments comprised of one or more CDRs, single-chain antibodies (e.g., single chain Fv fragments (scFv)), disulfide stabilized (dsFv) Fv fragments, heteroconjugate antibodies (e.g., bispecific antibodies), pFv fragments, heavy chain monomers or dimers, light chain monomers or dimers, and dimers consisting of one heavy chain and one light chain. In some embodiments, the MSLN binding protein is a single domain antibody. In some embodiments, the anti-MSLN single domain antibody comprises heavy chain variable complementarity determining regions (CDR), CDR1, CDR2, and CDR3.

In some embodiments, the MSLN binding protein of the present disclosure is a polypeptide comprising an amino acid sequence that is comprised of four framework regions/sequences (f1-f4) interrupted by three complementarity determining regions/sequences, as represented by the formula: f1-r1-f2-r2-f3-r3-f4, wherein r1, r2, and r3 are complementarity determining regions CDR1, CDR2, and CDR3, respectively, and f1, f2, f3, and f4 are framework residues. The framework residues of the MSLN binding protein of the present disclosure comprise, for example, 75, 76, 77, 78, 79, 80, 81, 82, 83, 84, 85, 86, 87, 88, 89, 90, 91, 92, 93, or 94 amino acid residues, and the complementarity determining regions comprise, for example, 24, 25, 26, 27, 28, 29, 30, 31, 32, 33, 34, 35, or 36 amino acid residues. In some embodiments, the MSLN binding protein comprises an amino acid sequence selected from SEQ ID NOs: 1-40.

In some embodiments, the CDR1 comprises the amino acid sequence as set forth in SEQ ID NO: 51 or a variant having one, two, three, four, five, six, seven, eight, nine, or ten amino acid substitutions in SEQ ID NO: 51. In some embodiments, the CDR2 comprises a sequence as set forth in SEQ ID NO: 52 or a variant having one, two, three, four, five, six, seven, eight, nine, or ten amino acid substitutions in SEQ ID NO: 52. In some embodiments, the CDR3 comprises a sequence as set forth in SEQ ID NO: 53 or a variant having one, two, three, four, five, six, seven, eight, nine, or ten amino acid substitutions in SEQ ID NO: 53.

In some embodiments, the CDR1 comprises the amino acid sequence as set forth in SEQ ID NO: 54 or a variant having one, two, three, four, five, six, seven, eight, nine, or ten amino acid substitutions in SEQ ID NO: 54. In some embodiments, the CDR2 comprises a sequence as set forth in SEQ ID NO: 55 or a variant having one, two, three, four, five, six, seven, eight, nine, or ten amino acid substitutions in SEQ ID NO: 55. In some embodiments, the CDR3 comprises a sequence as set forth in SEQ ID NO: 56 or a variant having one, two, three, four, five, six, seven, eight, nine, or ten amino acid substitutions in SEQ ID NO: 56.

The MSLN binding proteins of the present disclosure, in certain examples, comprise one or more conserved regions. The conserved regions comprise sequences as set forth in SEQ ID NOs: 41-50, or variants comprising one or more amino acid residue substitutions relative to said sequences. Exemplary embodiments include MSLN binding proteins comprising one or more conserved regions selected from SEQ ID NOs: 41-44, or variants comprising one or more amino acid residue substitutions relative to said sequences. In some cases, the MSLN binding protein comprises (i) a stretch of amino acids corresponding to SEQ ID NO: 41, (ii) a stretch of amino acids corresponding to SEQ ID NO: 42, iii) a stretch of amino acids corresponding to SEQ ID NO: 43, and (iv) a stretch of amino acids corresponding to SEQ ID NO: 44.

Further exemplary embodiments include MSLN binding proteins comprising one or more conserved regions selected from SEQ ID NOs: 45-50, or variants comprising one or more amino acid residue substitutions relative to said sequences. In some cases, the MSLN binding protein comprises (i) a stretch of amino acids corresponding to SEQ ID NO: 45, (ii) a stretch of amino acids corresponding to SEQ ID NO: 46, (iii) a stretch of amino acids corresponding to SEQ ID NO: 47, (iv) a stretch of amino acids corresponding to SEQ ID NO: 48, (v) a stretch of amino acid corresponding to SEQ ID NO: 49, and (vi) a stretch of amino acids corresponding to SEQ ID NO: 50.

In various embodiments, the MSLN binding protein of the present disclosure is at least about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to an amino acid sequence selected from SEQ ID NOs: 1-29, 58, and 60-62.

In various embodiments, the MSLN binding protein of the present disclosure is at least about 75%, about 76%, about 77%, about 78%, about 79%, about 80%, about 81%, about 82%, about 83%, about 84%, about 85%, about 86%, about 87%, about 88%, about 89%, about 90%, about 91%, about 92%/a, about 93%, about 94%, about 95%, about 96%, about 97%, about 98%, about 99%, or about 100% identical to an amino acid sequence selected from SEQ ID NOs: 30-40, 58, and 60-62.

In various embodiments, a complementarity determining region of the MSLN binding protein of the present disclosure is at least about 10%, about 20%, about 30%, about 40%, about 50%, about 60%, about 70%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to the amino acid sequence set forth in SEQ ID NO: 51, or SEQ ID NO: 54.

In various embodiments, a complementarity determining region of the MSLN binding protein of the present disclosure is at least about 10%, about 20%, about 30%, about 40%, about 50%, about 60%, about 70%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to the amino acid sequence set forth in SEQ ID NO: 52, or SEQ ID NO: 55.

In various embodiments, a complementarity determining region of the MSLN binding protein of the present disclosure is at least about 10%, about 20%, about 30%, about 40%, about 50%, about 60%, about 70%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to the amino acid sequence set forth in SEQ ID NO: 53, or SEQ ID NO: 56.

In various embodiments, a complementarity determining region 1 (CDR1) of the MSLN binding protein of the present disclosure is at least about 10%, about 20%, about 30%, about 40%, about 50%, about 60%, about 70%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to an amino acid sequence as set forth in any one of SEQ ID Nos.: 63-101.

In various embodiments, a complementarity determining region 2 (CDR2) of the MSLN binding protein of the present disclosure is at least about 10%, about 20%, about 30%, about 40%, about 50%, about 60%, about 70%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to an amino acid sequence as set forth in any one of SEQ ID Nos.: 102-140.

In various embodiments, a complementarity determining region 3 (CDR3) of the MSLN binding protein of the present disclosure is at least about 10%, about 20%, about 30%, about 40%, about 50%, about 60%, about 70%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to an amino acid sequence as set forth in any one of SEQ ID Nos.: 141-179.

In various embodiments, a framework region 1 (f1) of the MSLN binding protein of the present disclosure is at least about 10%, about 20%, about 30%, about 40%, about 50%, about 60%, about 70%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to an amino acid sequence as set forth in any one of SEQ ID Nos.: 180-218.

In various embodiments, a framework region 1 (f1) of the MSLN binding protein of the present disclosure is at least about 10%, about 20%, about 30%, about 40%, about 50%, about 60%, about 70%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to an amino acid sequence as set forth in any one of SEQ ID Nos.: 219-257.

In various embodiments, a framework region 2 (f2) of the MSLN binding protein of the present disclosure is at least about 10%, about 20%, about 30%, about 40%, about 50%, about 60%, about 70%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to an amino acid sequence as set forth in any one of SEQ ID Nos.: 258-296.

In various embodiments, a framework region 3 (f3) of the MSLN binding protein of the present disclosure is at least about 10%, about 20%, about 30%, about 40%, about 50%, about 60%, about 70%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%/a, about 98%, about 99%, or about 100% identical to an amino acid sequence as set forth in any one of SEQ ID Nos.: 297-335.

In some embodiments, the MSLN binding protein, according to any one of the above embodiments, is a single domain antibody comprising the sequence of SEQ ID NO: 1. In some embodiments, the MSLN binding protein, according to any one of the above embodiments, is a single domain antibody comprising the sequence of SEQ ID NO: 2. In some embodiments, the MSLN binding protein, according to any one of the above embodiments, is a single domain antibody comprising the sequence of SEQ ID NO: 3. In some embodiments, the MSLN binding protein, according to any one of the above embodiments, is a single domain antibody comprising the sequence of SEQ ID NO: 4. In some embodiments, the MSLN binding protein, according to any one of the above embodiments, is a single domain antibody comprising the sequence of SEQ ID NO: 5. In some embodiments, the MSLN binding protein, according to any one of the above embodiments, is a single domain antibody comprising the sequence of SEQ ID NO: 6. In some embodiments, the MSLN binding protein, according to any one of the above embodiments, is a single domain antibody comprising the sequence of SEQ ID NO: 7. In some embodiments, the MSLN binding protein, according to any one of the above embodiments, is a single domain antibody comprising the sequence of SEQ ID NO: 8. In some embodiments, the MSLN binding protein, according to any one of the above embodiments, is a single domain antibody comprising the sequence of SEQ ID NO: 9. In some embodiments, the MSLN binding protein, according to any one of the above embodiments, is a single domain antibody comprising the sequence of SEQ ID NO: 10. In some embodiments, the MSLN binding protein, according to any one of the above embodiments, is a single domain antibody comprising the sequence of SEQ ID NO: 11. In some embodiments, the MSLN binding protein, according to any one of the above embodiments, is a single domain antibody comprising the sequence of SEQ ID NO: 12. In some embodiments, the MSLN binding protein, according to any one of the above embodiments, is a single domain antibody comprising the sequence of SEQ ID NO: 13. In some embodiments, the MSLN binding protein, according to any one of the above embodiments, is a single domain antibody comprising the sequence of SEQ ID NO: 14. In some embodiments, the MSLN binding protein, according to any one of the above embodiments, is a single domain antibody comprising the sequence of SEQ ID NO: 15. In some embodiments, the MSLN binding protein, according to any one of the above embodiments, is a single domain antibody comprising the sequence of SEQ ID NO: 16. In some embodiments, the MSLN binding protein, according to any one of the above embodiments, is a single domain antibody comprising the sequence of SEQ ID NO: 17. In some embodiments, the MSLN binding protein, according to any one of the above embodiments, is a single domain antibody comprising the sequence of SEQ ID NO: 18. In some embodiments, the MSLN binding protein, according to any one of the above embodiments, is a single domain antibody comprising the sequence of SEQ ID NO: 19. In some embodiments, the MSLN binding protein, according to any one of the above embodiments, is a single domain antibody comprising the sequence of SEQ ID NO: 20. In some embodiments, the MSLN binding protein, according to any one of the above embodiments, is a single domain antibody comprising the sequence of SEQ ID NO: 21. In some embodiments, the MSLN binding protein, according to any one of the above embodiments, is a single domain antibody comprising the sequence of SEQ ID NO: 22. In some embodiments, the MSLN binding protein, according to any one of the above embodiments, is a single domain antibody comprising the sequence of SEQ ID NO: 23. In some embodiments, the MSLN binding protein, according to any one of the above embodiments, is a single domain antibody comprising the sequence of SEQ ID NO: 24. In some embodiments, the MSLN binding protein, according to any one of the above embodiments, is a single domain antibody comprising the sequence of SEQ ID NO: 25. In some embodiments, the MSLN binding protein, according to any one of the above embodiments, is a single domain antibody comprising the sequence of SEQ ID NO: 26. In some embodiments, the MSLN binding protein, according to any one of the above embodiments, is a single domain antibody comprising the sequence of SEQ ID NO: 27. In some embodiments, the MSLN binding protein, according to any one of the above embodiments, is a single domain antibody comprising the sequence of SEQ ID NO: 28. In some embodiments, the MSLN binding protein, according to any one of the above embodiments, is a single domain antibody comprising the sequence of SEQ ID NO: 28

In some embodiments, the MSLN binding protein, according to any one of the above embodiments, is a humanized single domain antibody comprising the sequence of SEQ ID NO: 30. In some embodiments, the MSLN binding protein, according to any one of the above embodiments, is a humanized single domain antibody comprising the sequence of SEQ ID NO: 31. In some embodiments, the MSLN binding protein, according to any one of the above embodiments, is a humanized single domain antibody comprising the sequence of SEQ ID NO: 32. In some embodiments, the MSLN binding protein, according to any one of the above embodiments, is a humanized single domain antibody comprising the sequence of SEQ ID NO: 33. In some embodiments, the MSLN binding protein, according to any one of the above embodiments, is a humanized single domain antibody comprising the sequence of SEQ ID NO: 34. In some embodiments, the MSLN binding protein, according to any one of the above embodiments, is a humanized single domain antibody comprising the sequence of SEQ ID NO: 35. In some embodiments, the MSLN binding protein, according to any one of the above embodiments, is a humanized single domain antibody comprising the sequence of SEQ ID NO: 36. In some embodiments, the MSLN binding protein, according to any one of the above embodiments, is a humanized single domain antibody comprising the sequence of SEQ ID NO: 37. In some embodiments, the MSLN binding protein, according to any one of the above embodiments, is a humanized single domain antibody comprising the sequence of SEQ ID NO: 38. In some embodiments, the MSLN binding protein, according to any one of the above embodiments, is a humanized single domain antibody comprising the sequence of SEQ ID NO: 39. In some embodiments, the MSLN binding protein, according to any one of the above embodiments, is a humanized single domain antibody comprising the sequence of SEQ ID NO: 40. In some embodiments, the MSLN binding protein, according to any one of the above embodiments, is a humanized single domain antibody comprising the sequence of SEQ ID NO: 58. In some embodiments, the MSLN binding protein, according to any one of the above embodiments, is a humanized single domain antibody comprising the sequence of SEQ ID NO: 60. In some embodiments, the MSLN binding protein, according to any one of the above embodiments, is a humanized single domain antibody comprising the sequence of SEQ ID NO: 61. In some embodiments, the MSLN binding protein, according to any one of the above embodiments, is a humanized single domain antibody comprising the sequence of SEQ ID NO: 62.

In some embodiments, the MSLN binding protein is cross-reactive with human and cynomolgus mesothelin. In some embodiments, the MSLN binding protein is specific for human mesothelin. In certain embodiments, the MSLN binding protein disclosed herein binds to human mesothelin with a human Kd (hKd). In certain embodiments, the MSLN binding protein disclosed herein binds to cynomolgus mesothelin with a cyno Kd (cKd). In certain embodiments, the MSLN binding protein disclosed herein binds to both cynomolgus mesothelin and a human mesothelin, with a cyno Kd (cKd) and a human Kd, respectively (hKd). In some embodiments, the MSLN binding protein binds to human and cynomolgus mesothelin with comparable binding affinities (i.e., hKd and cKd values do not differ by more than +10%). In some embodiments, the hKd and the cKd range from about 0.1 nM to about 500 nM. In some embodiments, the hKd and the cKd range from about 0.1 nM to about 450 nM. In some embodiments, the hKd and the cKd range from about 0.1 nM to about 400 nM. In some embodiments, the hKd and the cKd range from about 0.1 nM to about 350 nM. In some embodiments, the hKd and the cKd range from about 0.1 nM to about 300 nM. In some embodiments, the hKd and the cKd range from about 0.1 nM to about 250 nM. In some embodiments, the hKd and the cKd range from about 0.1 nM to about 200 nM. In some embodiments, the hKd and the cKd range from about 0.1 nM to about 150 nM. In some embodiments, the hKd and the cKd range from about 0.1 nM to about 100 nM. In some embodiments, the hKd and the cKd range from about 0.1 nM to about 90 nM. In some embodiments, the hKd and the cKd range from about 0.2 nM to about 80 nM. In some embodiments, the hKd and the cKd range from about 0.3 nM to about 70 nM. In some embodiments, the hKd and the cKd range from about 0.4 nM to about 50 nM. In some embodiments, the hKd and the cKd range from about 0.5 nM to about 30 nM. In some embodiments, the hKd and the cKd range from about 0.6 nM to about 10 nM. In some embodiments, the hKd and the cKd range from about 0.7 nM to about 8 nM. In some embodiments, the hKd and the cKd range from about 0.8 nM to about 6 nM. In some embodiments, the hKd and the cKd range from about 0.9 nM to about 4 nM. In some embodiments, the hKd and the cKd range from about 1 nM to about 2 nM.

In some embodiments, any of the foregoing MSLN binding proteins (e.g., anti-MSLN single domain antibodies of SEQ ID NOs: 1-40, and 58) are affinity peptide tagged for ease of purification. In some embodiments, the affinity peptide tag is six consecutive histidine residues, also referred to as 6x-his (SEQ ID NO: 336).

In certain embodiments, the MSLN binding proteins according to the present disclosure may be incorporated into MSLN targeting trispecific proteins. In some examples, the trispecific binding protein comprises a CD3 binding domain, a human serum albumin (HSA) binding domain and an anti-MSLN binding domain according to the present disclosure. In some instances, the trispecific binding protein comprises the domains described above in the following orientation: MSLN-HSA-CD3.

In certain embodiments, the MSLN binding proteins of the present disclosure preferentially bind membrane bound mesothelin over soluble mesothelin. Membrane bound mesothelin refers to the presence of mesothelin in or on the cell membrane surface of a cell that expresses mesothelin. Soluble mesothelin refers to mesothelin that is no longer on in or on the cell membrane surface of a cell that expresses or expressed mesothelin. In certain instances, the soluble mesothelin is present in the blood and/or lymphatic circulation in a subject. In one embodiment, the MSLN binding proteins bind membrane-bound mesothelin at least 5 fold, 10 fold, 15 fold, 20 fold, 25 fold, 30 fold, 40 fold, 50 fold, 100 fold, 500 fold, or 1000 fold greater than soluble mesothelin. In one embodiment, the antigen binding proteins of the present disclosure preferentially bind membrane-bound mesothelin 30 fold greater than soluble mesothelin. Determining the preferential binding of an antigen binding protein to membrane bound MSLN over soluble MSLN can be readily determined using assays well known in the art.

Integration into Chimeric Antigen Receptors (CAR)

The MSLN binding proteins of the present disclosure, e.g., an anti-MSLN single domain antibody, can, in certain examples, be incorporated into a chimeric antigen receptor (CAR). An engineered immune effector cell, e.g., a T cell or NK cell, can be used to express a CAR that includes an anti-MSLN single domain antibody as described herein. In one embodiments, the CAR including an anti-MSLN single domain antibody as described herein is connected to a transmembrane domain via a hinge region, and further a costimulatory domain, e.g., a functional signaling domain obtained from OX40, CD27, CD28, CD5, ICAM-1, LFA-1 (CD11a/CD18), ICOS (CD278), or 4-1BB. In some embodiments, the CAR further comprises a sequence encoding a intracellular signaling domain, such as 4-1BB and/or CD3 zeta.

Tumor Growth Reduction Properties

In certain embodiments, the MSLN binding proteins of the disclosure reduces the growth of tumor cells in vivo when administered to a subject who has tumor cells that express mesothelin. Measurement of the reduction of the growth of tumor cells can be determined by multiple different methodologies well known in the art. Nonlimiting examples include direct measurement of tumor dimension, measurement of excised tumor mass and comparison to control subjects, measurement via imaging techniques (e.g., CT or MRI) that may or may not use isotopes or luminescent molecules (e.g., luciferase) for enhanced analysis, and the like. In specific embodiments, administration of the antigen binding agents of the disclosure results in a reduction of in vivo growth of tumor cells as compared to a control antigen binding agent by at least about 10%, 20%, 30%, 40%, 50%, 60%, 70%, 80%, 90% or 100%, with an about 100% reduction in tumor growth indicating a complete response and disappearance of the tumor. In further embodiments, administration of the antigen binding agents of the disclosure results in a reduction of in vivo growth of tumor cells as compared to a control antigen binding agent by about 50-100%, about 75-100% or about 90-100%. In further embodiments, administration of the antigen binding agents of the disclosure results in a reduction of in vivo growth of tumor cells as compared to a control antigen binding agent by about 50-60%, about 60-70%, about 70-80%, about 80-90%, or about 90-100%.

MSLN Binding Protein Modifications

The MSLN binding proteins described herein encompass derivatives or analogs in which (i) an amino acid is substituted with an amino acid residue that is not one encoded by the genetic code, (ii) the mature polypeptide is fused with another compound such as polyethylene glycol, or (iii) additional amino acids are fused to the protein, such as a leader or secretory sequence or a sequence to block an immunogenic domain and/or for purification of the protein.

Typical modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristylation, oxidation, proteolytic processing, phosphorylation, prenylation, racemization, selenoylation, sulfation, transfer-RNA mediated addition of amino acids to proteins such as arginylation, and ubiquitination.

Modifications are made anywhere in the MSLN binding proteins described herein, including the peptide backbone, the amino acid side-chains, and the amino or carboxyl termini. Certain common peptide modifications that are useful for modification of MSLN binding proteins include glycosylation, lipid attachment, sulfation, gamma-carboxylation of glutamic acid residues, hydroxylation, blockage of the amino or carboxyl group in a polypeptide, or both, by a covalent modification, and ADP-ribosylation.

Polynucleotides Encoding MSLN Binding Proteins

Also provided, in some embodiments, are polynucleotide molecules encoding a MSLN binding protein as described herein. In some embodiments, the polynucleotide molecules are provided as DNA constructs. In other embodiments, the polynucleotide molecules are provided as messenger RNA transcripts.

The polynucleotide molecules are constructed by known methods such as by combining the genes encoding the anti-MSLN binding protein, operably linked to a suitable promoter, and optionally a suitable transcription terminator, and expressing it in bacteria or other appropriate expression system such as, for example CHO cells.

In some embodiments, the polynucleotide is inserted into a vector, preferably an expression vector, which represents a further embodiment. This recombinant vector can be constructed according to known methods. Vectors of particular interest include plasmids, phagemids, phage derivatives, virii (e.g., retroviruses, adenoviruses, adeno-associated viruses, herpes viruses, lentiviruses, and the like), and cosmids.

A variety of expression vector/host systems may be utilized to contain and express the polynucleotide encoding the polypeptide of the described MSLN binding protein. Examples of expression vectors for expression in *E. coli* are pSKK (Le Gall et al., J Immunol Methods. (2004) 285(1): 111-27), pcDNA5 (Invitrogen) for expression in mammalian cells, PICHIAPINK™ Yeast Expression Systems (Invitrogen), BACUVANCE™ Baculovirus Expression System (GenScript).

Thus, the MSLN binding proteins as described herein, in some embodiments, are produced by introducing a vector encoding the protein as described above into a host cell and culturing said host cell under conditions whereby the protein domains are expressed, may be isolated and, optionally, further purified.

Pharmaceutical Compositions

Also provided, in some embodiments, are pharmaceutical compositions comprising a MSLN binding protein described herein, a vector comprising the polynucleotide encoding the polypeptide of the MSLN binding proteins or a host cell transformed by this vector and at least one pharmaceutically acceptable carrier. The term "pharmaceutically acceptable carrier" includes, but is not limited to, any carrier that does not interfere with the effectiveness of the biological activity of the ingredients and that is not toxic to the patient to whom it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at a suitable dose. Preferably, the compositions are sterile. These compositions may also contain adjuvants such as preservative, emulsifying agents and dispersing agents. Prevention of the action of microorganisms may be ensured by the inclusion of various antibacterial and antifungal agents. A further embodiment provides one or more of the above described binding proteins, such as anti-MSLN single domain antibodies or antigen-binding fragments thereof packaged in lyophilized form, or packaged in an aqueous medium.

In some embodiments of the pharmaceutical compositions, the MSLN binding protein described herein is encapsulated in nanoparticles. In some embodiments, the nanoparticles are fullerenes, liquid crystals, liposome, quantum dots, superparamagnetic nanoparticles, dendrimers, or nanorods. In other embodiments of the pharmaceutical compositions, the MSLN binding protein is attached to liposomes. In some instances, the MSLN binding protein is conjugated to the surface of liposomes. In some instances, the MSLN binding protein is encapsulated within the shell of a liposome. In some instances, the liposome is a cationic liposome.

The MSLN binding proteins described herein are contemplated for use as a medicament. Administration is effected by different ways, e.g., by intravenous, intraperitoneal, subcutaneous, intramuscular, topical or intradermal administration. In some embodiments, the route of administration depends on the kind of therapy and the kind of compound contained in the pharmaceutical composition. The dosage regimen will be determined by the attending physician and other clinical factors. Dosages for any one patient depends on many factors, including the patient's size, body surface area, age, sex, the particular compound to be administered, time and route of administration, the kind of therapy, general health and other drugs being administered concurrently. An "effective dose" refers to amounts of the active ingredient that are sufficient to affect the course and the severity of the disease, leading to the reduction or remission of such pathology and may be determined using known methods.

In some embodiments, the MSLN binders of this disclosure are administered at a dosage of up to 10 mg/kg at a frequency of once a week. In some cases, the dosage ranges from about 1 ng/kg to about 10 mg/kg. In some embodiments, the dose is from about 1 ng/kg to about 10 ng/kg, about 5 ng/kg to about 15 ng/kg, about 12 ng/kg to about 20 ng/kg, about 18 ng/kg to about 30 ng/kg, about 25 ng/kg to about 50 ng/kg, about 35 ng/kg to about 60 ng/kg, about 45 ng/kg to about 70 ng/kg, about 65 ng/kg to about 85 ng/kg, about 80 ng/kg to about 1 µg/kg, about 0.5 µg/kg to about 5 µg/kg, about 2 µg/kg to about 10 µg/kg, about 7 µg/kg to about 15 µg/kg, about 12 µg/kg to about 25 µg/kg, about 20 µg/kg to about 50 µg/kg, about 35 µg/kg to about 70 µg/kg, about 45 µg/kg to about 80 µg/kg, about 65 µg/kg to about 90 µg/kg, about 85 µg/kg to about 0.1 mg/kg, about 0.095 mg/kg to about 10 mg/kg. In some cases, the dosage is about 0.1 mg/kg to about 0.2 mg/kg; about 0.25 mg/kg to about 0.5 mg/kg, about 0.45 mg/kg to about 1 mg/kg, about 0.75 mg/kg to about 3 mg/kg, about 2.5 mg/kg to about 4 mg/kg, about 3.5 mg/kg to about 5 mg/kg, about 4.5 mg/kg to about 6 mg/kg, about 5.5 mg/kg to about 7 mg/kg, about 6.5 mg/kg to about 8 mg/kg, about 7.5 mg/kg to about 9 mg/kg, or about 8.5 mg/kg to about 10 mg/kg. The frequency of administration, in some embodiments, is about less than daily, every other day, less than once a day, twice a week, weekly, once in 7 days, once in two weeks, once in two weeks, once in three weeks, once in four weeks, or once a month. In some cases, the frequency of administration is weekly. In some cases, the frequency of administration is weekly and the dosage is up to 10 mg/kg. In some cases, duration of administration is from about 1 day to about 4 weeks or longer.

Methods of Treatment

Also provided herein, in some embodiments, are methods and uses for stimulating the immune system of an individual in need thereof comprising administration of a MSLN binding protein as described herein. In some instances, the administration of a MSLN binding protein described herein induces and/or sustains cytotoxicity towards a cell expressing a target antigen. In some instances, the cell expressing a target antigen is a cancer or tumor cell, a virally infected cell, a bacterially infected cell, an autoreactive T or B cell, damaged red blood cells, arterial plaques, or fibrotic tissue.

Also provided herein are methods and uses for a treatment of a disease, disorder or condition associated with a target antigen comprising administering to an individual in need thereof a MSLN binding protein or a multispecific binding protein comprising the MSLN binding protein described herein. Diseases, disorders or conditions associated with a target antigen include, but are not limited to, viral infection, bacterial infection, auto-immune disease, transplant rejection, atherosclerosis, or fibrosis. In other embodiments, the disease, disorder or condition associated with a target antigen is a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease. In one embodiment, the disease, disorder or condition associated with a target antigen is cancer. Cancers that can be treated, prevented, or managed by the MSLN binding proteins of the present disclosure, and methods of using them, include but are not limited to cancers of an epithelial cell origin. Examples of such cancers include the following: leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to ductal carcinoma, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, non-seminoma, embryonal carcinoma, teratoma carcinoma, choriocarcinoma (yolk-sac tumor), prostate cancers such as but not limited to, prostatic intraepithelial neoplasia, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

The MSLN binding proteins of the disclosure are also useful in the treatment or prevention of a variety of cancers or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Burkitt's lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xeroderma pigmentosum, keratoactanthoma, seminoma, thyroid follicular cancer and teratocarcinoma. It is also contemplated that cancers caused by aberrations in apoptosis would also be treated by the methods and compositions of the disclosure. Such cancers may include but not be limited to follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented in the skin, lung, colon, breast, prostate, bladder, kidney, pancreas, ovary, or uterus. In other specific embodiments, sarcoma, melanoma, or leukemia is treated or prevented.

As used herein, in some embodiments, "treatment" or "treating" or "treated" refers to therapeutic treatment wherein the object is to slow (lessen) an undesired physiological condition, disorder or disease, or to obtain beneficial or desired clinical results. For the purposes described herein, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. In other embodiments, "treatment" or "treating" or "treated" refers to prophylactic measures, wherein the object is to delay onset of or reduce severity of an undesired physiological condition, disorder or disease, such as, for example is a person who is predisposed to a disease (e.g., an individual who carries a genetic marker for a disease such as breast cancer).

In some embodiments of the methods described herein, the MSLN binding proteins as described herein are administered in combination with an agent for treatment of the particular disease, disorder or condition. Agents include but are not limited to, therapies involving antibodies, small molecules (e.g., chemotherapeutics), hormones (steroidal, peptide, and the like), radiotherapies (γ-rays, X-rays, and/or the directed delivery of radioisotopes, microwaves, UV radiation and the like), gene therapies (e.g., antisense, retroviral therapy and the like) and other immunotherapies. In some embodiments, an MSLN binding protein as described herein is administered in combination with anti-diarrheal agents, anti-emetic agents, analgesics, opioids and/or non-steroidal anti-inflammatory agents. In some embodiments, an MSLN binding protein as described herein is administered in combination with anti-cancer agents. Nonlimiting examples of anti-cancer agents that can be used in the various embodiments of the disclosure, including pharmaceutical compositions and dosage forms and kits of the disclosure, include: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alpha-2a; interferon alpha-2b; interferon alpha-nl interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinzolidine sulfate; vinzolidine sulfate; vorozole; zeniplatin; zinostatin; zorubicin hydrochloride. Other examples of anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-I receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; HMG-CoA reductase inhibitor (such as but not limited to, Lovastatin, Pravastatin, Fluvastatin, Statin, Simvastatin, and Atorvastatin); loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; Vitaxin®; vorozole; zanoterone; zeniplatin; zilascorb; and zinostatin stimalamer. Additional anti-cancer drugs are 5-fluorouracil and leucovorin. These two agents are particularly useful when used in methods employing thalidomide and a topoisomerase inhibitor. In some embodiments, the anti-MSLN single domain binding protein of the present disclosure is used in combination with gemcitabine.

In some embodiments, an MSLN binding proteins as described herein is administered before, during, or after surgery.

Methods of Detection of Mesothelin Expression and Diagnosis of Mesothelin Associated Cancer According to another embodiment of the disclosure, kits for detecting expression of mesothelin in vitro or in vivo are provided. The kits include the foregoing MSLN binding proteins (e.g., a labeled anti-MSLN single domain antibody or antigen binding fragments thereof), and one or more compounds for detecting the label. In some embodiments, the label is selected from the group consisting of a fluorescent label, an enzyme label, a radioactive label, a nuclear magnetic resonance active label, a luminescent label, and a chromophore label.

In some cases, mesothelin expression is detected in a biological sample. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. A biological sample is typically obtained from a mammal, such as a human or non-human primate.

In one embodiment, provided is a method of determining if a subject has cancer by contacting a sample from the subject with an anti-MSLN single domain antibody as disclosed herein; and detecting binding of the single domain antibody to the sample. An increase in binding of the antibody to the sample as compared to binding of the antibody to a control sample identifies the subject as having cancer.

In another embodiment, provided is a method of confirming a diagnosis of cancer in a subject by contacting a sample from a subject diagnosed with cancer with an anti-MSLN single domain antibody as disclosed herein; and detecting binding of the antibody to the sample. An increase in binding of the antibody to the sample as compared to binding of the antibody to a control sample confirms the diagnosis of cancer in the subject.

In some examples of the disclosed methods, the single domain antibody is directly labeled.

In some examples, the methods further include contacting a second antibody that specifically binds the single domain antibody with the sample; and detecting the binding of the second antibody. An increase in binding of the second antibody to the sample as compared to binding of the second antibody to a control sample detects cancer in the subject or confirms the diagnosis of cancer in the subject.

In some cases, the cancer is mesothelioma, prostate cancer, lung cancer, stomach cancer, squamous cell carcinoma, pancreatic cancer, cholangiocarcinoma, triple negative breast cancer or ovarian cancer, or any other type of cancer that expresses mesothelin.

In some examples, the control sample is a sample from a subject without cancer. In particular examples, the sample is a blood or tissue sample.

In some cases, the antibody that binds (for example specifically binds) mesothelin is directly labeled with a detectable label. In another embodiment, the antibody that binds (for example, specifically binds) mesothelin (the first antibody) is unlabeled and a second antibody or other molecule that can bind the antibody that specifically binds mesothelin is labeled. A second antibody is chosen such that it is able to specifically bind the specific species and class of the first antibody. For example, if the first antibody is a llama IgG, then the secondary antibody may be an anti-llama-IgG. Other molecules that can bind to antibodies include, without limitation, Protein A and Protein G, both of which are available commercially. Suitable labels for the antibody or secondary antibody are described above, and include various enzymes, prosthetic groups, fluorescent materials, luminescent materials, magnetic agents and radioactive materials.

Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include 125I, 131I, 35S or 3H.

In an alternative embodiment, mesothelin can be assayed in a biological sample by a competition immunoassay utilizing mesothelin standards labeled with a detectable substance and an unlabeled antibody that specifically binds mesothelin. In this assay, the biological sample, the labeled mesothelin standards and the antibody that specifically bind mesothelin are combined and the amount of labeled mesothelin standard bound to the unlabeled antibody is determined. The amount of mesothelin in the biological sample is inversely proportional to the amount of labeled mesothelin standard bound to the antibody that specifically binds mesothelin.

The immunoassays and method disclosed herein can be used for a number of purposes. In one embodiment, the antibody that specifically binds mesothelin may be used to detect the production of mesothelin in cells in cell culture. In another embodiment, the antibody can be used to detect the amount of mesothelin in a biological sample, such as a tissue sample, or a blood or serum sample. In some examples, the mesothelin is cell-surface mesothelin. In other examples, the mesothelin is soluble mesothelin (e.g., mesothelin in a cell culture supernatant or soluble mesothelin in a body fluid sample, such as a blood or serum sample).

In one embodiment, a kit is provided for detecting mesothelin in a biological sample, such as a blood sample or tissue sample. For example, to confirm a cancer diagnosis in a subject, a biopsy can be performed to obtain a tissue sample for histological examination. Alternatively, a blood sample can be obtained to detect the presence of soluble mesothelin protein or fragment. Kits for detecting a polypeptide will typically comprise a single domain antibody, according to the present disclosure, that specifically binds mesothelin. In some embodiments, an antibody fragment, such as an scFv fragment, a VH domain, or a Fab is included in the kit. In a further embodiment, the antibody is labeled (for example, with a fluorescent, radioactive, or an enzymatic label).

In one embodiment, a kit includes instructional materials disclosing means of use of an antibody that binds mesothelin. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting mesothelin in a biological sample generally includes the steps of contacting the biological sample with an antibody which specifically reacts, under immunologically reactive conditions, to a mesothelin polypeptide. The antibody is allowed to specifically bind under immunologically reactive conditions to form an immune complex, and the presence of the immune complex (bound antibody) is detected directly or indirectly.

Methods of determining the presence or absence of a cell surface marker are well known in the art. For example, the antibodies can be conjugated to other compounds including, but not limited to, enzymes, magnetic beads, colloidal magnetic beads, haptens, fluorochromes, metal compounds, radioactive compounds or drugs. The antibodies can also be utilized in immunoassays such as but not limited to radioimmunoassays (RIAs), ELISA, or immunohistochemical assays. The antibodies can also be used for fluorescence activated cell sorting (FACS). FACS employs a plurality of color channels, low angle and obtuse light-scattering detection channels, and impedance channels, among other more sophisticated levels of detection, to separate or sort cells (see U.S. Pat. No. 5,061,620). Any of the single domain antibodies that bind mesothelin, as disclosed herein, can be used in these assays. Thus, the antibodies can be used in a conventional immunoassay, including, without limitation, an ELISA, an RIA, FACS, tissue immunohistochemistry, Western blot or imunoprecipitation.

EXAMPLES

The examples below further illustrate the described embodiments without limiting the scope of the invention.

Example 1: Ability of an Exemplar Anti-MSLN Single Domain Antibody of the Present Disclosure to Mediate T Cell Killing of Cancer Cells Expressing Mesothelin An exemplar anti-MSLN single domain antibody sequence is transfected into Expi293 cells (Invitrogen). The amount of the exemplar anti-MSLN antibody in the conditioned media from the transfected Expi293 cells is quantitated using an Octet instrument with Protein A tips and using a control anti-MSLN antibody as a standard curve.

Titrations of conditioned media is added to TDCC assays (T cell Dependent Cell Cytotoxicity assays) to assess whether the anti-MSLN single domain antibody is capable of forming a synapse between T cells and a mesothelin expressing ovarian cancer cell line, OVCAR8. Viability of the OVCAR8 cells is measured after 48 hours. It is seen that the exemplar anti-MSLN single domain antibody mediates T cell killing.

Furthermore, it is seen that the TDCC activity of the exemplar anti-MSLN single domain antibody is specific to mesothelin expressing cells, because the exemplar antibody does not mediate T cell killing of LNCaP cells, which do not express mesothelin.

Example 2: Methods to Assess Binding and Cytotoxic Activities of Several MSLN Targeting Trispecific Antigen Binding Proteins Containing a MSLN Binding Domain According to the Present Disclosure Protein Production Sequences of MSLN targeting trispecific molecules, containing a MSLN binding protein according to the present disclosure, were cloned into mammalian expression vector pCDNA 3.4 (Invitrogen) preceded by a leader sequence and followed by a 6x Histidine Tag (SEQ ID NO: 336). Expi293F cells (Life Technologies A14527) were maintained in suspension in Optimum Growth Flasks (Thomson) between 0.2 to 8×1e6 cells/mL in Expi 293 media. Purified plasmid DNA was transfected into Expi293 cells in accordance with Expi293 Expression System Kit (Life Technologies, A14635) protocols, and maintained for 4-6 days post transfection. The amount of the exemplary trispecific proteins being tested, in the conditioned media, from the transfected Expi293 cells was quantitated using an Octet instrument with Protein A tips and using a control trispecific protein for a standard curve.

Cytotoxicity Assays

A human T-cell dependent cellular cytotoxicity (TDCC) assay was used to measure the ability ofT cell engagers, including trispecific molecules, to direct T cells to kill tumor cells (Nazarian et al. 2015. J Biomol Screen. 20:519-27). In this assay, T cells and target cancer cell line cells are mixed together at a 10:1 ratio in a 384 wells plate, and varying amounts of the trispecific proteins being tested are added. The tumor cell lines are engineered to express luciferase protein. After 48 hours, to quantitate the remaining viable tumor cells, Steady-Glo® Luminescent Assay (Promega) was used.

In the instant study, titrations of conditioned media was added to TDCC assays (T cell Dependent Cell Cytotoxicity assays) to assess whether the anti-MSLN single domain antibody was capable of forming a synapse between T cells and a mesothelin expressing ovarian cancer cell line, OVCAR8. Viability of the OVCAR8 cells was measured after 48 hours. It was seen that the trispecific proteins mediated T cell killing. FIG. 1 shows an example cell viability assay with test trispecific proteins 2A2 and 2A4. The $EC_{50}$ for the TDCC activity of several other test trispecific proteins are listed below in Table 1.

TABLE 1

TDCC Activity of MSLN targeting trispecific proteins containing a MSLB binding protein according to the present disclosure

| Anti-MSLN TriTAC | Average EC50 [M] |
|---|---|
| 2A2 | 1.6E−12 |
| 2A4 | 1.9E−09 |
| 11F3 | 2.2E−12 |
| 5D4 | 1.0E−09 |
| 9H2 | 1.1E−12 |
| 5C2 | 1.5E−12 |
| 5G2 | 3.6E−09 |
| 10B3 | 1.4E−12 |
| 2F4 | 7.3E−13 |
| 2C2 | 9.5E−09 |
| 5F2 | 5.3E−12 |
| 7C4 | 1.0E−08 |
| 7F1 | 2.4E−12 |
| 5D2 | 1.4E−11 |
| 6H2 | 2.0E−09 |
| 2D1 | 5.2E−11 |
| 12C2 | 8.0E−13 |
| 3F2 | 2.4E−08 |
| 1H2 | 2.5E−08 |
| 6F3 | 8.2E−10 |
| 2A1 | 1.2E−09 |
| 3G1 | 4.0E−09 |
| 12D1 | 1.1E−09 |
| 5H1 | 5.9E−12 |
| 4A2 | 1.7E−09 |
| 3B4 | 1.8E−12 |
| 7H2 | 5.5E−12 |
| 9F3 | >1E−7 |
| 9B1 | >1E−7 |

Furthermore, it was observed that the TDCC activity of the MSLN targeting trispecific proteins being tested was specific to mesothelin expressing cells, because the trispecific proteins being tested did not mediate T cell killing of LNCaP cells, which do not express mesothelin. The trispecific proteins 2A2, 11F3, 9H2, 5C2, 10B3, 2F4, 5F2, 7F1, 2F4, 5H1, 3B4, and 7H2, in particular did not show any TDCC activity with the LnCaP cells.

Example 3: ADCC Activity of an Exemplar Anti-MSLN Single Domain Antibody of the Present Disclosure This study is directed to determining the ability of an exemplar anti-MSLN single domain antibody of the present disclosure to mediate ADCC as compared to a comparator llama anti-MSLN antibody which does not have sequence modifications or substitutions as the exemplary antibody of the disclosure. Both antibodies are expressed as multidomain proteins which include additional immunoglobulin domains.

Materials

Donors are leukophoresed, and NK cells are isolated from the leukopack by the Cell Purification Group using the Milteni AutoMacs Pro negative selection system. NK cells are held overnight at 4° C. on a rocker, then washed, counted and resuspended at $4\times10^6$ cells/mL in complete RPMI for use in the ADCC assay.

Targets: Tumor cell targets are selected based on mesothelin expression. Targets are washed and counted. $6\times10^6$ targets are resuspended in complete RPMI and labeled in a final concentration of 10 μM calcein (Sigma #C1359-00UL CALCEIN AM 4 MM IN ANHYDROUS DMSO) for 40 minutes at 37° C., 5% CO2. Cells are washed twice in PBS, resuspended in complete RPMI and incubated at 37° C., 5% CO2 for 2 hrs. After labeling, target cells are washed, recounted and resuspended at 0.2×106 cells/mL in complete RPMI for use in the ADCC assay.

Methods

The ADCC assay is performed in a 96 well round bottom tissue culture plate (Corning 3799). The test proteins are titrated from 20 μg/mL to 0.0002 μg/mL by carrying 10 μL in 1000 μL of complete RPMI containing 10% FCS (a 1:10 dilution). Calcein labeled targets are added, 50 μL to contain 10,000 cells. Target cells and various concentrations of the multidomain proteins containing either the exemplar anti-MSLN single domain antibody or the comparator antibodyare incubated for 40 minutes at 4° C., then NK cell effectors added, 50 μL to contain 100,000 cells (10:1 E:T ratio). Cultures are incubated for 4 hrs at 37° C. then supernatants pulled and assayed for calcein release by measuring fluorescence at 485-535 nm on a Wallac Victor II 1420 Multilable HTS counter. 100% lysis values are determined by lysing six wells of labeled targets with Igepal 630 detergent (3 μL per well) and spontaneous lysis values determined by measuring the fluorescence in supernatants from targets alone.

Statistical Analysis

Percent (%) specific lysis is defined as (sample fluorescence)-(spontaneous lysis fluorescence)/(100% lysis-spontaneous lysis fluorescence). Spontaneous lysis is determined by wells containing only targets and 100% lysis is determined by wells where targets are lysed with IGEPAL CA 630 detergent. Raw data is entered in an Excel spreadsheet with embedded formulae to calculate % specific lysis and resultant values transferred to graphic program (GraphPad Prism) where the data is transformed in a curve fit graph Subsequent analyses (linear regression calculations) are done in GraphPad to generate $EC_{50}$ values.

Results and Discussion

Effector NK cells in wells incubated with the multidomain protein containing the comparator anti-MSLN antibody are unable to mediate killing of the calcein-labeled target cells while effectors in wells with the multidomain protein containing the exemplar anti-MSLN single domain antibody of the present disclosure are, as measured by specific Lytic activity (% specific lysis) able to mediate antibody dependent cellular cytotoxicity.

Conclusions

The exemplary anti-MSLN single domain antibody of the present disclosure mediates a significantly higher level of killing, of target cells expressing mesothelin, than the comparator llama anti-MSLN single domain antibody with no sequence substitutions, modification, or humanization.

Example 4: CDC Activity of an Exemplar Anti-MSLN Single Domain Antibody of the Present Disclosure To evaluate the anti-tumor activity of exemplar anti-MSLN single domain antibody, according to the present disclosure, against cancer cells, the cytotoxic activity in A431/H9 and NCI-H226 cell models in the presence of human serum as a source of complement is tested. The exemplar anti-MSLN single domain antibody is expressed as a multidomain protein containing additional immunoglobulin domains. It is seen that the multidomain protein containing the exemplar anti-MSLN single domain antibody of the present disclosure exerts potent CDC activity by killing about 40% of A431/H9 and more than 30% of NCI-H226 mesothelioma cell lines, and shows no activity on the mesothelin-negative A431 cell line. A comparator llama anti-MSLN antibody, which does not have sequence modifications or substitutions as the exemplary antibody of the disclosure, shows no activity at the same concentrations.

In order to analyze the role of complement in the anti-tumor activity of the exemplar anti-MSLN single domain antibody, flow cytometry is used to determine Clq binding to cancer cells reacted with anti-mesothelin human mAbs following a well-established protocol for characterization of rituximab, ofatumumab and other anti-CD20 therapeutic mAbs (Pawluczkowycz et al., J Immunol 183:749-758, 2009; Li et al., Cancer Res 68:2400-2408, 2008). It has previously been shown that like MORAb-009, the HN1 human mAb specific for Region I of cell surface mesothelin (far from the cell surface), did not exhibit any CDC activity against mesothelin-expressing cancer cells (Ho et al., Int J Cancer 128:2020-2030, 2011).

However, it is seen that the Clq complement binds to A431/H9 or NCI-H226 cells in the presence of exemplar anti-MSLN single domain antibody. In contrast, no Clq binding is found in the presence of the comparator llama anti-MSLN antibody. Moreover, the binding of Clq to cancer cells is associated with the cell binding of exemplar anti-MSLN single domain antibody in a dose-response manner. These results demonstrate that the exemplar anti-MSLN single domain antibody demonstrates improved CDC activity relative to the comparator llama anti-MSLN antibody.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 5: MSLN Targeting Trispecific Antigen Binding Protein Containing a MSLN Binding Domain (MH6T) According to the Present Disclosure Directs T Cells to Kill MSLN Expressing Ovarian Cancer Cells A human T-cell dependent cellular cytotoxicity (TDCC) assay was used to measure the ability of T cell engagers, including trispecific molecules, to direct T cells to kill tumor cells (Nazarian et al. 2015. J Biomol Screen. 20:519-27). The Caov3 cells used in this assay were engineered to express luciferase. T cells from 5 different healthy donors (donor 02, donor 86, donor 41, donor 81, and donor 34) and target cancer cells Caov3 were mixed together and varying amounts of an MSLN targeting trispecific antigen binding protein containing the MSLN binding domain (MH6T) (SEQ ID NO: 58) was added and the mixture was incubated for 48 hours at 37° C. Caov3 cells and T cells were also incubated for 48 hours at 37° C. with a control trispecific molecule, GFP TriTAC (SEQ ID NO: 59), which targets GFP. After 48 hours, the remaining viable tumor cells were quantified by a luminescence assay.

Figure 2:
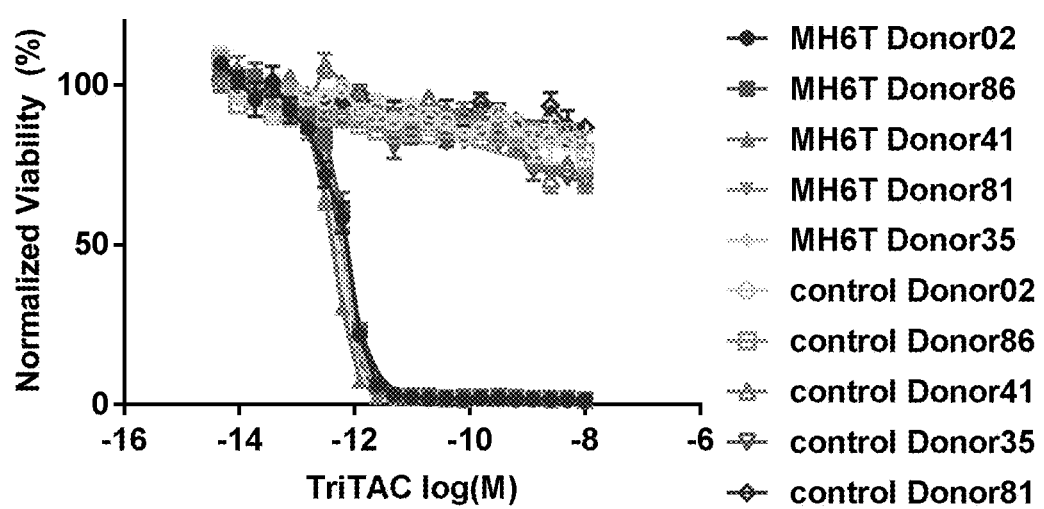
FIG. 2 illustrates that a trispecific MSLN target antigen binding protein containing an exemplary MSLN binding domain of this disclosure (MH6T) directs T cells from five donors (donor 02; donor 86; donor 41; donor 81; and donor 35) to kill Caov3 cells. The figure also illustrates that a control trispecific protein (GFP TriTAC) did not direct T cells from the five donors (donor 02; donor 86; donor 41; donor 81; and donor 35) to kill Caov3 cells.

It was observed that the MSLN targeting trispecific antigen binding protein containing the MSLN binding domain (MH6T) was able to direct the T cells from all 5 healthy donors to kill the target cancer cells Caov3 (as shown in FIG. 2), whereas the control GFP TriTAC molecule was not able to direct the T cells from any of the 5 healthy donors to kill the Caov3 cells (also shown in FIG. 2).

Figure 3:
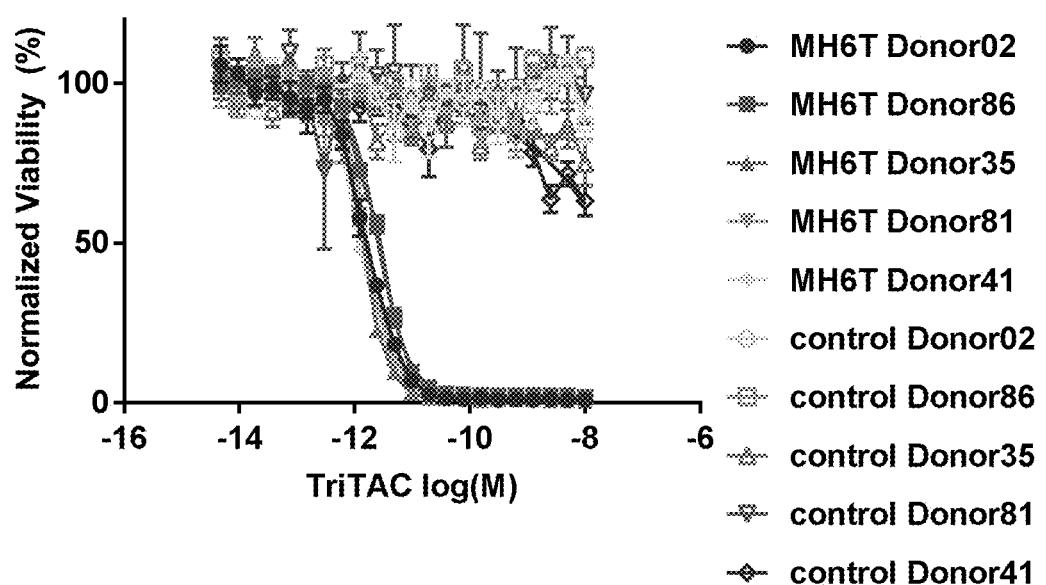
FIG. 3 illustrates that a trispecific MSLN target antigen binding protein containing an exemplary MSLN binding domain of this disclosure (MH6T) directs T cells from five donors (donor 02; donor 86; donor 41; donor 81; and donor 35) to kill OVCAR3 cells. The figure also illustrates that a control trispecific protein (GFP TriTAC) did not direct T cells from the five donors (donor 02; donor 86; donor 41; donor 81; and donor 35) to kill OVCAR3 cells.

A further assay, using the same protocol as described above, was carried out using OVCAR3 cells. It was observed that the MSLN targeting trispecific antigen binding protein containing the MSLN binding domain (MH6T) was able to direct the T cells from all 5 healthy donors to kill the target cancer cells OVCAR3 (as shown in FIG. 3), whereas the control GFP TriTAC molecule was not able to direct the T cells from any of the 5 health donors to kill the OVCAR3 cells (also shown in FIG. 3).

The $EC_{50}$ values for killing of MSLN expressing target cells are listed below in Table II.

TABLE II $EC_{50}$ values for MSLN targeting trispecific antigen binding protein (containing the MH6T domain) directed killing of MSLN-expressing ovarian cancer cell lines by T cells from 5 different healthy donors. Represented graphs of the raw data are provided in FIGS. 2 and 3.

| | $EC_{50}$ values (M) | | | | |
|---|---|---|---|---|---|
| | Donor02 | Donor86 | Donor41 | Donor81 | Donor35 |
| Caov3 | 6.0E−13 | 6.8E−13 | 3.9E−13 | 5.9E−13 | 4.6E−13 |
| Caov4 | 7.3E−12 | 1.1E−11 | 3.7E−12 | 4.7E−12 | 2.2E−12 |
| OVCAR3 | 1.6E−12 | 2.5E−12 | 1.4E−12 | 1.6E−12 | 1.3E−12 |
| OVCAR8 | 2.2E−12 | 3.2E−12 | 1.4E−12 | 1.9E−12 | 1.7E−12 |

Example 6: MSLN Targeting Trispecific Antigen Binding Protein Containing a MSLN Binding Domain (MH6T) According to the Present Disclosure Directs T Cells to Kill Cells Expressing MSLN but not Cells that do not Express MSLN In this assay, T cells from a healthy donor was incubated with target cancer cells that express MSLN (Caov3 cells, Caov4 cells, OVCAR3 cells, and OVCAR8 cells) or target cancer cells that do not express MSLN (NCI-H510A cells, MDAPCa2b cells). Each of the target cells used in this study were engineered to express luciferase. Varying amounts of an MSLN targeting trispecific antigen binding protein containing the MH6T (SEQ ID NO: 58) domain was added to the mixture of T cells and target cancer cells listed above. The mixture was incubated for 48 hours at 37° C. After 48 hours, the remaining viable target cancer cells were quantified using a luminescent assay.

Figure 4:
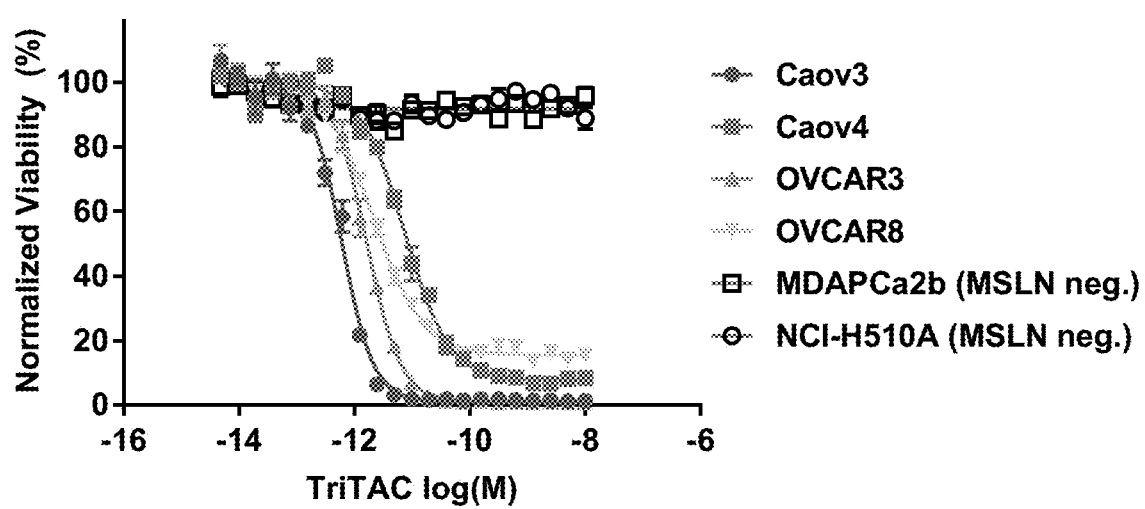
FIG. 4 illustrates that a trispecific MSLN target antigen binding protein containing an exemplary MSLN binding domain of this disclosure (MH6T) was able to direct T cells from a healthy donor to kill cells that express MSLN (OVCAR3 cells; Caov4 cells; OVCAR3 cells; and OVCAR8 cells). The figure also illustrates that the trispecific MSLN target antigen binding protein containing an exemplary MSLN binding domain of this disclosure (MH6T) was not able to direct T cells from the healthy donor to kill cells that do not express MSLN (MDAPCa2b cells; and NCI-H510A cells).

It was observed that the MSLN targeting trispecific antigen binding protein containing the MH6T domain was able to direct T cells to kill MSLN expressing target cancer cells (i.e., Caov3, Caov4, OVCAR3, and OVCAR8 cells, as shown in FIG. 4). However, the MSLN targeting trispecific antigen binding protein containing the MH6T domain was not able to direct T cells to kill MSLN non-expressing target cancer cells (MDAPCa2b and NCI-H510A cells), also shown in FIG. 4.

The $EC_{50}$ values for killing of MSLN expressing cancer cells are listed below in Table III.

TABLE III $EC_{50}$ values for MSLN targeting trispecific antigen binding protein (containing the MH6T domain) directed T cell killing of MSLN-expressing cancer cell lines.

| Tumor origin | Cell Line | $EC_{50}$ (pM) | MSLN sites per cell |
|---|---|---|---|
| Ovarian | Caov3 | 0.6 | 51262 |
| | Caov4 | 7.3 | 101266 |
| | OVCAR3 | 1.6 | 40589 |
| | OVCAR8 | 2.2 | 40216 |
| | SKOV3 | 3.6 | 10617 |
| Pancreatic | Hs766T | 7.8 | 5892 |
| | CaPan2 | 3.2 | 27413 |
| | HPaFII | 15 | 17844 |
| NSCLC | NCI-H596 | 1.5 | 103769 |
| | NCI-H292 | 3.8 | 5977 |
| | NCI-H1563 | 2.6 | 17221 |
| Mesothelioma | NCI-H2052 | 8.0 | not determined |
| | NCI-H2452 | 2.3 | not determined |
| Engineered | HEK293 expressing human MSLN | 0.9 | 128091 |
| (non-tumor) | HEK293 293 expressing cynomolgus MSLN | 0.7 | 140683 |

Example 7: MSLN Targeting Trispecific Antigen Binding Protein Containing an MSLN Binding Protein (MH6T) According to this Disclosure Directed T Cells from Cynomolgus Monkeys to Kill Human Ovarian Cancer Cell Lines In this assay, peripheral blood mononuclear cells (PBMCs; T cells are a component of the PBMCs) from a cynomolgus monkey donor were mixed with target cancer cells that express MSLN (CaOV3 cells and OVCAR3 cells) and varying amounts of an MSLN targeting trispecific antigen binding protein (containing the MH6T domain, SEQ ID NO: 58) was added to the mixture, and incubated for 48 hours at 37° C. In parallel, a mixture of cynomolgus PBMCs and MSLN expressing cells, as above, were incubated with varying amounts of a control TriTAC molecule GFP TriTAC (SEQ ID NO: 59) that targets GFP, for 48 hours at 37° C. Target cancer cells used in this assay were engineered to express luciferase. After 48 hours, the remaining viable target cells were quantified using a luminescence assay.

It was observed that the MSLN targeting trispecific antigen binding protein (containing the MH6T domain) was able to efficiently direct cynomolgus PBMCs to kill MSLN expressing cells (i.e., Caov3 and OVCAR), as shown in FIG.

Figure 5:
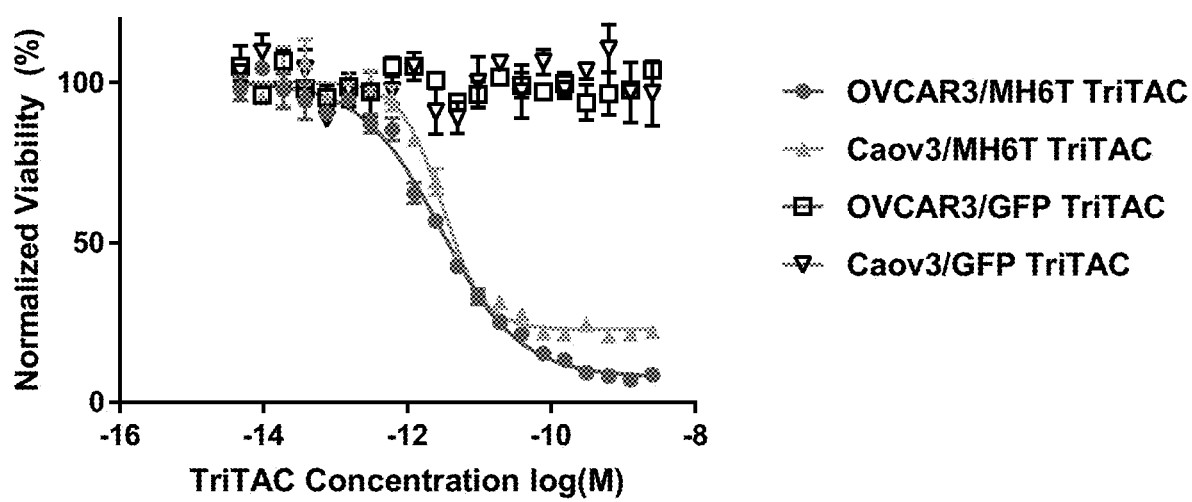
FIG. 5 illustrates that a trispecific MSLN target antigen binding protein containing an exemplary MSLN binding domain of this disclosure (MH6T) was able to direct T cells from cynomolgus monkeys to kill human ovarian cancer cells (OVCAR3 cells; Caov3 cells). The figure also illustrates that a control trispecific protein (GFP TriTAC) was not able to direct the T cells from cynomolgus monkeys to kill human ovarian cancer cells lines (OVCAR3 cells; Caov3 cells).

5, whereas the control GFP TriTAC molecule was not able to direct the cynomolgus PBMCs to kill the cells (also shown in FIG. 5). The $EC_{50}$ values for the MSLN targeting trispecific antigen binding protein (containing the MH6T domain) was 2.9 μM for OVCAR3 cells and 3.0 μM for Caov3 cells, which were not significantly different that $EC_{50}$ values observed with human T cells, as shown in Table II.

Example 8: MSLN Targeting Trispecific Antigen Binding Protein (Containing the MH6T Domain) Directed Killing of MSLN-Expressing NCI-H2052 Mesothelioma Cells by T Cells in the Presence or Absence of Human Serum Albumin The aim of this study was to assess if binding to human serum albumin (HSA) by an MSLN targeting trispecific antigen binding protein (containing the MH6T domain; SEQ ID NO: 58) impacted the ability of the protein to direct T cells to kill MSLN-expressing cells. NCI-H2052 mesothelioma cells used in this study were engineered to express luciferase. T cells from a healthy donor and MSLN expressing cells (NCI-H2052) were mixed and varying amounts of the MSLN targeting trispecific antigen binding protein (containing the MH6T domain) was added to the mixture. The mixture was incubated for 48 hours at 37° C., in presence or absence of HSA. A mixture of NCI-H2052 cells and T cells were also incubated for 48 hours at 37° C. with a control trispecific molecule, GFP TriTAC (SEQ ID NO: 59), which targets GFP, in presence or absence of HSA. After 48 hours, the remaining viable target cells were quantified using a luminescence assay.

Figure 6:
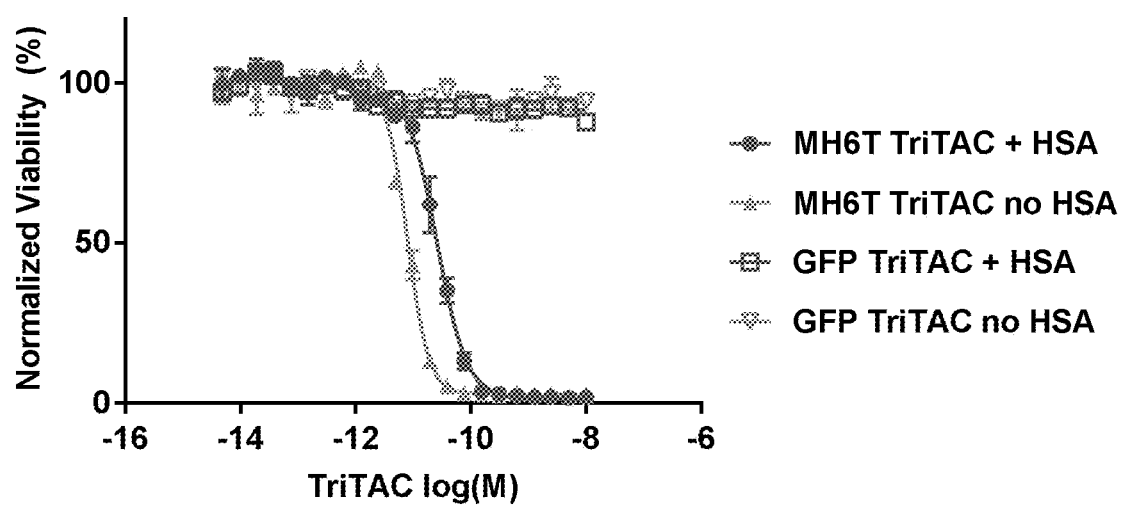
FIG. 6 illustrates that a trispecific MSLN target antigen binding protein containing an exemplary MSLN binding domain of this disclosure (MH6T) was able to direct killing of MSLN expressing NCI-H2052 mesothelioma cells by T cells, in the presence or absence of human serum albumin (HSA).

It was observed that the MSLN targeting trispecific antigen binding protein (containing the MH6T domain) was able to efficiently direct T cells to kill NCI-H2052 cells (as shown in FIG. 6) in presence or absence of HSA, whereas the control GFP TriTAC molecule was not able to do that (also shown in FIG. 6). It was also observed that in presence of HSA, the $EC_{50}$ value for cell killing was increased by about 3.2 folds (as shown in Table IV).

Further TDCC assays were carried out with the MSLN targeting trispecific antigen binding protein (containing the MH6T domain), in presence or absence of 15 mg/ml HSA, with additional MSLN-expressing cells lines and the $EC_{50}$ values are presented in Table IV.

TABLE IV $EC_{50}$ values for MSLN targeting trispecific antigen binding protein (containing the MH6T domain) directed killing of MSLN-expressing cancer cells by T cells in the presence or absence of HSA

| Cell line | $EC_{50}$ no HSA (pM) | $EC_{50}$ with HSA (pM) | $EC_{50}$ shift (fold) |
|---|---|---|---|
| OVCAR8 | 2.7 | 8.7 | 3.2 |
| SKOV3 | 3.9 | 11 | 2.8 |

TABLE IV-continued $EC_{50}$ values for MSLN targeting trispecific antigen binding protein (containing the MH6T domain) directed killing of MSLN-expressing cancer cells by T cells in the presence or absence of HSA

| Cell line | $EC_{50}$ no HSA (pM) | $EC_{50}$ with HSA (pM) | $EC_{50}$ shift (fold) |
|---|---|---|---|
| NCI-H2052 | 8.0 | 26 | 3.2 |
| NCI-H24522 | 2.3 | 6.3 | 2.7 |
| Caov3 | 0.8 | 3.6 | 4.3 |
| OVCAR3 | 1.6 | 3.8 | 2.4 |

Example 9: T Cells from 4 Different Donors Secrete TNF-α in the Presence of MSLN Targeting Trispecific Antigen Binding Protein (Containing the MH6T Domain) and MSLN-Expressing Caov4 Cells The target cancer cells CaOv4 used in this assay were engineered to express luciferase. In this assay, T cells from 4 different healthy donors (donor 02, donor 86, donor 35, and donor 81) and Caov4 cells were mixed together and varying amounts of an MSLN targeting trispecific antigen binding protein (containing the MH6T domain; SEQ ID NO: 58) was added and the mixture was incubated for 48 hours at 37° C. Caov4 cells and T cells were also incubated for 48 hours at 37° C. with a control trispecific molecule, GFP TriTAC (SEQ ID NO: 59), which targets GFP. Conditioned medium from the TDCC assay was collected at 48 hours, before measuring the target cancer cell viability, using a luminescence assay. The concentration of TNF-α in the conditioned medium was measured using an AlphaLISA assay kit (Perkin Elmer).

Figure 7:
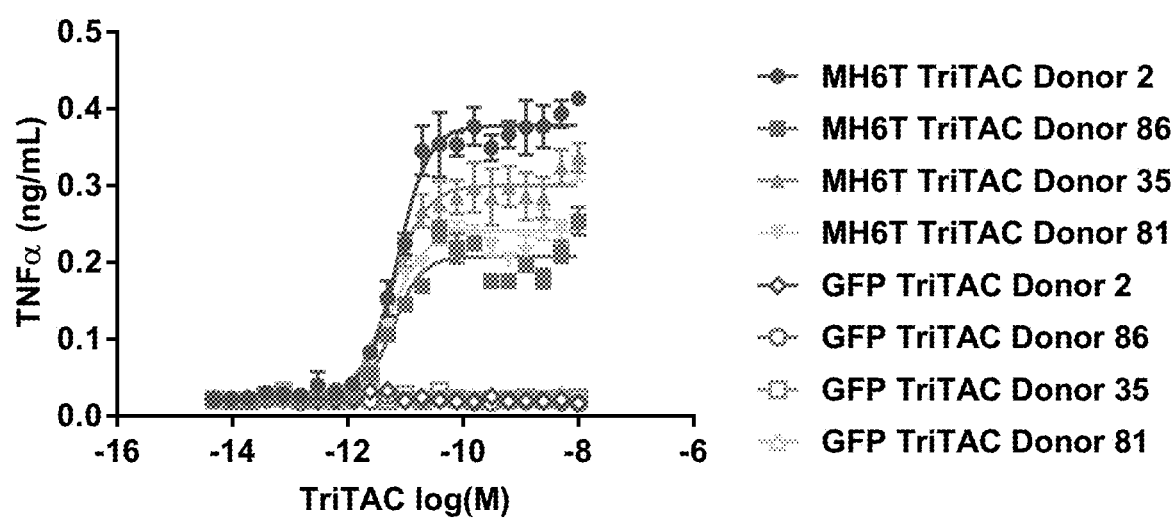
FIG. 7 illustrates that a trispecific MSLN target antigen binding protein containing an exemplary MSLN binding domain of this disclosure (MH6T) was able to activate T cells from four healthy donors (donor 2; donor 86; donor 35; and donor 81), as demonstrated by secretion of TNF-α from the T cells, in presence of MSLN-expressing Caov4 cells.

It was observed that TNF-α was secreted into the medium in presence of Caov4 cells and the MSLN targeting trispecific antigen binding protein (containing the MH6T domain) but not in presence of Caov4 cells and the control GFP TriTAC molecule, as shown in FIG. 7.

Furthermore, efficient killing was observed with T cells from all 4 healthy donors, in presence of the MSLN targeting trispecific antigen binding protein (containing the MH6T domain), but not in presence of the control GFP TriTAC molecule. TDCC assays were also set up for additional MSLN expressing cell lines (Caov3 cells, OVCAR3 cells, and OVCAR8 cells) and similar TNF-α expression was observed. The $EC_{50}$ values for MSLN targeting trispecific antigen binding protein (containing the MH6T domain) induced expression of TNF-α are presented in Table V. However, when the assay was carried out using cancer cells that do not express MSLN (NCI-H510A cells, or MDAPCa2b cells), no MSLN targeting trispecific antigen binding protein (containing the MH6T domain) directed secretion of TNF-α was observed (data not shown). Thus, this study demonstrated that the MSLN targeting trispecific antigen binding protein (containing the MH6T domain) was able to activate T cells in the presence of MSLN-expressing target cancer cells.

TABLE V $EC_{50}$ values for MSLN targeting trispecific antigen binding protein (containing the MH6T domain) induced expression of TNF-α by T cells from 4 different T cell donors and 4 different MSLN-expressing cell lines

| | TNFα $EC_{50}$ values (M) | | | |
|---|---|---|---|---|
| | MH6T Containing Trispecific Antigen Binding Protein Donor 2 | MH6T Containing Trispecific Antigen Binding Protein Donor 86 | MH6T Containing Trispecific Antigen Binding Protein Donor 35 | MH6T Containing Trispecific Antigen Binding Protein Donor 81 |
| Caov3 | 5.2E−12 | 5.4E−12 | 5.9E−12 | 4.9E−12 |
| Caov4 | 7.2E−12 | 6.0E−12 | 5.5E−12 | 5.5E−12 |

TABLE V-continued

EC$_{50}$ values for MSLN targeting trispecific antigen binding protein (containing the MH6T domain) induced expression of TNF-α by T cells from 4 different T cell donors and 4 different MSLN-expressing cell lines

| | TNFα EC$_{50}$ values (M) | | | |
|---|---|---|---|---|
| | MH6T Containing Trispecific Antigen Binding Protein Donor 2 | MH6T Containing Trispecific Antigen Binding Protein Donor 86 | MH6T Containing Trispecific Antigen Binding Protein Donor 35 | MH6T Containing Trispecific Antigen Binding Protein Donor 81 |
| OVCAR3 | 9.2E−12 | 4.0E−12 | 1.7E−11 | 8.9E−12 |
| OVCAR8 | 1.3E−11 | 9.1E−12 | 5.1E−12 | 5.0E−12 |

Example 10: Activation of CD69 Expression on T Cells from 4 Different Donors in Presence of MSLN Targeting Trispecific Antigen Binding Protein (Containing the MH6T Domain) and MSLN-Expressing OVCAR8 Cells The OVCAR8 cells used in this assay were engineered to express luciferase. In this assay, T cells from 4 different healthy donors (donor 02, donor 86, donor 35, and donor 81) and OVCAR8 cells were mixed together and varying amounts of the MSLN targeting trispecific antigen binding protein (containing the MH6T domain; SEQ ID NO: 58) was added and the mixture was incubated for 48 hours at 37° C. OVCAR8 cells and T cells were also incubated for 48 hours at 37° C. with a control trispecific molecule, GFP TriTAC (SEQ ID NO: 59), which targets GFP. After 48 hours, T cells were collected, and CD69 expression on the T cells was measured by flow cytometry.

Figure 8:
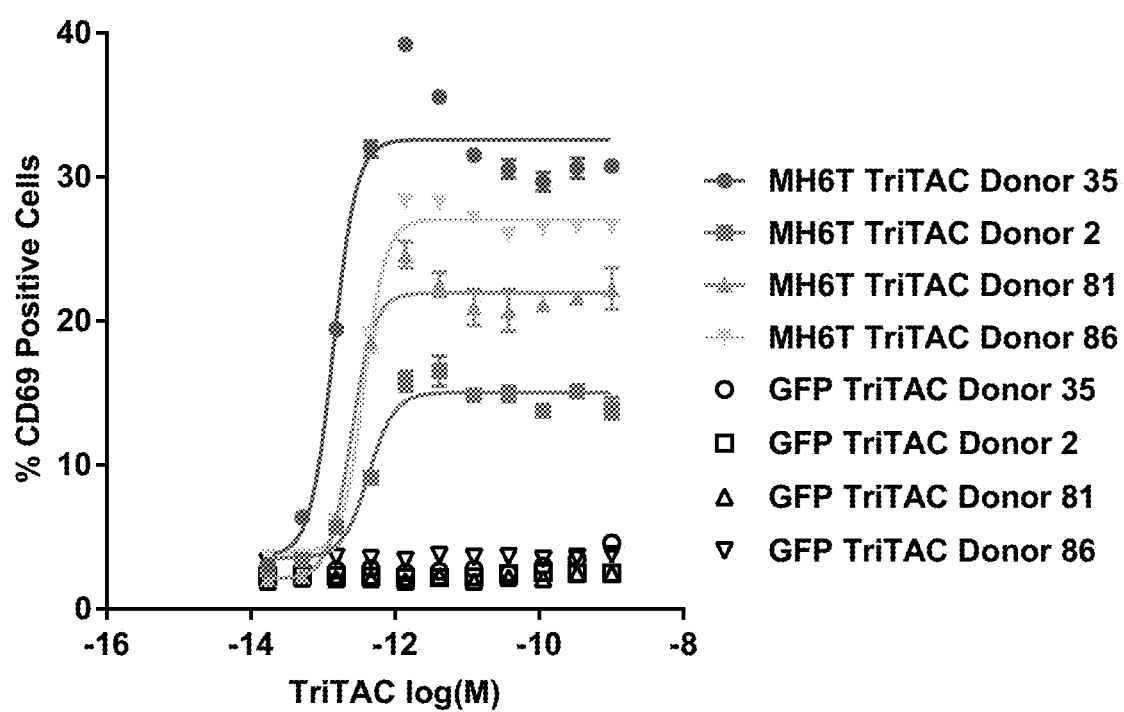
FIG. 8 illustrates that a trispecific MSLN target antigen binding protein containing an exemplary MSLN binding domain of this disclosure (MH6T) was able to activate T cells from four healthy donors (donor 2; donor 86; donor 35; and donor 81), as demonstrated by activation of CD69 expression on the T cells, in presence of MSLN-expressing OVCAR8 cells.

CD69 expression was detected on T cells from all 4 healthy donors in presence of OVCAR8 cells and the MSLN targeting trispecific antigen binding protein (containing the MH6T domain) but not in presence of the negative control GFP TriTAC and OVCAR8 cells, as shown in FIG. 8. TDCC assays were also set up for additional MSLN expressing cells (Caov3 cells, OVCAR3 cells, and OVCAR8 cells) and similar CD69 expression was observed. The EC$_{50}$ values for MSLN targeting trispecific antigen binding protein (containing the MH6T domain) induced activation of CD69 in Caov3 cells and OVCAR8 cells are presented in Table VI.

TABLE VI

EC$_{50}$ values for activation of CD69 expression on T cells from 4 different donors in presence of MSLN targeting trispecific antigen binding protein (containing the MH6T domain) and MSLN-expressing OVCAR8 cells or Caov3 cells.

| EC$_{50}$ table | Caov3 CD69 (M) | OVCAR8 CD69 (M) |
|---|---|---|
| Donor 35 | ~1.5E−13 | 1.4E−13 |
| Donor 2 | 2.5E−13 | 4.2E−13 |
| Donor 81 | 2.5E−13 | 2.5E−13 |
| Donor 86 | 3.7E−13 | 3.7E−13 |

When the assay was carried out using cancer cells that do not express MSLN (NCI-H510A cells or MDAPCa2b cells), no MSLN targeting trispecific antigen binding protein (containing the MH6T domain) induced activation of CD69 was observed (data not shown). Thus, this study demonstrated that the MSLN targeting trispecific antigen binding protein (containing the MH6T domain) was able to activate T cells in the presence of MSLN-expressing target cancer cells.

Example 11: Measurement of MSLN Targeting Trispecific Antigen Binding Protein (Containing the MH6T Domain) Binding to MSLN Expressing/Non-Expressing Cell Lines For this study, certain target cancer cells that express MSLN (Caov3 cells, CaOV4 cells, OVCAR3 cells, and OVCAR8 cells) and certain cancer cells that do not express MSLN (MDAPCa2b cells, and NCI-H510A cells) were incubated with the MSLN targeting trispecific antigen binding protein (containing the MH6T domain; SEQ ID NO: 58) or a control GFP TriTAC molecule (SEQ ID NO: 59). Following incubation, the cells were washed to remove unbound MH6T or GFP TriTAC molecules and further incubated with a secondary antibody, which is able to recognize the anti-albumin domain in the TriTAC molecules, conjugated to Alexa Fluor 647. Binding of the MSLN targeting trispecific antigen binding protein (containing the MH6T domain) or that of GFP TriTAC to the MSLN expressing or MSLN non-expressing cells was measured by flow cytometry.

Figure 9A:
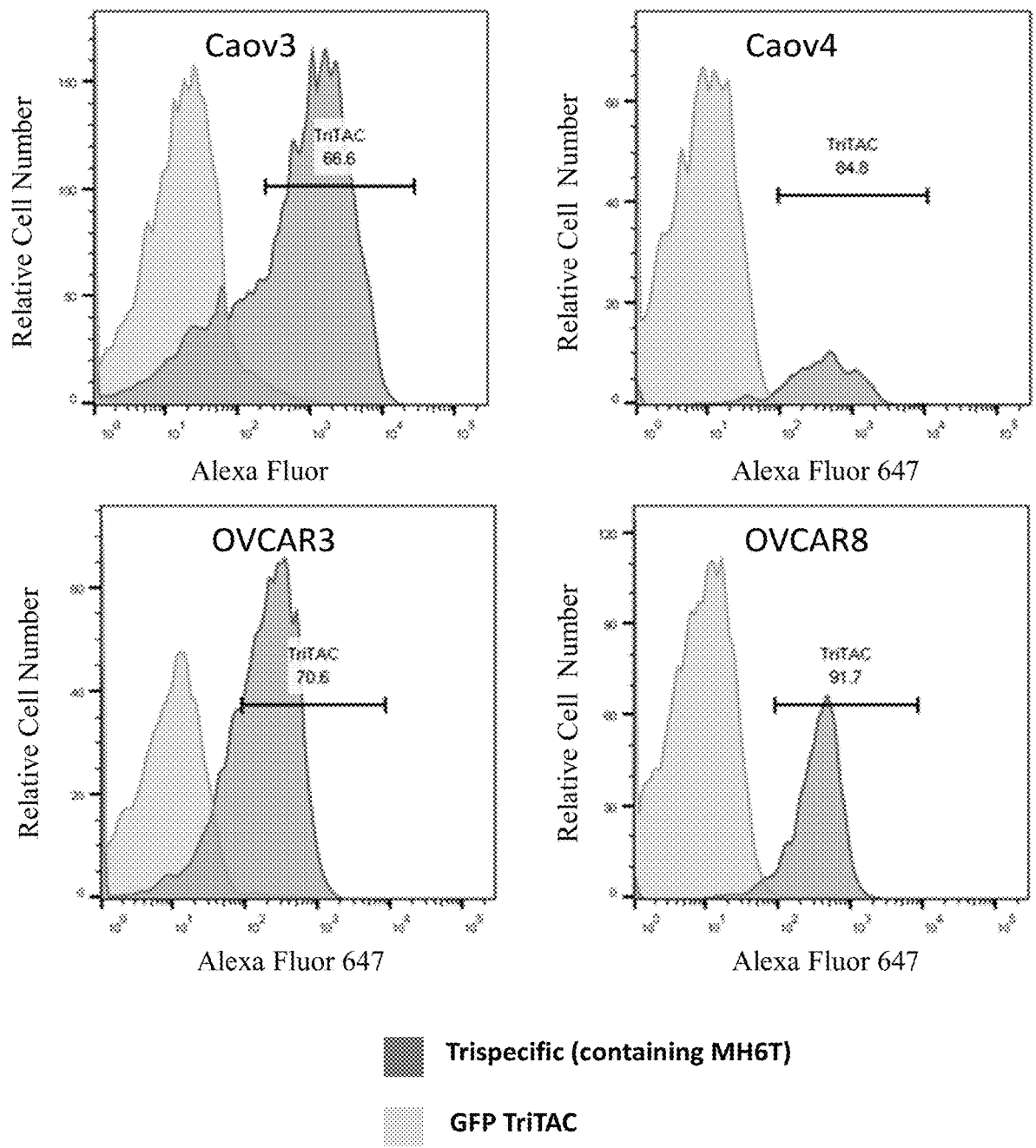
FIG. 9A shows binding with MSLN expressing cells (Caov3 cells-top left panel; Caov4 cells-top right panel; OVCAR3 cells-bottom left panel; OVCAR8 cells-bottom right panel) bound to the trispecific MSLN target antigen binding protein containing an exemplary MSLN binding domain of this disclosure (MH6T)
Figure 9B:
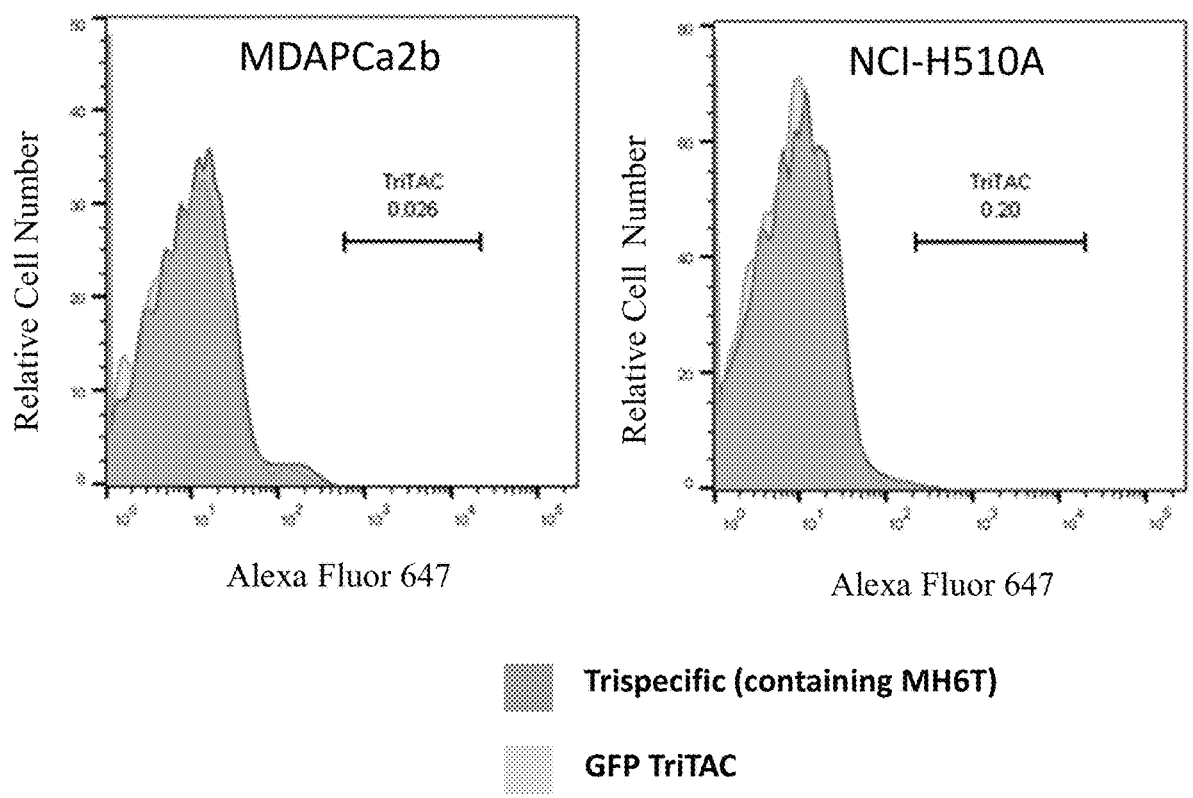
FIG. 9B shows lack of binding of both the trispecific MSLN target antigen binding protein containing an exemplary MSLN binding domain of this disclosure (MH6T) and the GFP TriTAC to MSLN non-expressing cell lines (MDCA2b cells-left panel; NCI-H510A cells-right panel).

Robust binding of the MSLN targeting trispecific antigen binding protein (containing the MH6T domain) to cell lines that express MSLN (Caov3, Caov4, OVCAR3, and OVCAR8) was observed, as seen in FIG. 9A (top left panel shows binding of the MSLN targeting trispecific target antigen binding protein containing the MH6T domain to Caov3 cells; top right panel shows binding of MSLN targeting trispecific target antigen binding protein containing the MH6T domain to Caov4 cells; bottom left panel shows binding of MSLN targeting trispecific target antigen binding protein containing the MH6T domain to OVCAR3 cells; bottom right panel shows binding of MSLN targeting trispecific target antigen binding protein containing the MH6T domain to OVCAR8 cells); and as seen in FIG. 9B, no binding was observed in cell lines that do not express MSLN (left panel shows lack of binding of MSLN targeting trispecific antigen binding protein (containing the MH6T domain) to MDAPCa2b cells and the right panel shows lack of binding of MSLN targeting trispecific antigen binding protein (containing the MH6T domain) to NCI-H510A cells). Furthermore, no binding was observed when any of the cell types were incubated with the GFP TriTAC molecule, as shown in both FIGS. 9A and 9B.

Example 12: Measurement of MSLN Targeting Trispecific Antigen Binding Protein (Containing the MH6T Domain) Binding to T Cells from Donors For this study, T cells from 4 healthy donors were incubated with an MSLN targeting trispecific antigen binding protein (containing the MH6T domain; SEQ ID NO: 58)

or a buffer, as negative control. Following incubation, the cells were washed to remove unbound MSLN targeting trispecific antigen binding protein (containing the MH6T domain) and further incubated with an Alexa Fluor 647 conjugated secondary antibody, which was able to recognize the anti-albumin domain in the MSLN targeting trispecific antigen binding protein (containing the MH6T domain). Binding was measured by flow cytometry.

Figure 10:
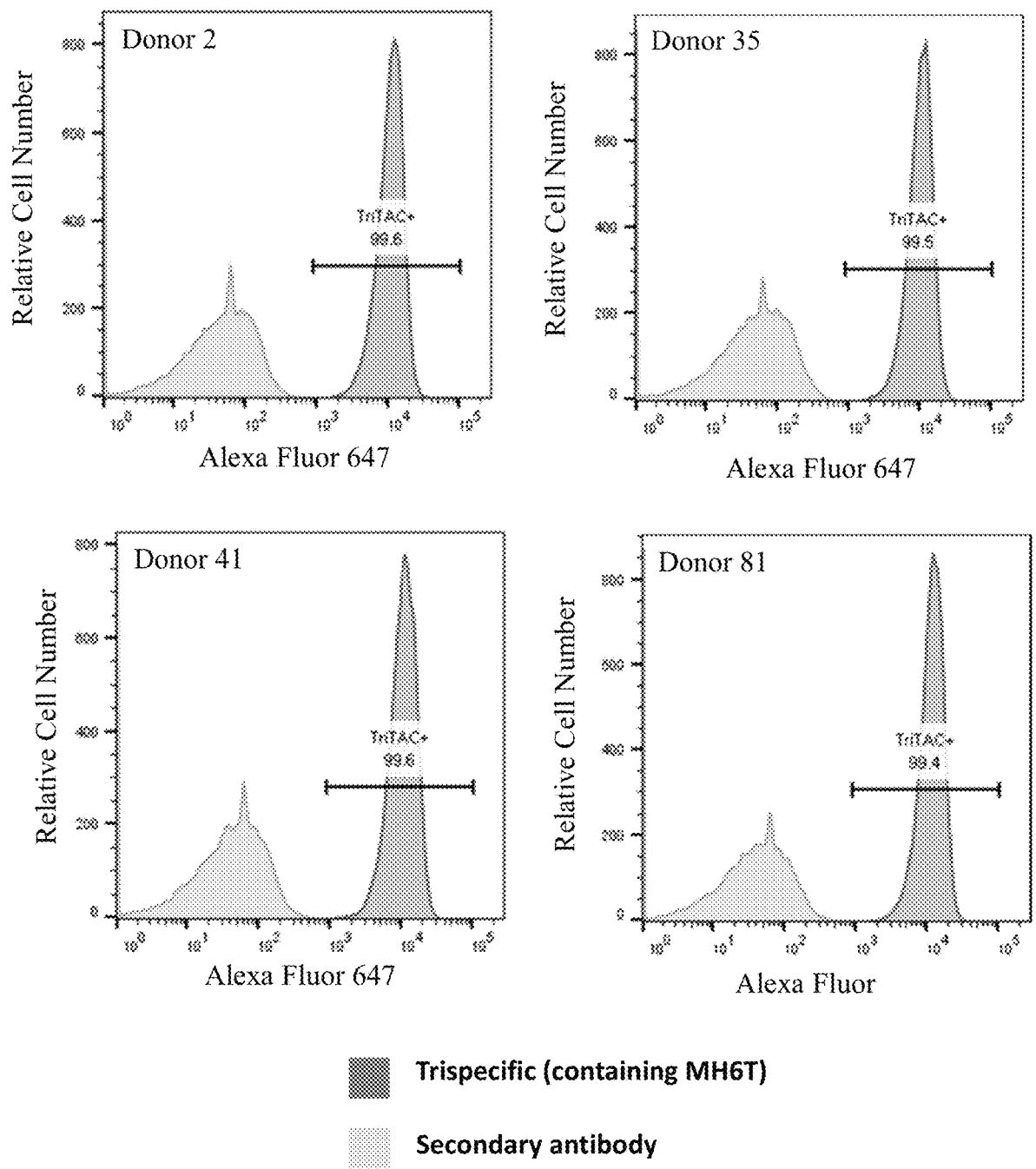
FIG. 10 illustrates binding of a trispecific MSLN target antigen binding protein containing an exemplary MSLN binding domain of this disclosure (MH6T) to T cells from four healthy donors (donor 2-top left panel; donor 35-top right panel; donor 41-bottom left panel; donor 81-bottom right panel).

Robust binding was observed in T cells from all four donors, treated with the MSLN targeting trispecific antigen binding protein (containing the MH6T domain), as shown in FIG. 10 (top left panel shows binding of MSLN targeting trispecific antigen binding protein (containing the MH6T domain) to T cells from donor 2; top right panel shows binding of MSLN targeting trispecific antigen binding protein (containing the MH6T domain) to T cells from donor 35; bottom left panel shows binding of MSLN targeting trispecific antigen binding protein (containing the MH6T domain) to T cells from donor 41; bottom right panel shows binding of MSLN targeting trispecific antigen binding protein (containing the MH6T domain) to T cells from donor 81).

Example 13: Inhibition of Tumor Growth in Mice Treated with MSLN Targeting Trispecific Antigen Binding Protein (Containing the MH6T Domain)

Figure 11:
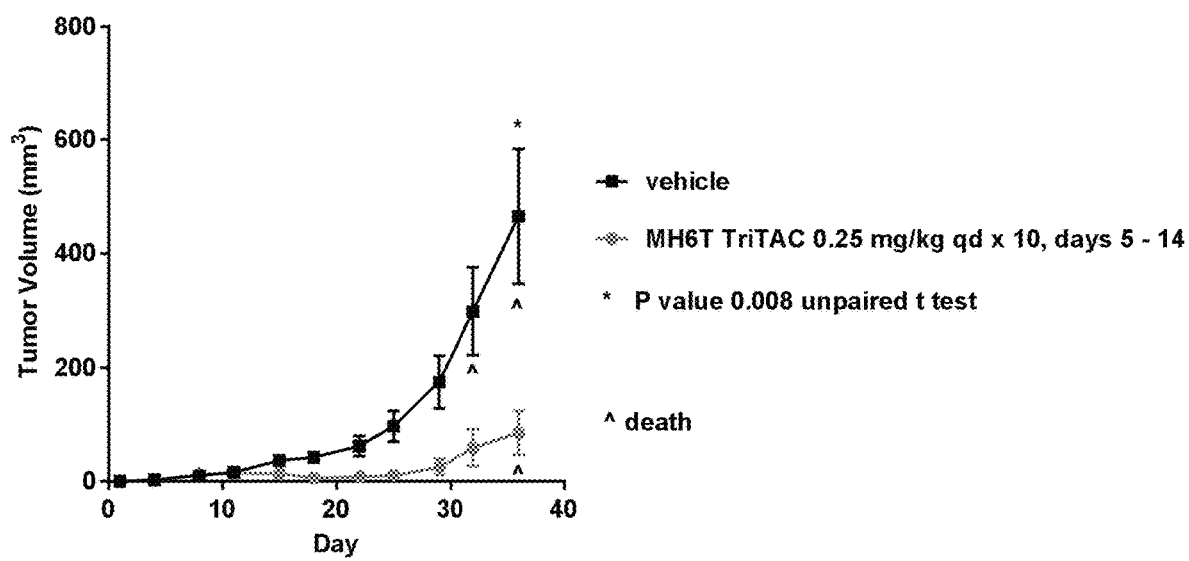
FIG. 11 illustrates that a trispecific MSLN target antigen binding protein containing an exemplary MSLN binding domain of this disclosure (MH6T) was able to inhibit tumor growth in NCG mice implanted with MSLN expressing NCI-H292 cells.

For this study, $10^7$ NCI-H292 cells and $10^7$ human PBMCs were co-implanted subcutaneously in two groups of NCG mice (8 mice per group). After 5 days, mice in one group were injected with the MSLN targeting trispecific antigen binding protein (containing the MH6T domain; SEQ ID NO: 58), daily for 10 days (days 5-14) at a dose of 0.25 mg/kg; and mice in the other group were injected with a vehicle control. Tumor volumes were measured after every few days and the study was terminated at day 36. Significant inhibition of tumor growth was observed in the mice injected with the MSLN targeting trispecific antigen binding protein (containing the MH6T domain), compared to those injected with the vehicle control, as shown in FIG. 11.

Figure 12:
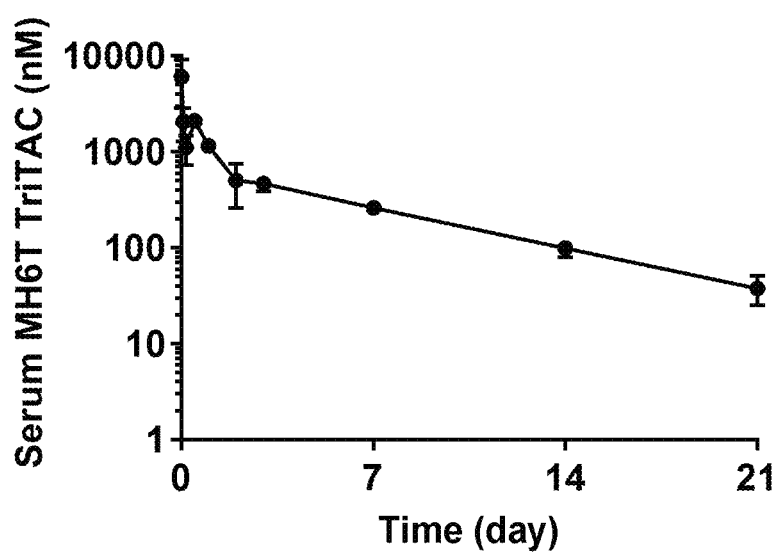
FIG. 12 illustrates pharmacokinetic profile of a trispecific MSLN target antigen binding protein containing an exemplary MSLN binding domain of this disclosure (MH6T). Serum levels of the trispecific MSLN target antigen binding protein containing an exemplary MSLN binding domain of this disclosure (MH6T), at various time points following injection into two cynomolgus monkeys, are shown in the plot.

Example 12: Pharmacokinetics of MSLN Targeting Trispecific Antigen Binding Protein (Containing the MH6T Domain) in Cynomolgus Monkeys For this study, two cynomolgus monkeys were injected with 10 mg/kg dose of an MSLN targeting trispecific antigen binding protein (containing the MH6T domain; SEQ ID NO: 58), intravenously, and serum samples were collected at various time points after the injection. The amount of the MSLN targeting trispecific antigen binding protein (containing the MH6T domain) in the serum was measured using anti-idiotype antibodies recognizing the MSLN targeting trispecific antigen binding protein (containing the MH6T domain), in an electrochemiluminescent assay. FIG. 12 shows a plot for the serum MSLN targeting trispecific antigen binding protein (containing the MH6T domain) levels at various time points. The data was then used to calculate the pharmacokinetic properties of the MSLN targeting trispecific antigen binding protein (containing the MH6T domain), as provided in Table VII.

TABLE VII

Pharmacokinetic parameters for MSLN targeting trispecific antigen binding protein (containing the MH6T domain)

| Dose Level | Terminal $t_{1/2}$ | $C_{max}$ (nM) | AUC, 0-inf (hr*nM) | Clearance (mL/hr/kg) | Vss (mL/kg) |
|---|---|---|---|---|---|
| 10 mg/kg | 112 | 6,130 | 355,000 | 0.58 | 70.0 |

Sequence Table

| | | |
|---|---|---|
| SEQ ID NO: 1 | 9B1 | QVQLVESGGGLVQPGGSLRLSCAASGRTFSVRGMAWYRQAGNNRALVATMN-PDG<br>FPNYADAVKGRFTISWDIAENTVYLQMNSLNSEDTTVYYCNSGPY-WGQGTQVTV<br>SS |
| SEQ ID NO: 2 | 9F3 | QVQLVESGGGLVQAGGSLRLSCAASGSIPSIEQMGWYRQAPGKQREL-VAALTSG<br>GRANYADSVKGRFTISGDNVRNMVYLQMNSLKPEDTAIYYCSAGRFK-GDYAQRS<br>GMDYWGKGTLVTVSS |
| SEQ ID NO: 3 | 7H2 | QVQLVESGGGLVQAGGSLRLSCAFSGTTYTFDLMSWYRQAPGKQRTVVA-SISSD<br>GRTSYADSVRGRFTISGENGKNTVYLQMNSLKLEDTAVYYCLGQRSGVRAF-WGQ<br>GTQVTVSS |
| SEQ ID NO: 4 | 3B4 | QVQLVESGGGLVQAGGSLRLSCVASGSTSNINNMRWYRQAPGKERELVA-VITRG<br>GYAIYLDAVKGRFTISRDNANNAIYLEMNSLKPEDTAVYVC-NADRVEGTSGGPQ<br>LRDYFGQGTQVTVSS |
| SEQ ID NO: 5 | 4A2 | QVQLVESGGGLVQAGGSLRLSCAASGSTFGINAMGWYRQAPGKQRELVA-VISRG<br>GSTNYADSVKGRFTISRDNAENTVSLQMNTLKPEDTAVYFCNARTYTRHDY-WGQ<br>GTQVTVSS |
| SEQ ID NO: 6 | 12D1 | QVRLVESGGGLVQAGGSLRLSCAASISAFRLMSVRWYRQDPSKQREW-VATIDQL<br>GRTNYADSVKGRFAISKDSTRNTVYLQMNMLRPEDTAVYYCNAGGGPLGSR-WLR<br>GRHWGQGTQVTVSS |

Sequence Table -continued

| SEQ ID NO: 7 | 3G1 | QVRLVESGGGLVQAGESLRLSCAASGRPFSINTMGWYRQAPGKQRELVA-SISSS GDFTYTDSVKGRFTISRDNAKNTVYLQMNSLKPEDTAVYYCNARRTYL-PRRFGS WGQGTQVTVSS |
|---|---|---|
| SEQ ID NO: 8 | 2A1 | QVQPVESGGGLVQPGGSLRLSCVVSGSDFTEDAMAWYRQASGKERES-VAFVSKD GKRILYLDSVRGRFTISRDIDKKTVYLQMDNLKPEDTGVYYCNSAP-GAARNYWG QGTQVTVSS |
| SEQ ID NO: 9 | 6F3 | QVQPVESGGGLVQPGGSLRLSCVVSGSDFTEDAMAWYRQASGKERES-VAFVSKD GKRILYLDSVRGRFTISRDIYKKTVYLQMDNLKPEDTGVYYCNSAPGAARN-VWG QGTQVTVSS |
| SEQ ID NO: 10 | 1H2 | EVQLVESGGGLVQPGNSLRLSCAASGFTFSSFGMSWVRQAPGKGLEWVS-SISGS GSDTLYADSVKGRFTISRDNAKTTLYLQMNSLRPEDTAVYYCTIGG-SLSRSSQG TLVTVSS |
| SEQ ID NO: 11 | 3F2 | QVQIVESGGGLVQAGGSLRLSCVASGLTYSIVAVGWYRQAPGKEREM-VADISPV GNTNYADSVKGRFTISKENAKNTVYLQMNSLKPEDTAVYYCHIVRGWLDER-PGP GPIVYWGQGTQVTVSS |
| SEQ ID NO: 12 | 12C2 | QVQLVESGGGLVQTGGSLRLSCAASGLTFGVYGMEWFRQAPG-KQREWVASHTST GYVYYRDSVKGRFTISRDNAKSTVYLQMNSLKPEDTAIYYCKANRGSYEY-WGQG TQVTVSS |
| SEQ ID NO: 13 | 2D1 | QVQLVESGGGLVQAGGSLRLSCAASTTSSINSMSWYRQAQGKQREPVAVIT-DRG STSYADSVKGRFTISRDNAKNTVYLQMNSLKPEDTAIYTCHVIADWRGY-WGQGT QVTVSS |
| SEQ ID NO: 14 | 6H2 | QVQLVESGGGLVQAGGSLRLSCAASGRTLSRYAMGWFRQAPGKER-QFVAAISRS GGTTRYSDSVKGRFTISRDNAANTFYLQMNNLRPDDTAVYYCNVRRRG-WGRTLE YWGQGTQVTVSS |
| SEQ ID NO: 15 | 5D2 | QVQLGESGGGLVQAGGSLRLSCAASGSIFSPNAMIWHRQAPGKQREPVA-SINSS GSTNYGDSVKGRFTVSRDIVKNTMYLQMNSLKPEDTAVYYCSYSD-FRRGTQYWG QGTQVTVSS |
| SEQ ID NO: 16 | 7C4 | QVQLVESGGGLVPSGGSLRLSCAASGATSAITNLGWYRRAPGQVREMVA-RISVR EDKEDYEDSVKGRFTISRDNTQNLVYLQMNNLQPHDTAIYYCGAQRWGRG-PGTT WGQGTQVTVSS |
| SEQ ID NO: 17 | 5F2 | QVQLVESGGGLVQAGGSLRLSCAASGSTFRIRVMRWYRQAPGTERDLVA-VISGS STYYADSVKGRFTISRDNAKNTLYLQMNNLKPEDTAVYYCNADDSGIARDY-WGQ GTQVTVSS |
| SEQ ID NO: 18 | 2C2 | QVQLVESGGGLVQAGESRRLSCAVSGDTSKFKAVGWYRQAPGAQRELLAW-INNS GVGNTAESVKGRFTISRDNAKNTVYLQMNRLTPEDTDVYYCRFYRRF-GINKNYW GQGTQVTVSS |
| SEQ ID NO: 19 | 5G2 | QVQLVESGGGLVQAGGSLRLSCAASGSTFGNKPMGWYRQAPGKQRELVA-VISSD GGSTRYAALVKGRFTISRDNAKNTVYLQMESLVAEDTAVYYCNALR-TYYLNDPV VFSWGQGTQVTVSS |

-continued

| Sequence Table | | |
|---|---|---|
| SEQ ID NO: 20 | 9H2 | QVQLVESGGGLVQAGGSLRLSCAASGSTSSINTMYWYRQAPGKEREL-VAFISSG GSTNVRDSVKGRFSVSRDSAKNIVYLQMNSLTPEDTAVYYCNTYIPLRGTL-HDY WGQGTQVTVSS |
| SEQ ID NO: 21 | 5D4 | QVQLVESGGGLVQAGGSLRLSCVASGRTDRITTMGWYRQAPGKQRELVA-TISNR GTSNYANSVKGRFTISRDNAKNTVYLQMNSLKPEDTAVYYCNARKWGRNY-WGQG TQVTVSS |
| SEQ ID NO: 22 | 2A4 | QVQLVESGGGLVQARGSLRLSCTASGRTIGINDMAWYRQAPGNQREL-VATITKG GTTDYADSVDGRFTISRDNAKNTVYLQMNSLKPEDTAVYYCNTKRREWAKD-FEY WGQGTQVTVSS |
| SEQ ID NO: 23 | 7F1 | QVQLVESGGGLVQAGGSLRLSCAASAIGSINSMSWYRQAPGKQREPVAVIT-DRG STSYADSVKGRFTISRDNAKNTVYLQMNSLKPEDTAIYTCHVIADWRGY-WGQGT QVTVSS |
| SEQ ID NO: 24 | 5C2 | QVQLVESGGGLVQAGGSLRLSCAASGSTSSINTMYWFRQAPGEERELVAT-INRG GSTNVRDSVKGRFSVSRDSAKNIVYLQMNRLKPEDTAVYYCNTYIPYGGTL-HDF WGQGTQVTVSS |
| SEQ ID NO: 25 | 2F4 | QVQLVESGGGLVQAGGSLRLSCTTSTTFSINSMSWYRQAPGNQREPVAVIT-NRG TTSYADSVKGRFTISRDNARNTVYLQMDSLKPEDTAIYTCHVIADWRGY-WGQGT QVTVSS |
| SEQ ID NO: 26 | 2A2 | QVQLVESGGGLVQAGGSLTLSCAASGSTFSIRAMRWYRQAPGTERDLVAVI-YGS STYYADAVKGRFTISRDNAKNTLYLQMNNLKPEDTAVYYCNADTIGTARDY-WGQ GTQVTVSS |
| SEQ ID NO: 27 | 11F3 | QVQLVESGGGLVQAGGSLRLSCVASGRTSTIDTMYWHRQAPGNERELVAY-VTSR GTSNVADSVKGRFTISRDNAKNTAYLQMNSLKPEDTAVYYCSVRTTSYPVD-FWG QGTQVTVSS |
| SEQ ID NO: 28 | 10B3 | QVQLVESGGGLVQAGGSLRLSCAASGSTSSINTMYWYRQAPGKEREL-VAFISSG GSTNVRDSVKGRFSVSRDSAKNIVYLQMNSLKPEDTAVYYCNTYIPYGGTL-HDF WGQGTQVTVSS |
| SEQ ID NO: 29 | 5H1 | QVQLVESGGGLVQPGGSLRLSCAASGGDWSANFMYWYRQAPGKQRELVA-RISGR GVVDYVESVKGRFTISRDNAKNTVYLQMNSLKPEDTAVYYCAVASY-WGQGTQVT VSS |
| SEQ ID NO: 30 | MH1 (humanized version of 5H1) | EVQLVESGGGLVQPGGSLRLSCAASGGDWSANFMYWYRQAPGKQRELVA-RISGR GVVDYVESVKGRFTISRDNSKNTLYLQMNSLRAEDTAVYYCAVASY-WGQGTLVT VSS |
| SEQ ID NO: 31 | MH2 (humanized version of 5H1) | EVQLVESGGGLVQPGGSLRLSCAASGGDWSANFMYWVRQAPGKGLEWVS-RISGR GVVDYVESVKGRFTISRDNSKNTLYLQMNSLRAEDTAVYYCAVASY-WGQGTLVT VSS |
| SEQ ID NO: 32 | MH3 (humanized version of 10B3) | EVQLVESGGGLVQAGGSLRLSCAASGSTSSINTMYWYRQAPGKEREL-VAFISSG GSTNVRDSVKGRFTISRDNSKNTLYLQMNSLRAEDTAVYYCNTYIPYGGTL-HDF WGQGTLVTVSS |

Sequence Table (continued)

| | | |
|---|---|---|
| SEQ ID NO: 33 | MH4 (humanized version of 10B3) | EVQLVESGGGLVQPGGSLRLSCAASGSTSSINTMYWYRQAPGKEREL-VAFISSGGSTNVRDSVKGRFTISRDNSKNTLYLQMNSLRAEDTAVYYCNTYIPYGGTL-HDFWGQGTLVTVSS |
| SEQ ID NO: 34 | MH5 (humanized version of 10B3) | EVQLVESGGGLVQPGGSLRLSCAASGSTSSINTMYWVRQAPGKGLEWVS-FISSGGSTNVRDSVKGRFTISRDNSKNTLYLQMNSLRAEDTAVYYCNTYIPYGGTL-HDFWGQGTLVTVSS |
| SEQ ID NO: 35 | MH6-GG (humanized version of 2A2) | QVQLVESGGGVVQAGGSLRLSCAASGSTFSIRAMRWYRQAPGTERDLVAVI-YGSSTYYADAVKGRFTISRDNSKNTLYLQMNSLRAEDTAVYYCNADTIGTARDY-WGQGTLVTVSS |
| SEQ ID NO: 36 | MH7-GG (humanized version of 2A2) | QVQLVESGGGVVQPGGSLRLSCAASGSTFSIRAMRWYRQAPGKERELVAVI-YGSSTYYADAVKGRFTISRDNSKNTLYLQMNSLRAEDTAVYYCNADTIGTARDY-WGQGTLVTVSSGG |
| SEQ ID NO: 37 | MH8-GG (humanized version of 2A2) | QVQLVESGGGVVQPGGSLRLSCAASGSTFSIRAMRWVRQAPGKGLEWVSVI-YGSSTYYADAVKGRFTISRDNSKNTLYLQMNSLRAEDTAVYYCNADTIGTARDY-WGQGTLVTVSSGG |
| SEQ ID NO: 38 | MH9 (humanized version of 11F3) | EVQLVESGGGLVQAGGSLRLSCVASGRTSTIDTMYWHRQAPGNERELVAY-VTSRGTSNVADSVKGRFTISRDNSKNTLYLQMNSLRAEDTAVYYCSVRTTSYPVD-FWGQGTLVTVSGG |
| SEQ ID NO: 39 | MH10 (humanized version of 11F3) | EVQLVESGGGLVQPGGSLRLSCAASGRTSTIDTMYWHRQAPGKERELVAY-VTSRGTSNVADSVKGRFTISRDNSKNTLYLQMNSLRAEDTAVYYCSVRTTSYPVD-FWGQGTLVTVSS |
| SEQ ID NO: 40 | MH11 (humanized version of 11F3) | EVQLVESGGGLVQPGGSLRLSCAASGRTSTIDTMYWVRQAPGK-GLEWVSYVTSRGTSNVADSVKGRFTISRDNSKNTLYLQMNSLRAEDTAVYYCSVRTTSYPVD-FWGQGTLVTVSS |
| SEQ ID NO: 41 | Exemplary conserved region in MSLN binding domain | ESGGGLV |
| SEQ ID NO: 42 | Exemplary conserved region in MSLN binding domain | LSC |
| SEQ ID NO: 43 | Exemplary conserved region in MSLN binding domain | GRF |
| SEQ ID NO: 44 | Exemplary conserved region in MSLN binding domain | VTVSS |

-continued

Sequence Table

| SEQ ID NO: 45 | Exemplary conserved region in MSLN binding domain | QLVESGGG |
|---|---|---|
| SEQ ID NO: 46 | Exemplary conserved region in MSLN binding domain | GGSLRLSCAASG |
| SEQ ID NO: 47 | Exemplary conserved region in MSLN binding domain | ASG |
| SEQ ID NO: 48 | Exemplary conserved region in MSLN binding domain | RQAPG |
| SEQ ID NO: 49 | Exemplary conserved region in MSLN binding domain | VKGRFTISRDNSKNTLYLQMNSLRAEDTAVYYC |
| SEQ ID NO: 50 | Exemplary conserved region in MSLN binding domain | WGQGTLVTVSS |
| SEQ ID NO: 51 | Exemplary CDR1 of MSLN binding domain | GRTFSVRGMA |
| SEQ ID NO: 52 | Exemplary CDR2 of MSLN binding domain | INSSGSTNYG |
| SEQ ID NO: 53 | Exemplary CDR3 of MSLN binding domain | NAGGGPLGSR |
| SEQ ID NO: 54 | Exemplary CDR1 of MSLN binding domain | GGDWSANFMY |
| SEQ ID NO: 55 | Exemplary CDR2 of MSLN binding domain | ISSGGSTNVR |
| SEQ ID NO: 56 | Exemplary CDR3 of MSLN binding domain | NADTIGTARD |
| SEQ ID NO: 57 | Mesothelin protein sequence | MALPTARPLLGSCGTPALGSLLFLLFSLGWVQPSRTLAGETGQEAAPLDGV-LAN PPNISSLSPRQLLGFPCAEVSGLSTERVRELAVALAQKNVKLSTEQLR-CLAHRL SEPPEDLDALPLDLLLFLNPDAFSGPQACTRFFSRITKANVDLLPRGAPER-QRL LPAALACWGVRGSLLSEADVRALGGLACDLPGRFVAESAEVLLPRLVSCPG-PLD QDQQEAARAALQGGGPPYGPPSTWSVSTMDALRGLLPVLGQPIIRSIPQ-GIVAA WRQRSSRDPSWRQPERTILRPRFRREVEKTACPSGKKAREIDESLIFYK-KWELE |

Sequence Table

| | | |
|---|---|---|
| | | ACVDAALLATQMDRVNAIPFTYEQLDVLKHKLDELYPQGYPESVIQHLGYL-FLK MSPEDIRKWNVTSLETLKALLEVNKGHEMSPQAPRRPLPQVATLIDRFVK-GRGQ LDKDTLDTLTAFYPGYLCSLSPEELSSVPPSSIWAVRPQDLDTCDPRQLDV-LYP KARLAFQNMNGSEYFVKIQSFLGGAPTEDLKALSQQNVSMDLATFMKLRT-DAVL PLTVAEVQKLLGPHVEGLKAEERHRPVRDWILRQRQDDLDTLGLGLQG-GIPNGY LVLDLSMQEALSGTPCLLGPGPVLTVALLLASTLA |
| SEQ ID NO: 58 | MH6T (exemplary MSLN binding domain) | QVQLVESGGGVVQAGGSLTLSCAASGSTFSIRAMRWYRQAPGTERDLVAVI-YGS STYYADAVKGRFTISRDNSKNTLYLQMNSLRAEDTAVYYCNADTIGTARDY-WGQ GTLVTVSS |
| SEQ ID NO: 59 | A trispecific molecule containing a GFP binding domain | QVQLVESGGALVQPGGSLRLSCAASGFPVNRYSMRWYRQAPGK-EREWVAGMSSA GDRSSYEDSVKGRFTISRDDARNTVYLQMNSLKPEDTAVYYCNVNVGFEY-WGQG TQVTVSSGGGGSGGGGSEVQLVESGGGLVQPGNSLRLSCAASGFTFSKFGM-SWVR QAPGKGLEWVSSISGSGRDTLYADSVKGRFTISRDNAKTTLYLQMNSL-RPEDTA VYYCTIGGSLSVSSQGTLVTVSSGGGGSGGGGSEVQLVESGGGLVQPGG-SLKLSC AASGFTFNKYAINWVRQAPGKGLEWVARIRSKYNNYATYY-ADQVKDRFTISRDD SKNTAYLQMNNLKTEDTAVYYCVRHANFGNSYISYWAYWGQGTLVT-VSSGGGGS GGGGSGGGGSQTVVTQEPSLTVSPGGTVTLTCASSTGAVTSGNYPNWVQQK-PGQ APRGLIGGTKFLVPGTPARFSGSLLGGKAALTLSGVQPEDEAEYYCTLWYS-NRW VFGGGTKLTVLHHHHHH |
| SEQ ID NO: 60 | MH6 (exemplary humanized version of 2A2) | QVQLVESGGGVVQAGGSLRLSCAASGSTFSIRAMRWYRQAPGTERDLVAVI-YGS STYYADAVKGRFTISRDNSKNTLYLQMNSLRAEDTAVYYCNADTIGTARDY-WGQ GTLVTVSS |
| SEQ ID NO: 61 | MH7 (exemplary humanized version of 2A2) | QVQLVESGGGVVQPGGSLRLSCAASGSTFSIRAMRWYRQAPGKERELVAVI-YGS STYYADAVKGRFTISRDNSKNTLYLQMNSLRAEDTAVYYCNADTIGTARDY-WGQ GTLVTVSS |
| SEQ ID NO: 62 | MH8 (humanized version of 2A2) | QVQLVESGGGVVQPGGSLRLSCAASGSTFSIRAMRWVRQAPGKGLEWVSVI-YGS STYYADAVKGRFTISRDNSKNTLYLQMNSLRAEDTAVYYCNADTIGTARDY-WGQ GTLVTVSS |

CDR1 sequences for various exemplary MSLN binding domains of this disclosure

| SequenceID No. | Exemplary MSLN binding domain | CDR1 Sequence |
|---|---|---|
| 63 | 9B1 | GRTFSVRGMA |
| 64 | 9F3 | GSIPSIEQMG |
| 65 | 7H2 | GTTYTFDLMS |
| 66 | 3B4 | GSTSNINNMR |
| 67 | 4A2 | GSTFGINAMG |
| 68 | 12D1 | ISAFRLMSVR |
| 69 | 3G1 | GRPFSINTMG |
| 70 | 2A1 | GSDFTEDAMA |
| 71 | 6F3 | GSDFTEDAMA |

CDR1 sequences for various exemplary MSLN binding domains of this disclosure

| SequenceID No. | Exemplary MSLN binding domain | CDR1 Sequence |
|---|---|---|
| 72 | 1H2 | GFTFSSFGMS |
| 73 | 3F2 | GLTYSIVAVG |
| 74 | 12C2 | GLTFGVYGME |
| 75 | 2D1 | TTSSINSMS |
| 76 | 6H2 | GRTLSRYAMG |
| 77 | 5D2 | GSIFSPNAMI |
| 78 | 7C4 | GATSAITNLG |
| 79 | 5F2 | GSTFRIRVMR |
| 80 | 2C2 | GDTSKFKAVG |
| 81 | 5G2 | GSTFGNKPMG |
| 82 | 9H2 | GSTSSINTMY |
| 83 | 5D4 | GRTDRITTMG |
| 84 | 2A4 | GRTIGINDMA |
| 85 | 7F1 | AIGSINSMS |
| 86 | 5C2 | GSTSSINTMY |
| 87 | 2F4 | TTFSINSMS |
| 88 | 2A2 | GSTFSIRAMR |
| 89 | 11F3 | GRTSTIDTMY |
| 90 | 10B3 | GSTSSINTMY |
| 91 | MH1 | GGDWSANFMY |
| 92 | MH2 | GGDWSANFMY |
| 93 | MH3 | GSTSSINTMY |
| 94 | MH4 | GSTSSINTMY |
| 95 | MH5 | GSTSSINTMY |
| 96 | MH6 | GSTFSIRAMR |
| 97 | MH7 | GSTFSIRAMR |
| 98 | MH8 | GSTFSIRAMR |
| 99 | MH9 | GRTSTIDTMY |
| 100 | MH10 | GRTSTIDTMY |
| 101 | MH11 | GRTSTIDTMY |

CDR2 sequences for various exemplary MSLN binding domains of this disclosure

| Sequence ID No. | Exemplary MSLN binding domain | CDR2 Sequence |
|---|---|---|
| 102 | 9B1 | TMNPDGFPNYADAVKGRFT |
| 103 | 9F3 | ALTSGGRANYADSVKGRFT |
| 104 | 7H2 | SISSDGRTSYADSVRGRFT |
| 105 | 3B4 | VITRGGYAIYLDAVKGRFT |
| 106 | 4A2 | VISRGGSTNYADSVKGRFT |
| 107 | 12D1 | TIDQLGRTNYADSVKGRFA |
| 108 | 3G1 | SISSSGDFTYTDSVKGRFT |
| 109 | 2A1 | FVSKDGKRILYLDSVRGRFT |
| 110 | 6F3 | FVSKDGKRILYLDSVRGRFT |
| 111 | 1H2 | SISGSGSDTLYADSVKGRFT |
| 112 | 3F2 | DISPVGNTNYADSVKGRFT |
| 113 | 12C2 | SHTSTGYVYYRDSVKGRFT |
| 114 | 2D1 | VITDRGSTSYADSVKGRFT |
| 115 | 6H2 | AISRSGGTTRYSDSVKGRFT |
| 116 | 5D2 | SINSSGSTNYGDSVKGRFT |
| 117 | 7C4 | RISVREDKEDYEDSVKGRFT |
| 118 | 5F2 | VISGSSTYYADSVKGRFT |
| 119 | 2C2 | WINNSGVGNTAESVKGRFT |
| 120 | 5G2 | VISSDGGSTRYAALVKGRFT |
| 121 | 9H2 | FISSGGSTNVRDSVKGRFS |
| 122 | 5D4 | TISNRGTSNYANSVKGRFT |
| 123 | 2A4 | TITKGGTTDYADSVDGRFT |
| 124 | 7F1 | VITDRGSTSYADSVKGRFT |
| 125 | 5C2 | TINRGGSTNVRDSVKGRFS |
| 126 | 2F4 | VITNRGTTSYADSVKGRFT |
| 127 | 2A2 | VIYGSSTYYADAVKGRFT |
| 128 | 11F3 | YVTSRGTSNVADSVKGRFT |
| 129 | 10B3 | FISSGGSTNVRDSVKGRFS |
| 130 | MH1 | RISGRGVVDYVESVKGRFT |
| 131 | MH2 | RISGRGVVDYVESVKGRFT |
| 132 | MH3 | FISSGGSTNVRDSVKGRFT |
| 133 | MH4 | FISSGGSTNVRDSVKGRFT |
| 134 | MH5 | FISSGGSTNVRDSVKGRFT |
| 135 | MH6 | VIYGSSTYYADAVKGRFT |
| 136 | MH7 | VIYGSSTYYADAVKGRFT |
| 137 | MH8 | VIYGSSTYYADAVKGRFT |
| 138 | MH9 | YVTSRGTSNVADSVKGRFT |

| CDR2 sequences for various exemplary MSLN binding domains of this disclosure | | |
|---|---|---|
| Sequence ID No. | Exemplary MSLN binding domain | CDR2 Sequence |
| 139 | MH10 | YVTSRGTSNVADSVKGRFT |
| 140 | MH11 | YVTSRGTSNVADSVKGRFT |

| CDR3 sequences for various exemplary MSLN binding domains of this disclosure | | |
|---|---|---|
| Sequence ID No. | Exemplary MSLN binding domain | CDR3 Sequence |
| 141 | 9B1 | GPY |
| 142 | 9F3 | GRFKGDYAQRSGMDY |
| 143 | 7H2 | QRSGVRAF |
| 144 | 3B4 | DRVEGTSGGPQLRDY |
| 145 | 4A2 | RTYTRHDY |
| 146 | 12D1 | GGGPLGSRWLRGRH |
| 147 | 3G1 | RRTYLPRRFGS |
| 148 | 2A1 | APGAARNY |
| 149 | 6F3 | APGAARNV |
| 150 | 1H2 | GGSLSRSS |
| 151 | 3F2 | VRGWLDERPGPGPIVY |
| 152 | 12C2 | NRGSYEY |
| 153 | 2D1 | IADWRGY |
| 154 | 6H2 | RRRGWGRTLEY |
| 155 | 5D2 | SDFRRGTQY |
| 156 | 7C4 | QRWGRGPGTT |
| 157 | 5F2 | DDSGIARDY |
| 158 | 2C2 | YRRFGINKNY |
| 159 | 5G2 | LRTYYLNDPVVFS |
| 160 | 9H2 | YIPLRGTLHDY |
| 161 | 5D4 | RKWGRNY |
| 162 | 2A4 | KRREWAKDFEY |
| 163 | 7F1 | IADWRGY |
| 164 | 5C2 | YIPYGGTLHDF |
| 165 | 2F4 | IADWRGY |
| 166 | 2A2 | DTIGTARDY |
| 167 | 11F3 | RTTSYPVDF |
| 168 | 10B3 | YIPYGGTLHDF |
| 169 | MH1 | ASY |
| 170 | MH2 | ASY |
| 171 | MH3 | YIPYGGTLHDF |
| 172 | MH4 | YIPYGGTLHDF |
| 173 | MH5 | YIPYGGTLHDF |
| 174 | MH6 | DTIGTARDY |
| 175 | MH7 | DTIGTARDY |
| 176 | MH8 | DTIGTARDY |
| 177 | MH9 | RTTSYPVDF |
| 178 | MH10 | RTTSYPVDF |
| 179 | MH11 | RTTSYPVDF |

| Framework region 1 (f1) sequences for various exemplary MSLN binding domains | | |
|---|---|---|
| Sequence ID No. | Exemplary MSLN binding domain | Framework 1 |
| 180 | 9B1 | QVQLVESGGGLVQPGGSLRLSCAAS |
| 181 | 9F3 | QVQLVESGGGLVQAGGSLRLSCAAS |
| 182 | 7H2 | QVQLVESGGGLVQAGGSLRLSCAFS |
| 183 | 3B4 | QVQLVESGGGLVQAGGSLRLSCVAS |
| 184 | 4A2 | QVQLVESGGGLVQAGGSLRLSCAAS |
| 185 | 12D1 | QVRLVESGGGLVQAGGSLRLSCAAS |
| 186 | 3G1 | QVRLVESGGGLVQAGESLRLSCAAS |
| 187 | 2A1 | QVQPVESGGGLVQPGGSLRLSCVVS |
| 188 | 6F3 | QVQPVESGGGLVQPGGSLRLSCVVS |
| 189 | 1H2 | EVQLVESGGGLVQPGNSLRLSCAAS |
| 190 | 3F2 | QVQIVESGGGLVQAGGSLRLSCVAS |
| 191 | 12C2 | QVQLVESGGGLVQTGGSLRLSCAAS |
| 192 | 2D1 | QVQLVESGGGLVQAGGSLRLSCAAS |
| 193 | 6H2 | QVQLVESGGGLVQAGGSLRLSCAAS |
| 194 | 5D2 | QVQLGESGGGLVQAGGSLRLSCAAS |
| 195 | 7C4 | QVQLVESGGGLVPSGGSLRLSCAAS |
| 196 | 5F2 | QVQLVESGGGLVQAGGSLRLSCAAS |
| 197 | 2C2 | QVQLVESGGGLVQAGESRRLSCAVS |
| 198 | 5G2 | QVQLVESGGGLVQAGGSLRLSCAAS |
| 199 | 9H2 | QVQLVESGGGLVQAGGSLRLSCAAS |
| 200 | 5D4 | QVQLVESGGGLVQAGGSLRLSCVAS |
| 201 | 2A4 | QVQLVESGGGLVQARGSLRLSCTAS |

| Framework region 1 (f1) sequences for various exemplary MSLN binding domains | | |
|---|---|---|
| Sequence ID No. | Exemplary MSLN binding domain | Framework 1 |
| 202 | 7F1 | QVQLVESGGGLVQAGGSLRLSCAAS |
| 203 | 5C2 | QVQLVESGGGLVQAGGSLRLSCAAS |
| 204 | 2F4 | QVQLVESGGGLVQAGGSLRLSCTTS |
| 205 | 2A2 | QVQLVESGGGLVQAGGSLTLSCAAS |
| 206 | 11F3 | QVQLVESGGGLVQAGGSLRLSCVAS |
| 207 | 10B3 | QVQLVESGGGLVQAGGSLRLSCAAS |
| 208 | MH1 | EVQLVESGGGLVQPGGSLRLSCAAS |
| 209 | MH2 | EVQLVESGGGLVQPGGSLRLSCAAS |
| 210 | MH3 | EVQLVESGGGLVQAGGSLRLSCAAS |
| 211 | MH4 | EVQLVESGGGLVQPGGSLRLSCAAS |
| 212 | MH5 | EVQLVESGGGLVQPGGSLRLSCAAS |
| 213 | MH6 | QVQLVESGGGVVQAGGSLRLSCAAS |
| 214 | MH7 | QVQLVESGGGVVQPGGSLRLSCAAS |
| 215 | MH8 | QVQLVESGGGVVQPGGSLRLSCAAS |
| 216 | MH9 | EVQLVESGGGLVQAGGSLRLSCVAS |
| 217 | MH10 | EVQLVESGGGLVQPGGSLRLSCAAS |
| 218 | MH11 | EVQLVESGGGLVQPGGSLRLSCAAS |

| Framework region 2 (f2) sequences for various exemplary MSLN binding domains | | |
|---|---|---|
| Sequence ID No. | Exemplary MSLN binding domain | Framework 2 |
| 219 | 9B1 | WYRQAGNNRALVA |
| 220 | 9F3 | WYRQAPGKQRELVA |
| 221 | 7H2 | WYRQAPGKQRTVVA |
| 222 | 3B4 | WYRQAPGKERELVA |
| 223 | 4A2 | WYRQAPGKQRELVA |
| 224 | 12D1 | WYRQDPSKQREWVA |
| 225 | 3G1 | WYRQAPGKQRELVA |
| 226 | 2A1 | WYRQASGKERESVA |
| 227 | 6F3 | WYRQASGKERESVA |
| 228 | 1H2 | WVRQAPGKGLEWVS |
| 229 | 3F2 | WYRQAPGKEREMVA |
| 230 | 12C2 | WFRQAPGKQREWVA |
| 231 | 2D1 | WYRQAQGKQREPVA |
| 232 | 6H2 | WFRQAPGKERQFVA |
| 233 | 5D2 | WHRQAPGKQREPVA |
| 234 | 7C4 | WYRRAPGQVREMVA |
| 235 | 5F2 | WYRQAPGTERDLVA |
| 236 | 2C2 | WYRQAPGAQRELLA |
| 237 | 5G2 | WYRQAPGKQRELVA |
| 238 | 9H2 | WYRQAPGKERELVA |
| 239 | 5D4 | WYRQAPGKQRELVA |
| 240 | 2A4 | WYRQAPGNQRELVA |
| 241 | 7F1 | WYRQAPGKQREPVA |
| 242 | 5C2 | WFRQAPGEERELVA |
| 243 | 2F4 | WYRQAPGNQREPVA |
| 244 | 2A2 | WYRQAPGTERDLVA |
| 245 | 11F3 | WHRQAPGNERELVA |
| 246 | 10B3 | WYRQAPGKERELVA |
| 247 | MH1 | WYRQAPGKQRELVA |
| 248 | MH2 | WVRQAPGKGLEWVS |
| 249 | MH3 | WYRQAPGKERELVA |
| 250 | MH4 | WYRQAPGKERELVA |
| 251 | MH5 | WVRQAPGKGLEWVS |
| 252 | MH6 | WYRQAPGTERDLVA |
| 253 | MH7 | WYRQAPGKERELVA |
| 254 | MH8 | WVRQAPGKGLEWVS |
| 255 | MH9 | WHRQAPGNERELVA |
| 256 | MH10 | WHRQAPGKERELVA |
| 257 | MH11 | WVRQAPGKGLEWVS |

| Framework region 3 (f3) sequences for various exemplary MSLN binding domains | | |
|---|---|---|
| Sequence ID No. | Exemplary MSLN binding domain | Framework 3 |
| 258 | 9B1 | ISWDIAENTVYLQMNSLNSEDTTVYYCNS |
| 259 | 9F3 | ISGDNVRNMVYLQMNSLKPEDTAIYYCSA |
| 260 | 7H2 | ISGENGKNTVYLQMNSLKLEDTAVYYCLG |
| 261 | 3B4 | ISRDNANNAIYLEMNSLKPEDTAVYVCNA |
| 262 | 4A2 | ISRDNAENTVSLQMNTLKPEDTAVYFCNA |

Framework region 3 (f3) sequences for various exemplary MSLN binding domains

| Sequence ID No. | Exemplary MSLN binding domain | Framework 3 |
|---|---|---|
| 263 | 12D1 | ISKDSTRNTVYLQMNMLRPEDTAVYYCNA |
| 264 | 3G1 | ISRDNAKNTVYLQMNSLKPEDTAVYYCNA |
| 265 | 2A1 | ISRDIDKKTVYLQMDNLKPEDTGVYYCNS |
| 266 | 6F3 | ISRDIYKKTVYLQMDNLKPEDTGVYYCNS |
| 267 | 1H2 | ISRDNAKTTLYLQMNSLRPEDTAVYYCTI |
| 268 | 3F2 | ISKENAKNTVYLQMNSLKPEDTAVYYCHI |
| 269 | 12C2 | ISRDNAKSTVYLQMNSLKPEDTAIYYCKA |
| 270 | 2D1 | ISRDNAKNTVYLQMNSLKPEDTAIYTCHV |
| 271 | 6H2 | ISRDNAANTFYLQMNNLRPDDTAVYYCNV |
| 272 | 5D2 | VSRDIVKNTMYLQMNSLKPEDTAVYYCSY |
| 273 | 7C4 | ISRDNTQNLVYLQMNNLQPHDTAIYYCGA |
| 274 | 5F2 | ISRDNAKNTLYLQMNNLKPEDTAVYYCNA |
| 275 | 2C2 | ISRDNAKNTVYLQMNRLTPEDTDVYYCRF |
| 276 | 5G2 | ISRDNAKNTVYLQMESLVAEDTAVYYCNA |
| 277 | 9H2 | VSRDSAKNIVYLQMNSLTPEDTAVYYCNT |
| 278 | 5D4 | ISRDNAKNTVYLQMNSLKPEDTAVYYCNA |
| 279 | 2A4 | ISRDNAKNTVYLQMNSLKPEDTAVYYCNT |
| 280 | 7F1 | ISRDNAKNTVYLQMNSLKPEDTAIYTCHV |
| 281 | 5C2 | VSRDSAKNIVYLQMNRLKPEDTAVYYCNT |
| 282 | 2F4 | ISRDNARNTVYLQMDSLKPEDTAIYTCHV |
| 283 | 2A2 | ISRDNAKNTLYLQMNNLKPEDTAVYYCNA |
| 284 | 11F3 | ISRDNAKNTAYLQMNSLKPEDTAVYYCSV |
| 285 | 10B3 | VSRDSAKNIVYLQMNSLKPEDTAVYYCNT |
| 286 | MH1 | ISRDNSKNTLYLQMNSLRAEDTAVYYCAV |
| 287 | MH2 | ISRDNSKNTLYLQMNSLRAEDTAVYYCAV |
| 288 | MH3 | ISRDNSKNTLYLQMNSLRAEDTAVYYCNT |
| 289 | MH4 | ISRDNSKNTLYLQMNSLRAEDTAVYYCNT |
| 290 | MH5 | ISRDNSKNTLYLQMNSLRAEDTAVYYCNT |
| 291 | MH6 | ISRDNSKNTLYLQMNSLRAEDTAVYYCNA |
| 292 | MH7 | ISRDNSKNTLYLQMNSLRAEDTAVYYCNA |
| 293 | MH8 | ISRDNSKNTLYLQMNSLRAEDTAVYYCNA |
| 294 | MH9 | ISRDNSKNTLYLQMNSLRAEDTAVYYCSV |
| 295 | MH10 | ISRDNSKNTLYLQMNSLRAEDTAVYYCSV |
| 296 | MH11 | ISRDNSKNTLYLQMNSLRAEDTAVYYCSV |

Framework region 4 (f4) sequences for various exemplary MSLN binding domains

| Sequence ID No. | Exemplary MSLN binding domain | Framework 4 |
|---|---|---|
| 297 | 9B1 | WGQGTQVTVSS |
| 298 | 9F3 | WGKGTLVTVSS |
| 299 | 7H2 | WGQGTQVTVSS |
| 300 | 3B4 | FGQGTQVTVSS |
| 301 | 4A2 | WGQGTQVTVSS |
| 302 | 12D1 | WGQGTQVTVSS |
| 303 | 3G1 | WGQGTQVTVSS |
| 304 | 2A1 | WGQGTQVTVSS |
| 305 | 6F3 | WGQGTQVTVSS |
| 306 | 1H2 | QGTLVTVSS |
| 307 | 3F2 | WGQGTQVTVSS |
| 308 | 12C2 | WGQGTQVTVSS |
| 309 | 2D1 | WGQGTQVTVSS |
| 310 | 6H2 | WGQGTQVTVSS |
| 311 | 5D2 | WGQGTQVTVSS |
| 312 | 7C4 | WGQGTQVTVSS |
| 313 | 5F2 | WGQGTQVTVSS |
| 314 | 2C2 | WGQGTQVTVSS |
| 315 | 5G2 | WGQGTQVTVSS |
| 316 | 9H2 | WGQGTQVTVSS |
| 317 | 5D4 | WGQGTQVTVSS |
| 318 | 2A4 | WGQGTQVTVSS |
| 319 | 7F1 | WGQGTQVTVSS |
| 320 | 5C2 | WGQGTQVTVSS |
| 321 | 2F4 | WGQGTQVTVSS |
| 322 | 2A2 | WGQGTQVTVSS |
| 323 | 11F3 | WGQGTQVTVSS |
| 324 | 10B3 | WGQGTQVTVSS |
| 325 | MH1 | WGQGTLVTVSS |
| 326 | MH2 | WGQGTLVTVSS |
| 327 | MH3 | WGQGTLVTVSS |
| 328 | MH4 | WGQGTLVTVSS |
| 329 | MH5 | WGQGTLVTVSS |
| 330 | MH6 | WGQGTLVTVSSGG |
| 331 | MH7 | WGQGTLVTVSSGG |

| Framework region 4 (f4) sequences for various exemplary MSLN binding domains | | |
|---|---|---|
| Sequence ID No. | Exemplary MSLN binding domain | Framework 4 |
| 332 | MH8 | WGQGTLVTVSSGG |
| 333 | MH9 | WGQGTLVTVS |
| 334 | MH10 | WGQGTLVTVSS |
| 335 | MH11 | WGQGTLVTVSS |

What is claimed is:

1. A single domain mesothelin binding protein, wherein said protein comprises the following formula:

f1-r1-f2-r2-f3-r3-f4 wherein, r1 is CDR1; r2 is CDR2; and r3 CDR3; and wherein f1, f2, f3 and f4 are framework residues, and wherein:
(i) the CDR1 comprises the sequence GSTFSIRAMR (SEQ ID Nos.: 88, and 96-98), the CDR2 comprises the sequence VIYGSSTYYADAVKGRFT (SEQ ID Nos.: 127, 135-137), and the CDR3 comprises the sequence DTIGTARDY (SEQ ID Nos.: 166, 174-176);
(ii) the CDR1 comprises the sequence GRTSTIDTMY (SEQ ID Nos.: 89, 99-101), the CDR2 comprises YVTSRGTSNVADSVKGRFT (SEQ ID Nos.: 128, 138-140), and the CDR3 comprises the sequence RTTSYPVDF (SEQ ID Nos.: 167, 177-179);
(iii) the CDR1 comprises the sequence GSTSSINTMY (SEQ ID Nos.: 82, 86, 90, 93-95), the CDR2 comprises the sequence FISSGGSTNVRDSVKGRFT (SEQ ID Nos. 132-134), the CDR3 comprises the sequence YIPYGGTLHDF (SEQ ID Nos.: 164, 168, 171-173);
(iv) the CDR1 comprises the sequence GGDWSANFMY (SEQ ID Nos.: 54, 91-92), the CDR2 comprises the sequence RISGRGVVDYVESVKGRFT (SEQ ID Nos.: 130-131), the CDR3 comprises the sequence ASY (SEQ ID Nos.: 169-170); or
(v) the CDR1 comprises the sequence GSTFRIRVMR (SEQ ID NO: 79), the CDR2 comprises the sequence VISGSSTYYADSVKGRFT (SEQ ID NO: 118), and the CDR3 comprises the sequence DDSGIARDY (SEQ ID NO: 157).

2. The single domain mesothelin binding protein of claim 1, wherein said protein binds to an epitope of mesothelin, wherein said epitope is located in region I, comprising amino acid residues 296-390 of SEQ ID NO: 57, region II comprising amino acid residue 391-486 of SEQ ID NO: 57, or region III comprising amino acid residues 487-598 of SEQ ID NO: 57.

3. The single domain mesothelin binding protein of claim 1, wherein said protein comprises an amino acid sequence as set forth in any one of SEQ ID Nos.: 17, 26, 27, 32-40, 58 and 60-62.

4. The single domain mesothelin binding protein of claim 1, wherein f1 comprises a sequence as set forth in any one of SEQ ID Nos.: 196, 205, and 208-218.

5. The single domain mesothelin binding protein of claim 1, wherein f2 comprises a sequence as set forth in any one of SEQ ID Nos.: 235, 244 and 247-257.

6. The single domain mesothelin binding protein of claim 1, wherein f3 comprises a sequence as set forth in any one of SEQ ID Nos.: 274, 283, and 286-296.

7. The single domain mesothelin binding protein of claim 1, wherein f4 comprises a sequence as set forth in any one of SEQ ID Nos.: 313, 322, and 325-335.

8. A single domain mesothelin binding protein comprising an amino acid sequence as set forth in any one of SEQ ID Nos.: 17, 26, 27, 32-40, 58 and 60-62.

9. A method for the treatment or amelioration of a proliferative disease, or a tumorous disease, that expresses mesothelin comprising the administration of the single domain mesothelin binding protein of claim 1 to a subject in need thereof.

10. The method of claim 9, comprising administering the single domain mesothelin binding protein at a dose of up to 10 mg/kg.

11. The method of claim 10, wherein the single domain mesothelin binding protein is administered once a week, twice per week, every other day, or every three weeks.

12. The method of claim 11, wherein the subject is human.

13. The method of claim 9, wherein the method further comprises administration of an agent in combination with the single domain mesothelin binding protein.

14. The method of claim 9, wherein the single domain mesothelin binding protein selectively binds to tumor cells expressing mesothelin.

15. The method of claim 14, wherein the single domain mesothelin binding protein mediates T cell killing of tumor cells expressing mesothelin.

16. The method of claim 15, wherein the tumorous disease comprises a solid tumor disease.

17. The method of claim 16, wherein the solid tumor disease comprises mesothelioma, lung cancer, gastric cancer, ovarian cancer, or triple negative breast cancer.

18. The method of claim 17, wherein the solid tumor disease is metastatic.

* * * * *

SEQUENCE LISTING

```
<160> NUMBER OF SEQ ID NOS: 336

<210> SEQ ID NO 1
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Val Arg
            20                  25                  30

Gly Met Ala Trp Tyr Arg Gln Ala Gly Asn Asn Arg Ala Leu Val Ala
        35                  40                  45

Thr Met Asn Pro Asp Gly Phe Pro Asn Tyr Ala Asp Ala Val Lys Gly
    50                  55                  60

Arg Phe Thr Ile Ser Trp Asp Ile Ala Glu Asn Thr Val Tyr Leu Gln
65                  70                  75                  80

Met Asn Ser Leu Asn Ser Glu Asp Thr Thr Val Tyr Tyr Cys Asn Ser
                85                  90                  95

Gly Pro Tyr Trp Gly Gln Gly Thr Gln Val Thr Val Ser Ser
            100                 105                 110

<210> SEQ ID NO 2
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Pro Ser Ile Glu
            20                  25                  30

Gln Met Gly Trp Tyr Arg Gln Ala Pro Gly Lys Gln Arg Glu Leu Val
        35                  40                  45

Ala Ala Leu Thr Ser Gly Gly Arg Ala Asn Tyr Ala Asp Ser Val Lys
    50                  55                  60

Gly Arg Phe Thr Ile Ser Gly Asp Asn Val Arg Asn Met Val Tyr Leu
65                  70                  75                  80

Gln Met Asn Ser Leu Lys Pro Glu Asp Thr Ala Ile Tyr Tyr Cys Ser
                85                  90                  95
```

Ala Gly Arg Phe Lys Gly Asp Tyr Ala Gln Arg Ser Gly Met Asp Tyr
            100                 105                 110

Trp Gly Lys Gly Thr Leu Val Thr Val Ser Ser
        115                 120

<210> SEQ ID NO 3
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Val Glu Ser Gly Gly Gly Leu Val Gln Ala Gly Gly
1               5                   10                  15

Ser Leu Arg Leu Ser Cys Ala Phe Ser Gly Thr Thr Tyr Thr Phe Asp
            20                  25                  30

Leu Met Ser Trp Tyr Arg Gln Ala Pro Gly Lys Gln Arg Thr Val Val
        35                  40                  45

Ala Ser Ile Ser Ser Asp Gly Arg Thr Ser Tyr Ala Asp Ser Val Arg
    50                  55                  60

Gly Arg Phe Thr Ile Ser Gly Glu Asn Gly Lys Asn Thr Val Tyr Leu
65                  70                  75                  80

Gln Met Asn Ser Leu Lys Leu Glu Asp Thr Ala Val Tyr Tyr Cys Leu
                85                  90                  95

Gly Gln Arg Ser Gly Val Arg Ala Phe Trp Gly Gln Gly Thr Gln Val
            100                 105                 110

Thr Val Ser Ser
        115

<210> SEQ ID NO 4
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Val Gln Leu Val Glu Ser Gly Gly Gly Leu Val Gln Ala Gly Gly
1               5                   10                  15

Ser Leu Arg Leu Ser Cys Val Ala Ser Gly Ser Thr Ser Asn Ile Asn
            20                  25                  30

Asn Met Arg Trp Tyr Arg Gln Ala Pro Gly Lys Glu Arg Glu Leu Val
        35                  40                  45

Ala Val Ile Thr Arg Gly Gly Tyr Ala Ile Tyr Leu Asp Ala Val Lys
    50                  55                  60

Gly Arg Phe Thr Ile Ser Arg Asp Asn Ala Asn Asn Ala Ile Tyr Leu
65                  70                  75                  80

Glu Met Asn Ser Leu Lys Pro Glu Asp Thr Ala Val Tyr Val Cys Asn
                85                  90                  95

Ala Asp Arg Val Glu Gly Thr Ser Gly Gly Pro Gln Leu Arg Asp Tyr
            100                 105                 110

Phe Gly Gln Gly Thr Gln Val Thr Val Ser Ser
        115                 120

<210> SEQ ID NO 5
<211> LENGTH: 116

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Thr Phe Gly Ile Asn
            20                  25                  30

Ala Met Gly Trp Tyr Arg Gln Ala Pro Gly Lys Gln Arg Glu Leu Val
        35                  40                  45

Ala Val Ile Ser Arg Gly Gly Ser Thr Asn Tyr Ala Asp Ser Val Lys
    50                  55                  60

Gly Arg Phe Thr Ile Ser Arg Asp Asn Ala Glu Asn Thr Val Ser Leu
65                  70                  75                  80

Gln Met Asn Thr Leu Lys Pro Glu Asp Thr Ala Val Tyr Phe Cys Asn
                85                  90                  95

Ala Arg Thr Tyr Thr Arg His Asp Tyr Trp Gly Gln Gly Thr Gln Val
            100                 105                 110

Thr Val Ser Ser
        115

<210> SEQ ID NO 6
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Val Arg Leu Val Glu Ser Gly Gly Gly Leu Val Gln Ala Gly Gly
1               5                   10                  15

Ser Leu Arg Leu Ser Cys Ala Ala Ser Ile Ser Ala Phe Arg Leu Met
            20                  25                  30

Ser Val Arg Trp Tyr Arg Gln Asp Pro Ser Lys Gln Arg Glu Trp Val
        35                  40                  45

Ala Thr Ile Asp Gln Leu Gly Arg Thr Asn Tyr Ala Asp Ser Val Lys
    50                  55                  60

Gly Arg Phe Ala Ile Ser Lys Asp Ser Thr Arg Asn Thr Val Tyr Leu
65                  70                  75                  80

Gln Met Asn Met Leu Arg Pro Glu Asp Thr Ala Val Tyr Tyr Cys Asn
                85                  90                  95

Ala Gly Gly Gly Pro Leu Gly Ser Arg Trp Leu Arg Gly Arg His Trp
            100                 105                 110

Gly Gln Gly Thr Gln Val Thr Val Ser Ser
        115                 120

<210> SEQ ID NO 7
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Arg Leu Val Glu Ser Gly Gly Gly Leu Val Gln Ala Gly Glu
```

```
1               5                   10                  15
Ser Leu Arg Leu Ser Cys Ala Ala Ser Gly Arg Pro Phe Ser Ile Asn
            20                  25                  30

Thr Met Gly Trp Tyr Arg Gln Ala Pro Gly Lys Gln Arg Glu Leu Val
        35                  40                  45

Ala Ser Ile Ser Ser Ser Gly Asp Phe Thr Tyr Thr Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Arg Arg Thr Tyr Leu Pro Arg Arg Phe Gly Ser Trp Gly Gln Gly
            100                 105                 110

Thr Gln Val Thr Val Ser Ser
        115
```

<210> SEQ ID NO 8
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Gln Val Gln Pro Val Glu Ser Gly Gly Gly Leu Val Gln Pro Gly Gly
1               5                   10                  15

Ser Leu Arg Leu Ser Cys Val Val Ser Gly Ser Asp Phe Thr Glu Asp
            20                  25                  30

Ala Met Ala Trp Tyr Arg Gln Ala Ser Gly Lys Glu Arg Glu Ser Val
        35                  40                  45

Ala Phe Val Ser Lys Asp Gly Lys Arg Ile Leu Tyr Leu Asp Ser Val
    50                  55                  60

Arg Gly Arg Phe Thr Ile Ser Arg Asp Ile Asp Lys Lys Thr Val Tyr
65                  70                  75                  80

Leu Gln Met Asp Asn Leu Lys Pro Glu Asp Thr Gly Val Tyr Tyr Cys
                85                  90                  95

Asn Ser Ala Pro Gly Ala Ala Arg Asn Tyr Trp Gly Gln Gly Thr Gln
            100                 105                 110

Val Thr Val Ser Ser
        115
```

<210> SEQ ID NO 9
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Gln Val Gln Pro Val Glu Ser Gly Gly Gly Leu Val Gln Pro Gly Gly
1               5                   10                  15

Ser Leu Arg Leu Ser Cys Val Val Ser Gly Ser Asp Phe Thr Glu Asp
            20                  25                  30

Ala Met Ala Trp Tyr Arg Gln Ala Ser Gly Lys Glu Arg Glu Ser Val
        35                  40                  45

Ala Phe Val Ser Lys Asp Gly Lys Arg Ile Leu Tyr Leu Asp Ser Val
```

-continued

```
                    50                  55                  60
Arg Gly Arg Phe Thr Ile Ser Arg Asp Ile Tyr Lys Lys Thr Val Tyr
 65                  70                  75                  80

Leu Gln Met Asp Asn Leu Lys Pro Glu Asp Thr Gly Val Tyr Tyr Cys
                     85                  90                  95

Asn Ser Ala Pro Gly Ala Ala Arg Asn Val Trp Gly Gln Gly Thr Gln
                100                 105                 110

Val Thr Val Ser Ser
            115

<210> SEQ ID NO 10
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Val Gln Leu Val Glu Ser Gly Gly Gly Leu Val Gln Pro Gly Asn
  1               5                  10                  15

Ser Leu Arg Leu Ser Cys Ala Ala Ser Gly Phe Thr Phe Ser Ser Phe
                 20                  25                  30

Gly Met Ser Trp Val Arg Gln Ala Pro Gly Lys Gly Leu Glu Trp Val
             35                  40                  45

Ser Ser Ile Ser Gly Ser Gly Ser Asp Thr Leu Tyr Ala Asp Ser Val
         50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Val Tyr Tyr Cys
                     85                  90                  95

Thr Ile Gly Gly Ser Leu Ser Arg Ser Ser Gln Gly Thr Leu Val Thr
                100                 105                 110

Val Ser Ser
        115

<210> SEQ ID NO 11
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Ile Val Glu Ser Gly Gly Gly Leu Val Gln Ala Gly Gly
  1               5                  10                  15

Ser Leu Arg Leu Ser Cys Val Ala Ser Gly Leu Thr Tyr Ser Ile Val
                 20                  25                  30

Ala Val Gly Trp Tyr Arg Gln Ala Pro Gly Lys Glu Arg Glu Met Val
             35                  40                  45

Ala Asp Ile Ser Pro Val Gly Asn Thr Asn Tyr Ala Asp Ser Val Lys
         50                  55                  60

Gly Arg Phe Thr Ile Ser Lys Glu Asn Ala Lys Asn Thr Val Tyr Leu
 65                  70                  75                  80

Gln Met Asn Ser Leu Lys Pro Glu Asp Thr Ala Val Tyr Tyr Cys His
                     85                  90                  95

Ile Val Arg Gly Trp Leu Asp Glu Arg Pro Gly Pro Gly Pro Ile Val
```

```
                     100                 105                 110
Tyr Trp Gly Gln Gly Thr Gln Val Thr Val Ser Ser
            115                 120

<210> SEQ ID NO 12
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Val Glu Ser Gly Gly Gly Leu Val Gln Thr Gly Gly
1               5                   10                  15

Ser Leu Arg Leu Ser Cys Ala Ala Ser Gly Leu Thr Phe Gly Val Tyr
            20                  25                  30

Gly Met Glu Trp Phe Arg Gln Ala Pro Gly Lys Gln Arg Glu Trp Val
        35                  40                  45

Ala Ser His Thr Ser Thr Gly Tyr Val Tyr Tyr Arg Asp Ser Val Lys
    50                  55                  60

Gly Arg Phe Thr Ile Ser Arg Asp Asn Ala Lys Ser Thr Val Tyr Leu
65                  70                  75                  80

Gln Met Asn Ser Leu Lys Pro Glu Asp Thr Ala Ile Tyr Tyr Cys Lys
                85                  90                  95

Ala Asn Arg Gly Ser Tyr Glu Tyr Trp Gly Gln Gly Thr Gln Val Thr
            100                 105                 110

Val Ser Ser
        115

<210> SEQ ID NO 13
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Glu Ser Gly Gly Gly Leu Val Gln Ala Gly Gly
1               5                   10                  15

Ser Leu Arg Leu Ser Cys Ala Ala Ser Thr Thr Ser Ser Ile Asn Ser
            20                  25                  30

Met Ser Trp Tyr Arg Gln Ala Gln Gly Lys Gln Arg Glu Pro Val Ala
        35                  40                  45

Val Ile Thr Asp Arg Gly Ser Thr Ser Tyr Ala Asp Ser Val Lys Gly
    50                  55                  60

Arg Phe Thr Ile Ser Arg Asp Asn Ala Lys Asn Thr Val Tyr Leu Gln
65                  70                  75                  80

Met Asn Ser Leu Lys Pro Glu Asp Thr Ala Ile Tyr Thr Cys His Val
                85                  90                  95

Ile Ala Asp Trp Arg Gly Tyr Trp Gly Gln Gly Thr Gln Val Thr Val
            100                 105                 110

Ser Ser

<210> SEQ ID NO 14
<211> LENGTH: 120
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 14

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Leu Ser Arg Tyr
            20                  25                  30

Ala Met Gly Trp Phe Arg Gln Ala Pro Gly Lys Glu Arg Gln Phe Val
        35                  40                  45

Ala Ala Ile Ser Arg Ser Gly Gly Thr Thr Arg Tyr Ser Asp Ser Val
    50                  55                  60

Lys Gly Arg Phe Thr Ile Ser Arg Asp Asn Ala Ala Asn Thr Phe Tyr
65                  70                  75                  80

Leu Gln Met Asn Asn Leu Arg Pro Asp Asp Thr Ala Val Tyr Tyr Cys
                85                  90                  95

Asn Val Arg Arg Arg Gly Trp Gly Arg Thr Leu Glu Tyr Trp Gly Gln
            100                 105                 110

Gly Thr Gln Val Thr Val Ser Ser
        115                 120
```

<210> SEQ ID NO 15
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Gln Val Gln Leu Gly Glu Ser Gly Gly Gly Leu Val Gln Ala Gly Gly
1               5                   10                  15

Ser Leu Arg Leu Ser Cys Ala Ala Ser Gly Ser Ile Phe Ser Pro Asn
            20                  25                  30

Ala Met Ile Trp His Arg Gln Ala Pro Gly Lys Gln Arg Glu Pro Val
        35                  40                  45

Ala Ser Ile Asn Ser Ser Gly Ser Thr Asn Tyr Gly Asp Ser Val Lys
    50                  55                  60

Gly Arg Phe Thr Val Ser Arg Asp Ile Val Lys Asn Thr Met Tyr Leu
65                  70                  75                  80

Gln Met Asn Ser Leu Lys Pro Glu Asp Thr Ala Val Tyr Tyr Cys Ser
                85                  90                  95

Tyr Ser Asp Phe Arg Arg Gly Thr Gln Tyr Trp Gly Gln Gly Thr Gln
            100                 105                 110

Val Thr Val Ser Ser
        115
```

<210> SEQ ID NO 16
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Gln Val Gln Leu Val Glu Ser Gly Gly Gly Leu Val Pro Ser Gly Gly
1               5                   10                  15
```

Ser Leu Arg Leu Ser Cys Ala Ala Ser Gly Ala Thr Ser Ala Ile Thr
            20                  25                  30

Asn Leu Gly Trp Tyr Arg Arg Ala Pro Gly Gln Val Arg Glu Met Val
        35                  40                  45

Ala Arg Ile Ser Val Arg Glu Asp Lys Glu Asp Tyr Glu Asp Ser Val
    50                  55                  60

Lys Gly Arg Phe Thr Ile Ser Arg Asp Asn Thr Gln Asn Leu Val Tyr
65                  70                  75                  80

Leu Gln Met Asn Asn Leu Gln Pro His Asp Thr Ala Ile Tyr Tyr Cys
                85                  90                  95

Gly Ala Gln Arg Trp Gly Arg Gly Pro Gly Thr Thr Trp Gly Gln Gly
            100                 105                 110

Thr Gln Val Thr Val Ser Ser
        115

<210> SEQ ID NO 17
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Thr Phe Arg Ile Arg
            20                  25                  30

Val Met Arg Trp Tyr Arg Gln Ala Pro Gly Thr Glu Arg Asp Leu Val
        35                  40                  45

Ala Val Ile Ser Gly Ser Ser Thr Tyr Tyr Ala Asp Ser Val Lys Gly
    50                  55                  60

Arg Phe Thr Ile Ser Arg Asp Asn Ala Lys Asn Thr Leu Tyr Leu Gln
65                  70                  75                  80

Met Asn Asn Leu Lys Pro Glu Asp Thr Ala Val Tyr Tyr Cys Asn Ala
                85                  90                  95

Asp Asp Ser Gly Ile Ala Arg Asp Tyr Trp Gly Gln Gly Thr Gln Val
            100                 105                 110

Thr Val Ser Ser
        115

<210> SEQ ID NO 18
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Val Glu Ser Gly Gly Gly Leu Val Gln Ala Gly Glu
1               5                   10                  15

Ser Arg Arg Leu Ser Cys Ala Val Ser Gly Asp Thr Ser Lys Phe Lys
            20                  25                  30

Ala Val Gly Trp Tyr Arg Gln Ala Pro Gly Ala Gln Arg Glu Leu Leu
        35                  40                  45

Ala Trp Ile Asn Asn Ser Gly Val Gly Asn Thr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Asn Arg Leu Thr Pro Glu Asp Thr Asp Val Tyr Tyr Cys Arg
            85                  90                  95

Phe Tyr Arg Arg Phe Gly Ile Asn Lys Asn Tyr Trp Gly Gln Gly Thr
        100                 105                 110

Gln Val Thr Val Ser Ser
        115

<210> SEQ ID NO 19
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Thr Phe Gly Asn Lys
            20                  25                  30

Pro Met Gly Trp Tyr Arg Gln Ala Pro Gly Lys Gln Arg Glu Leu Val
        35                  40                  45

Ala Val Ile Ser Ser Asp Gly Gly Ser Thr Arg Tyr Ala Ala Leu Val
    50                  55                  60

Lys Gly Arg Phe Thr Ile Ser Arg Asp Asn Ala Lys Asn Thr Val Tyr
65                  70                  75                  80

Leu Gln Met Glu Ser Leu Val Ala Glu Asp Thr Ala Val Tyr Tyr Cys
            85                  90                  95

Asn Ala Leu Arg Thr Tyr Tyr Leu Asn Asp Pro Val Val Phe Ser Trp
        100                 105                 110

Gly Gln Gly Thr Gln Val Thr Val Ser Ser
        115                 120

<210> SEQ ID NO 20
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Thr Ser Ile Asn
            20                  25                  30

Thr Met Tyr Trp Tyr Arg Gln Ala Pro Gly Lys Glu Arg Glu Leu Val
        35                  40                  45

Ala Phe Ile Ser Ser Gly Gly Ser Thr Asn Val Arg Asp Ser Val Lys
    50                  55                  60

Gly Arg Phe Ser Val Ser Arg Asp Ser Ala Lys Asn Ile Val Tyr Leu
65                  70                  75                  80

Gln Met Asn Ser Leu Thr Pro Glu Asp Thr Ala Val Tyr Tyr Cys Asn
            85                  90                  95

Thr Tyr Ile Pro Leu Arg Gly Thr Leu His Asp Tyr Trp Gly Gln Gly
        100                 105                 110

```
Thr Gln Val Thr Val Ser Ser
            115

<210> SEQ ID NO 21
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Val Glu Ser Gly Gly Gly Leu Val Gln Ala Gly Gly
1               5                   10                  15

Ser Leu Arg Leu Ser Cys Val Ala Ser Gly Arg Thr Asp Arg Ile Thr
            20                  25                  30

Thr Met Gly Trp Tyr Arg Gln Ala Pro Gly Lys Gln Arg Glu Leu Val
            35                  40                  45

Ala Thr Ile Ser Asn Arg Gly Thr Ser Asn Tyr Ala Asn Ser Val Lys
        50                  55                  60

Gly Arg Phe Thr Ile Ser Arg Asp Asn Ala Lys Asn Thr Val Tyr Leu
65              70                  75                  80

Gln Met Asn Ser Leu Lys Pro Glu Asp Thr Ala Val Tyr Tyr Cys Asn
                85                  90                  95

Ala Arg Lys Trp Gly Arg Asn Tyr Trp Gly Gln Gly Thr Gln Val Thr
            100                 105                 110

Val Ser Ser
        115

<210> SEQ ID NO 22
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Gln Leu Val Glu Ser Gly Gly Gly Leu Val Gln Ala Arg Gly
1               5                   10                  15

Ser Leu Arg Leu Ser Cys Thr Ala Ser Gly Arg Thr Ile Gly Ile Asn
            20                  25                  30

Asp Met Ala Trp Tyr Arg Gln Ala Pro Gly Asn Gln Arg Glu Leu Val
            35                  40                  45

Ala Thr Ile Thr Lys Gly Gly Thr Asp Tyr Ala Asp Ser Val Asp
        50                  55                  60

Gly Arg Phe Thr Ile Ser Arg Asp Asn Ala Lys Asn Thr Val Tyr Leu
65              70                  75                  80

Gln Met Asn Ser Leu Lys Pro Glu Asp Thr Ala Val Tyr Tyr Cys Asn
                85                  90                  95

Thr Lys Arg Arg Glu Trp Ala Lys Asp Phe Glu Tyr Trp Gly Gln Gly
            100                 105                 110

Thr Gln Val Thr Val Ser Ser
        115

<210> SEQ ID NO 23
<211> LENGTH: 114
<212> TYPE: PRT
<213> ORGANISM: Artificial Sequence
<220> FEATURE:
```

<223> OTHER INFORMATION: Description of Artificial Sequence: Synthetic
    polypeptide

<400> SEQUENCE: 23

Gln Val Gln Leu Val Glu Ser Gly Gly Gly Leu Val Gln Ala Gly Gly
1               5                   10                  15

Ser Leu Arg Leu Ser Cys Ala Ala Ser Ala Ile Gly Ser Ile Asn Ser
            20                  25                  30

Met Ser Trp Tyr Arg Gln Ala Pro Gly Lys Gln Arg Glu Pro Val Ala
        35                  40                  45

Val Ile Thr Asp Arg Gly Ser Thr Ser Tyr Ala Asp Ser Val Lys Gly
    50                  55                  60

Arg Phe Thr Ile Ser Arg Asp Asn Ala Lys Asn Thr Val Tyr Leu Gln
65                  70                  75                  80

Met Asn Ser Leu Lys Pro Glu Asp Thr Ala Ile Tyr Thr Cys His Val
                85                  90                  95

Ile Ala Asp Trp Arg Gly Tyr Trp Gly Gln Gly Thr Gln Val Thr Val
            100                 105                 110

Ser Ser

<210> SEQ ID NO 24
<211> LENGTH: 119
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 24

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Thr Ser Ser Ile Asn
            20                  25                  30

Thr Met Tyr Trp Phe Arg Gln Ala Pro Gly Glu Arg Glu Leu Val
        35                  40                  45

Ala Thr Ile Asn Arg Gly Gly Ser Thr Asn Val Arg Asp Ser Val Lys
    50                  55                  60

Gly Arg Phe Ser Val Ser Arg Asp Ser Ala Lys Asn Ile Val Tyr Leu
65                  70                  75                  80

Gln Met Asn Arg Leu Lys Pro Glu Asp Thr Ala Val Tyr Tyr Cys Asn
                85                  90                  95

Thr Tyr Ile Pro Tyr Gly Gly Thr Leu His Asp Phe Trp Gly Gln Gly
            100                 105                 110

Thr Gln Val Thr Val Ser Ser
        115

<210> SEQ ID NO 25
<211> LENGTH: 114
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 25

Gln Val Gln Leu Val Glu Ser Gly Gly Gly Leu Val Gln Ala Gly Gly
1               5                   10                  15

Ser Leu Arg Leu Ser Cys Thr Thr Ser Thr Thr Phe Ser Ile Asn Ser
            20                  25                  30

```
Met Ser Trp Tyr Arg Gln Ala Pro Gly Asn Gln Arg Glu Pro Val Ala
            35                  40                  45

Val Ile Thr Asn Arg Gly Thr Thr Ser Tyr Ala Asp Ser Val Lys Gly
 50                  55                  60

Arg Phe Thr Ile Ser Arg Asp Asn Ala Arg Asn Thr Val Tyr Leu Gln
 65                  70                  75                  80

Met Asp Ser Leu Lys Pro Glu Asp Thr Ala Ile Tyr Thr Cys His Val
            85                  90                  95

Ile Ala Asp Trp Arg Gly Tyr Trp Gly Gln Gly Thr Gln Val Thr Val
           100                 105                 110

Ser Ser

<210> SEQ ID NO 26
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Val Gln Leu Val Glu Ser Gly Gly Gly Leu Val Gln Ala Gly Gly
 1               5                  10                  15

Ser Leu Thr Leu Ser Cys Ala Ala Ser Gly Ser Thr Phe Ser Ile Arg
            20                  25                  30

Ala Met Arg Trp Tyr Arg Gln Ala Pro Gly Thr Glu Arg Asp Leu Val
            35                  40                  45

Ala Val Ile Tyr Gly Ser Ser Thr Tyr Tyr Ala Asp Ala Val Lys Gly
 50                  55                  60

Arg Phe Thr Ile Ser Arg Asp Asn Ala Lys Asn Thr Leu Tyr Leu Gln
 65                  70                  75                  80

Met Asn Asn Leu Lys Pro Glu Asp Thr Ala Val Tyr Tyr Cys Asn Ala
            85                  90                  95

Asp Thr Ile Gly Thr Ala Arg Asp Tyr Trp Gly Gln Gly Thr Gln Val
           100                 105                 110

Thr Val Ser Ser
           115

<210> SEQ ID NO 27
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Gln Leu Val Glu Ser Gly Gly Gly Leu Val Gln Ala Gly Gly
 1               5                  10                  15

Ser Leu Arg Leu Ser Cys Val Ala Ser Gly Arg Thr Ser Thr Ile Asp
            20                  25                  30

Thr Met Tyr Trp His Arg Gln Ala Pro Gly Asn Glu Arg Glu Leu Val
            35                  40                  45

Ala Tyr Val Thr Ser Arg Gly Thr Ser Asn Val Ala Asp Ser Val Lys
 50                  55                  60

Gly Arg Phe Thr Ile Ser Arg Asp Asn Ala Lys Asn Thr Ala Tyr Leu
 65                  70                  75                  80
```

```
Gln Met Asn Ser Leu Lys Pro Glu Asp Thr Ala Val Tyr Tyr Cys Ser
                85                  90                  95

Val Arg Thr Thr Ser Tyr Pro Val Asp Phe Trp Gly Gln Gly Thr Gln
            100                 105                 110

Val Thr Val Ser Ser
        115

<210> SEQ ID NO 28
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Thr Ser Ser Ile Asn
            20                  25                  30

Thr Met Tyr Trp Tyr Arg Gln Ala Pro Gly Lys Glu Arg Glu Leu Val
        35                  40                  45

Ala Phe Ile Ser Ser Gly Gly Ser Thr Asn Val Arg Asp Ser Val Lys
    50                  55                  60

Gly Arg Phe Ser Val Ser Arg Asp Ser Ala Lys Asn Ile Val Tyr Leu
65                  70                  75                  80

Gln Met Asn Ser Leu Lys Pro Glu Asp Thr Ala Val Tyr Tyr Cys Asn
                85                  90                  95

Thr Tyr Ile Pro Tyr Gly Gly Thr Leu His Asp Phe Trp Gly Gln Gly
            100                 105                 110

Thr Gln Val Thr Val Ser Ser
        115

<210> SEQ ID NO 29
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Val Glu Ser Gly Gly Gly Leu Val Gln Pro Gly Gly
1               5                   10                  15

Ser Leu Arg Leu Ser Cys Ala Ala Ser Gly Gly Asp Trp Ser Ala Asn
            20                  25                  30

Phe Met Tyr Trp Tyr Arg Gln Ala Pro Gly Lys Gln Arg Glu Leu Val
        35                  40                  45

Ala Arg Ile Ser Gly Arg Gly Val Val Asp Tyr Val Glu Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Val Ala Ser Tyr Trp Gly Gln Gly Thr Gln Val Thr Val Ser Ser
            100                 105                 110

<210> SEQ ID NO 30
<211> LENGTH: 111
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Asp Trp Ser Ala Asn
            20                  25                  30

Phe Met Tyr Trp Tyr Arg Gln Ala Pro Gly Lys Gln Arg Glu Leu Val
        35                  40                  45

Ala Arg Ile Ser Gly Arg Gly Val Val Asp Tyr Val Glu Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Val Ala Ser Tyr Trp Gly Gln Gly Thr Leu Val Thr Val Ser Ser
            100                 105                 110

<210> SEQ ID NO 31
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Asp Trp Ser Ala Asn
            20                  25                  30

Phe Met Tyr Trp Val Arg Gln Ala Pro Gly Lys Gly Leu Glu Trp Val
        35                  40                  45

Ser Arg Ile Ser Gly Arg Gly Val Val Asp Tyr Val Glu Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Val Ala Ser Tyr Trp Gly Gln Gly Thr Leu Val Thr Val Ser Ser
            100                 105                 110

<210> SEQ ID NO 32
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Thr Ser Ser Ile Asn
            20                  25                  30

Thr Met Tyr Trp Tyr Arg Gln Ala Pro Gly Lys Glu Arg Glu Leu Val

```
                35                  40                  45
Ala Phe Ile Ser Ser Gly Gly Ser Thr Asn Val Arg Asp Ser Val Lys
        50                  55                  60
Gly Arg Phe Thr Ile Ser Arg Asp Asn Ser Lys Asn Thr Leu Tyr Leu
 65                  70                  75                  80
Gln Met Asn Ser Leu Arg Ala Glu Asp Thr Ala Val Tyr Tyr Cys Asn
                85                  90                  95
Thr Tyr Ile Pro Tyr Gly Gly Leu His Asp Phe Trp Gly Gln Gly
            100                 105                 110
Thr Leu Val Thr Val Ser Ser
        115

<210> SEQ ID NO 33
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Val Gln Leu Val Glu Ser Gly Gly Gly Leu Val Gln Pro Gly Gly
 1               5                  10                  15
Ser Leu Arg Leu Ser Cys Ala Ala Ser Gly Ser Thr Ser Ser Ile Asn
            20                  25                  30
Thr Met Tyr Trp Tyr Arg Gln Ala Pro Gly Lys Glu Arg Glu Leu Val
        35                  40                  45
Ala Phe Ile Ser Ser Gly Gly Ser Thr Asn Val Arg Asp Ser Val Lys
        50                  55                  60
Gly Arg Phe Thr Ile Ser Arg Asp Asn Ser Lys Asn Thr Leu Tyr Leu
 65                  70                  75                  80
Gln Met Asn Ser Leu Arg Ala Glu Asp Thr Ala Val Tyr Tyr Cys Asn
                85                  90                  95
Thr Tyr Ile Pro Tyr Gly Gly Thr Leu His Asp Phe Trp Gly Gln Gly
            100                 105                 110
Thr Leu Val Thr Val Ser Ser
        115

<210> SEQ ID NO 34
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Val Gln Leu Val Glu Ser Gly Gly Gly Leu Val Gln Pro Gly Gly
 1               5                  10                  15
Ser Leu Arg Leu Ser Cys Ala Ala Ser Gly Ser Thr Ser Ser Ile Asn
            20                  25                  30
Thr Met Tyr Trp Val Arg Gln Ala Pro Gly Lys Gly Leu Glu Trp Val
        35                  40                  45
Ser Phe Ile Ser Ser Gly Gly Ser Thr Asn Val Arg Asp Ser Val Lys
        50                  55                  60
Gly Arg Phe Thr Ile Ser Arg Asp Asn Ser Lys Asn Thr Leu Tyr Leu
 65                  70                  75                  80
Gln Met Asn Ser Leu Arg Ala Glu Asp Thr Ala Val Tyr Tyr Cys Asn
```

```
                    85                  90                  95

Thr Tyr Ile Pro Tyr Gly Gly Thr Leu His Asp Phe Trp Gly Gln Gly
                100                 105                 110

Thr Leu Val Thr Val Ser Ser
        115

<210> SEQ ID NO 35
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Val Gln Leu Val Glu Ser Gly Gly Gly Val Val Gln Ala Gly Gly
1               5                   10                  15

Ser Leu Arg Leu Ser Cys Ala Ala Ser Gly Ser Thr Phe Ser Ile Arg
            20                  25                  30

Ala Met Arg Trp Tyr Arg Gln Ala Pro Gly Thr Glu Arg Asp Leu Val
        35                  40                  45

Ala Val Ile Tyr Gly Ser Ser Thr Tyr Tyr Ala Asp Ala Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Asn Ala
                85                  90                  95

Asp Thr Ile Gly Thr Ala Arg Asp Tyr Trp Gly Gln Gly Thr Leu Val
                100                 105                 110

Thr Val Ser Ser
        115

<210> SEQ ID NO 36
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Val Gln Leu Val Glu Ser Gly Gly Gly Val Val Gln Pro Gly Gly
1               5                   10                  15

Ser Leu Arg Leu Ser Cys Ala Ala Ser Gly Ser Thr Phe Ser Ile Arg
            20                  25                  30

Ala Met Arg Trp Tyr Arg Gln Ala Pro Gly Lys Glu Arg Glu Leu Val
        35                  40                  45

Ala Val Ile Tyr Gly Ser Ser Thr Tyr Tyr Ala Asp Ala Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Asn Ala
                85                  90                  95

Asp Thr Ile Gly Thr Ala Arg Asp Tyr Trp Gly Gln Gly Thr Leu Val
                100                 105                 110

Thr Val Ser Ser Gly Gly
        115
```

```
<210> SEQ ID NO 37
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Val Glu Ser Gly Gly Gly Val Val Gln Pro Gly Gly
1               5                   10                  15

Ser Leu Arg Leu Ser Cys Ala Ala Ser Gly Ser Thr Phe Ser Ile Arg
            20                  25                  30

Ala Met Arg Trp Val Arg Gln Ala Pro Gly Lys Gly Leu Glu Trp Val
        35                  40                  45

Ser Val Ile Tyr Gly Ser Ser Thr Tyr Tyr Ala Asp Ala Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Asn Ala
                85                  90                  95

Asp Thr Ile Gly Thr Ala Arg Asp Tyr Trp Gly Gln Gly Thr Leu Val
            100                 105                 110

Thr Val Ser Ser Gly Gly
        115

<210> SEQ ID NO 38
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Val Gln Leu Val Glu Ser Gly Gly Gly Leu Val Gln Ala Gly Gly
1               5                   10                  15

Ser Leu Arg Leu Ser Cys Val Ala Ser Gly Arg Thr Ser Thr Ile Asp
            20                  25                  30

Thr Met Tyr Trp His Arg Gln Ala Pro Gly Asn Glu Arg Glu Leu Val
        35                  40                  45

Ala Tyr Val Thr Ser Arg Gly Thr Ser Asn Val Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ser
                85                  90                  95

Val Arg Thr Thr Ser Tyr Pro Val Asp Phe Trp Gly Gln Gly Thr Leu
            100                 105                 110

Val Thr Val Ser Gly Gly
        115

<210> SEQ ID NO 39
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Ser Thr Ile Asp
            20                  25                  30

Thr Met Tyr Trp His Arg Gln Ala Pro Gly Lys Glu Arg Glu Leu Val
        35                  40                  45

Ala Tyr Val Thr Ser Arg Gly Thr Ser Asn Val Ala Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ser
            85                  90                  95

Val Arg Thr Thr Ser Tyr Pro Val Asp Phe Trp Gly Gln Gly Thr Leu
            100                 105                 110

Val Thr Val Ser Ser
        115

<210> SEQ ID NO 40
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Ser Thr Ile Asp
            20                  25                  30

Thr Met Tyr Trp Val Arg Gln Ala Pro Gly Lys Gly Leu Glu Trp Val
        35                  40                  45

Ser Tyr Val Thr Ser Arg Gly Thr Ser Asn Val Ala Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ser
            85                  90                  95

Val Arg Thr Thr Ser Tyr Pro Val Asp Phe Trp Gly Gln Gly Thr Leu
            100                 105                 110

Val Thr Val Ser Ser
        115

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Glu Ser Gly Gly Gly Leu Val
1               5

<210> SEQ ID NO 42
<211> LENGTH: 3
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 42

Leu Ser Cys
1

<210> SEQ ID NO 43
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Arg Phe
1

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Val Thr Val Ser Ser
1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gln Leu Val Glu Ser Gly Gly Gly
1               5

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Gly Ser Leu Arg Leu Ser Cys Ala Ala Ser Gly
1               5                   10

<210> SEQ ID NO 47
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ala Ser Gly
1
```

```
<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Arg Gln Ala Pro Gly
1               5

<210> SEQ ID NO 49
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Val Lys Gly Arg Phe Thr Ile Ser Arg Asp Asn Ser Lys Asn Thr Leu
1               5                   10                  15

Tyr Leu Gln Met Asn Ser Leu Arg Ala Glu Asp Thr Ala Val Tyr Tyr
            20                  25                  30

Cys

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Trp Gly Gln Gly Thr Leu Val Thr Val Ser Ser
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Arg Thr Phe Ser Val Arg Gly Met Ala
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ile Asn Ser Ser Gly Ser Thr Asn Tyr Gly
1               5                   10

<210> SEQ ID NO 53
<211> LENGTH: 10
<212> TYPE: PRT
```

-continued

```
<213> ORGANISM: Artificial Sequence
<220> FEATURE:
<223> OTHER INFORMATION: Description of Artificial Sequence: Synthetic
      peptide

<400> SEQUENCE: 53

Asn Ala Gly Gly Gly Pro Leu Gly Ser Arg
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Gly Asp Trp Ser Ala Asn Phe Met Tyr
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ile Ser Ser Gly Gly Ser Thr Asn Val Arg
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asn Ala Asp Thr Ile Gly Thr Ala Arg Asp
1               5                   10

<210> SEQ ID NO 57
<211> LENGTH: 630
<212> TYPE: PRT
<213> ORGANISM: Homo sapiens

<400> SEQUENCE: 57

Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
                20                  25                  30

Pro Ser Arg Thr Leu Ala Gly Glu Thr Gly Gln Glu Ala Ala Pro Leu
            35                  40                  45

Asp Gly Val Leu Ala Asn Pro Pro Asn Ile Ser Ser Leu Ser Pro Arg
        50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
```

```
            100                 105                 110
Glu Asp Leu Asp Ala Leu Pro Leu Asp Leu Leu Phe Leu Asn Pro
            115                 120                 125

Asp Ala Phe Ser Gly Pro Gln Ala Cys Thr Arg Phe Phe Ser Arg Ile
        130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
                180                 185                 190

Pro Gly Arg Phe Val Ala Glu Ser Ala Glu Val Leu Leu Pro Arg Leu
            195                 200                 205

Val Ser Cys Pro Gly Pro Leu Asp Gln Asp Gln Gln Glu Ala Ala Arg
    210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
                260                 265                 270

Gln Arg Ser Ser Arg Asp Pro Ser Trp Arg Gln Pro Glu Arg Thr Ile
            275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Ala Pro Arg Arg Pro Leu
                405                 410                 415

Pro Gln Val Ala Thr Leu Ile Asp Arg Phe Val Lys Gly Arg Gly Gln
            420                 425                 430

Leu Asp Lys Asp Thr Leu Asp Thr Leu Thr Ala Phe Tyr Pro Gly Tyr
        435                 440                 445

Leu Cys Ser Leu Ser Pro Glu Glu Leu Ser Ser Val Pro Pro Ser Ser
    450                 455                 460

Ile Trp Ala Val Arg Pro Gln Asp Leu Asp Thr Cys Asp Pro Arg Gln
465                 470                 475                 480

Leu Asp Val Leu Tyr Pro Lys Ala Arg Leu Ala Phe Gln Asn Met Asn
                485                 490                 495

Gly Ser Glu Tyr Phe Val Lys Ile Gln Ser Phe Leu Gly Gly Ala Pro
            500                 505                 510

Thr Glu Asp Leu Lys Ala Leu Ser Gln Gln Asn Val Ser Met Asp Leu
        515                 520                 525
```

```
Ala Thr Phe Met Lys Leu Arg Thr Asp Ala Val Leu Pro Leu Thr Val
            530                 535                 540

Ala Glu Val Gln Lys Leu Leu Gly Pro His Val Glu Gly Leu Lys Ala
545                 550                 555                 560

Glu Glu Arg His Arg Pro Val Arg Asp Trp Ile Leu Arg Gln Arg Gln
                565                 570                 575

Asp Asp Leu Asp Thr Leu Gly Leu Gly Leu Gln Gly Gly Ile Pro Asn
            580                 585                 590

Gly Tyr Leu Val Leu Asp Leu Ser Met Gln Glu Ala Leu Ser Gly Thr
                595                 600                 605

Pro Cys Leu Leu Gly Pro Gly Pro Val Leu Thr Val Leu Ala Leu Leu
            610                 615                 620

Leu Ala Ser Thr Leu Ala
625                 630

<210> SEQ ID NO 58
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gln Val Gln Leu Val Glu Ser Gly Gly Gly Val Val Gln Ala Gly Gly
1               5                   10                  15

Ser Leu Thr Leu Ser Cys Ala Ala Ser Gly Ser Thr Phe Ser Ile Arg
            20                  25                  30

Ala Met Arg Trp Tyr Arg Gln Ala Pro Gly Thr Glu Arg Asp Leu Val
        35                  40                  45

Ala Val Ile Tyr Gly Ser Ser Thr Tyr Tyr Ala Asp Ala Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Asn Ala
                85                  90                  95

Asp Thr Ile Gly Thr Ala Arg Asp Tyr Trp Gly Gln Gly Thr Leu Val
            100                 105                 110

Thr Val Ser Ser
        115

<210> SEQ ID NO 59
<211> LENGTH: 503
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gln Val Gln Leu Val Glu Ser Gly Gly Ala Leu Val Gln Pro Gly Gly
1               5                   10                  15

Ser Leu Arg Leu Ser Cys Ala Ala Ser Gly Phe Pro Val Asn Arg Tyr
            20                  25                  30

Ser Met Arg Trp Tyr Arg Gln Ala Pro Gly Lys Glu Arg Glu Trp Val
        35                  40                  45

Ala Gly Met Ser Ser Ala Gly Asp Arg Ser Ser Tyr Glu Asp Ser Val
    50                  55                  60
```

```
Lys Gly Arg Phe Thr Ile Ser Arg Asp Asp Ala Arg Asn Thr Val Tyr
 65                  70                  75                  80

Leu Gln Met Asn Ser Leu Lys Pro Glu Asp Thr Ala Val Tyr Tyr Cys
                     85                  90                  95

Asn Val Asn Val Gly Phe Glu Tyr Trp Gly Gln Gly Thr Gln Val Thr
                100                 105                 110

Val Ser Ser Gly Gly Gly Gly Ser Gly Gly Gly Ser Glu Val Gln Leu
            115                 120                 125

Val Glu Ser Gly Gly Gly Leu Val Gln Pro Gly Asn Ser Leu Arg Leu
130                 135                 140

Ser Cys Ala Ala Ser Gly Phe Thr Phe Ser Lys Phe Gly Met Ser Trp
145                 150                 155                 160

Val Arg Gln Ala Pro Gly Lys Gly Leu Glu Trp Val Ser Ser Ile Ser
                165                 170                 175

Gly Ser Gly Arg Asp Thr Leu Tyr Ala Asp Ser Val Lys Gly Arg Phe
                180                 185                 190

Thr Ile Ser Arg Asp Asn Ala Lys Thr Thr Leu Tyr Leu Gln Met Asn
                195                 200                 205

Ser Leu Arg Pro Glu Asp Thr Ala Val Tyr Tyr Cys Thr Ile Gly Gly
    210                 215                 220

Ser Leu Ser Val Ser Ser Gln Gly Thr Leu Val Thr Val Ser Ser Gly
225                 230                 235                 240

Gly Gly Gly Ser Gly Gly Ser Glu Val Gln Leu Val Glu Ser Gly
                245                 250                 255

Gly Gly Leu Val Gln Pro Gly Gly Ser Leu Lys Leu Ser Cys Ala Ala
            260                 265                 270

Ser Gly Phe Thr Phe Asn Lys Tyr Ala Ile Asn Trp Val Arg Gln Ala
    275                 280                 285

Pro Gly Lys Gly Leu Glu Trp Val Ala Arg Ile Arg Ser Lys Tyr Asn
    290                 295                 300

Asn Tyr Ala Thr Tyr Tyr Ala Asp Gln Val Lys Asp Arg Phe Thr Ile
305                 310                 315                 320

Ser Arg Asp Asp Ser Lys Asn Thr Ala Tyr Leu Gln Met Asn Asn Leu
                325                 330                 335

Lys Thr Glu Asp Thr Ala Val Tyr Tyr Cys Val Arg His Ala Asn Phe
                340                 345                 350

Gly Asn Ser Tyr Ile Ser Tyr Trp Ala Tyr Trp Gly Gln Gly Thr Leu
                355                 360                 365

Val Thr Val Ser Ser Gly Gly Gly Ser Gly Gly Gly Ser Gly
                370                 375                 380

Gly Gly Ser Gln Thr Val Val Thr Gln Glu Pro Ser Leu Thr Val
385                 390                 395                 400

Ser Pro Gly Gly Thr Val Thr Leu Thr Cys Ala Ser Ser Thr Gly Ala
                405                 410                 415

Val Thr Ser Gly Asn Tyr Pro Asn Trp Val Gln Gln Lys Pro Gly Gln
                420                 425                 430

Ala Pro Arg Gly Leu Ile Gly Gly Thr Lys Phe Leu Val Pro Gly Thr
                435                 440                 445

Pro Ala Arg Phe Ser Gly Ser Leu Leu Gly Gly Lys Ala Ala Leu Thr
    450                 455                 460

Leu Ser Gly Val Gln Pro Glu Asp Glu Ala Glu Tyr Tyr Cys Thr Leu
465                 470                 475                 480
```

Trp Tyr Ser Asn Arg Trp Val Phe Gly Gly Gly Thr Lys Leu Thr Val
            485                 490                 495

Leu His His His His His His
        500

<210> SEQ ID NO 60
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gln Val Gln Leu Val Glu Ser Gly Gly Gly Val Val Gln Ala Gly Gly
1               5                   10                  15

Ser Leu Arg Leu Ser Cys Ala Ala Ser Gly Ser Thr Phe Ser Ile Arg
            20                  25                  30

Ala Met Arg Trp Tyr Arg Gln Ala Pro Gly Thr Glu Arg Asp Leu Val
        35                  40                  45

Ala Val Ile Tyr Gly Ser Ser Thr Tyr Tyr Ala Asp Ala Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Asn Ala
                85                  90                  95

Asp Thr Ile Gly Thr Ala Arg Asp Tyr Trp Gly Gln Gly Thr Leu Val
            100                 105                 110

Thr Val Ser Ser
        115

<210> SEQ ID NO 61
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Gln Leu Val Glu Ser Gly Gly Gly Val Val Gln Pro Gly Gly
1               5                   10                  15

Ser Leu Arg Leu Ser Cys Ala Ala Ser Gly Ser Thr Phe Ser Ile Arg
            20                  25                  30

Ala Met Arg Trp Tyr Arg Gln Ala Pro Gly Lys Glu Arg Glu Leu Val
        35                  40                  45

Ala Val Ile Tyr Gly Ser Ser Thr Tyr Tyr Ala Asp Ala Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Asn Ala
                85                  90                  95

Asp Thr Ile Gly Thr Ala Arg Asp Tyr Trp Gly Gln Gly Thr Leu Val
            100                 105                 110

Thr Val Ser Ser
        115

<210> SEQ ID NO 62
<211> LENGTH: 116

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Val Gln Leu Val Glu Ser Gly Gly Gly Val Val Gln Pro Gly Gly
1               5                   10                  15

Ser Leu Arg Leu Ser Cys Ala Ala Ser Gly Ser Thr Phe Ser Ile Arg
            20                  25                  30

Ala Met Arg Trp Val Arg Gln Ala Pro Gly Lys Gly Leu Glu Trp Val
        35                  40                  45

Ser Val Ile Tyr Gly Ser Ser Thr Tyr Tyr Ala Asp Ala Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Asn Ala
                85                  90                  95

Asp Thr Ile Gly Thr Ala Arg Asp Tyr Trp Gly Gln Gly Thr Leu Val
            100                 105                 110

Thr Val Ser Ser
        115

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Arg Thr Phe Ser Val Arg Gly Met Ala
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Ser Ile Pro Ser Ile Glu Gln Met Gly
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gly Thr Thr Tyr Thr Phe Asp Leu Met Ser
1               5                   10

<210> SEQ ID NO 66
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 66

Gly Ser Thr Ser Asn Ile Asn Asn Met Arg
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Ser Thr Phe Gly Ile Asn Ala Met Gly
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ile Ser Ala Phe Arg Leu Met Ser Val Arg
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Arg Pro Phe Ser Ile Asn Thr Met Gly
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Ser Asp Phe Thr Glu Asp Ala Met Ala
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Ser Asp Phe Thr Glu Asp Ala Met Ala
1               5                   10
```

<210> SEQ ID NO 72
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Phe Thr Phe Ser Ser Phe Gly Met Ser
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Leu Thr Tyr Ser Ile Val Ala Val Gly
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Leu Thr Phe Gly Val Tyr Gly Met Glu
1               5                   10

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Thr Thr Ser Ser Ile Asn Ser Met Ser
1               5

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Arg Thr Leu Ser Arg Tyr Ala Met Gly
1               5                   10

<210> SEQ ID NO 77
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 77

Gly Ser Ile Phe Ser Pro Asn Ala Met Ile
1               5                   10

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Ala Thr Ser Ala Ile Thr Asn Leu Gly
1               5                   10

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Ser Thr Phe Arg Ile Arg Val Met Arg
1               5                   10

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Asp Thr Ser Lys Phe Lys Ala Val Gly
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Ser Thr Phe Gly Asn Lys Pro Met Gly
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gly Ser Thr Ser Ser Ile Asn Thr Met Tyr
1               5                   10

<210> SEQ ID NO 83
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 83

Gly Arg Thr Asp Arg Ile Thr Thr Met Gly
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Arg Thr Ile Gly Ile Asn Asp Met Ala
1               5                   10

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ala Ile Gly Ser Ile Asn Ser Met Ser
1               5

<210> SEQ ID NO 86
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gly Ser Thr Ser Ser Ile Asn Thr Met Tyr
1               5                   10

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Thr Thr Phe Ser Ile Asn Ser Met Ser
1               5

<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gly Ser Thr Phe Ser Ile Arg Ala Met Arg
1               5                   10
```

<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gly Arg Thr Ser Thr Ile Asp Thr Met Tyr
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gly Ser Thr Ser Ser Ile Asn Thr Met Tyr
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gly Gly Asp Trp Ser Ala Asn Phe Met Tyr
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Gly Asp Trp Ser Ala Asn Phe Met Tyr
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Ser Thr Ser Ser Ile Asn Thr Met Tyr
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 94

Gly Ser Thr Ser Ser Ile Asn Thr Met Tyr
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Ser Thr Ser Ser Ile Asn Thr Met Tyr
1               5                   10

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gly Ser Thr Phe Ser Ile Arg Ala Met Arg
1               5                   10

<210> SEQ ID NO 97
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Ser Thr Phe Ser Ile Arg Ala Met Arg
1               5                   10

<210> SEQ ID NO 98
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Ser Thr Phe Ser Ile Arg Ala Met Arg
1               5                   10

<210> SEQ ID NO 99
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Arg Thr Ser Thr Ile Asp Thr Met Tyr
1               5                   10

<210> SEQ ID NO 100
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gly Arg Thr Ser Thr Ile Asp Thr Met Tyr
1               5                   10

<210> SEQ ID NO 101
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Arg Thr Ser Thr Ile Asp Thr Met Tyr
1               5                   10

<210> SEQ ID NO 102
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Thr Met Asn Pro Asp Gly Phe Pro Asn Tyr Ala Asp Ala Val Lys Gly
1               5                   10                  15

Arg Phe Thr

<210> SEQ ID NO 103
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ala Leu Thr Ser Gly Gly Arg Ala Asn Tyr Ala Asp Ser Val Lys Gly
1               5                   10                  15

Arg Phe Thr

<210> SEQ ID NO 104
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ser Ile Ser Ser Asp Gly Arg Thr Ser Tyr Ala Asp Ser Val Arg Gly
1               5                   10                  15

Arg Phe Thr

<210> SEQ ID NO 105
<211> LENGTH: 19
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 105

Val Ile Thr Arg Gly Gly Tyr Ala Ile Tyr Leu Asp Ala Val Lys Gly
1               5                   10                  15

Arg Phe Thr

<210> SEQ ID NO 106
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Val Ile Ser Arg Gly Gly Ser Thr Asn Tyr Ala Asp Ser Val Lys Gly
1               5                   10                  15

Arg Phe Thr

<210> SEQ ID NO 107
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Thr Ile Asp Gln Leu Gly Arg Thr Asn Tyr Ala Asp Ser Val Lys Gly
1               5                   10                  15

Arg Phe Ala

<210> SEQ ID NO 108
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ser Ile Ser Ser Ser Gly Asp Phe Thr Tyr Thr Asp Ser Val Lys Gly
1               5                   10                  15

Arg Phe Thr

<210> SEQ ID NO 109
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Phe Val Ser Lys Asp Gly Lys Arg Ile Leu Tyr Leu Asp Ser Val Arg
1               5                   10                  15

Gly Arg Phe Thr
            20

<210> SEQ ID NO 110
<211> LENGTH: 20
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 110

Phe Val Ser Lys Asp Gly Lys Arg Ile Leu Tyr Leu Asp Ser Val Arg
1               5                   10                  15

Gly Arg Phe Thr
            20

<210> SEQ ID NO 111
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Ser Ile Ser Gly Ser Gly Ser Asp Thr Leu Tyr Ala Asp Ser Val Lys
1               5                   10                  15

Gly Arg Phe Thr
            20

<210> SEQ ID NO 112
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Asp Ile Ser Pro Val Gly Asn Thr Asn Tyr Ala Asp Ser Val Lys Gly
1               5                   10                  15

Arg Phe Thr

<210> SEQ ID NO 113
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Ser His Thr Ser Thr Gly Tyr Val Tyr Tyr Arg Asp Ser Val Lys Gly
1               5                   10                  15

Arg Phe Thr

<210> SEQ ID NO 114
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Val Ile Thr Asp Arg Gly Ser Thr Ser Tyr Ala Asp Ser Val Lys Gly
1               5                   10                  15

Arg Phe Thr

```
<210> SEQ ID NO 115
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Ala Ile Ser Arg Ser Gly Gly Thr Thr Arg Tyr Ser Asp Ser Val Lys
1               5                   10                  15

Gly Arg Phe Thr
            20

<210> SEQ ID NO 116
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ser Ile Asn Ser Ser Gly Ser Thr Asn Tyr Gly Asp Ser Val Lys Gly
1               5                   10                  15

Arg Phe Thr

<210> SEQ ID NO 117
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Arg Ile Ser Val Arg Glu Asp Lys Glu Asp Tyr Glu Asp Ser Val Lys
1               5                   10                  15

Gly Arg Phe Thr
            20

<210> SEQ ID NO 118
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Val Ile Ser Gly Ser Ser Thr Tyr Tyr Ala Asp Ser Val Lys Gly Arg
1               5                   10                  15

Phe Thr

<210> SEQ ID NO 119
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Trp Ile Asn Asn Ser Gly Val Gly Asn Thr Ala Glu Ser Val Lys Gly
1               5                   10                  15
```

Arg Phe Thr

<210> SEQ ID NO 120
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Val Ile Ser Ser Asp Gly Gly Ser Thr Arg Tyr Ala Ala Leu Val Lys
1               5                   10                  15

Gly Arg Phe Thr
            20

<210> SEQ ID NO 121
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Phe Ile Ser Ser Gly Gly Ser Thr Asn Val Arg Asp Ser Val Lys Gly
1               5                   10                  15

Arg Phe Ser

<210> SEQ ID NO 122
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Thr Ile Ser Asn Arg Gly Thr Ser Asn Tyr Ala Asn Ser Val Lys Gly
1               5                   10                  15

Arg Phe Thr

<210> SEQ ID NO 123
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Thr Ile Thr Lys Gly Gly Thr Thr Asp Tyr Ala Asp Ser Val Asp Gly
1               5                   10                  15

Arg Phe Thr

<210> SEQ ID NO 124
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Val Ile Thr Asp Arg Gly Ser Thr Ser Tyr Ala Asp Ser Val Lys Gly

```
                1               5                  10                  15

Arg Phe Thr

<210> SEQ ID NO 125
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Thr Ile Asn Arg Gly Gly Ser Thr Asn Val Arg Asp Ser Val Lys Gly
1               5                  10                  15

Arg Phe Ser

<210> SEQ ID NO 126
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Val Ile Thr Asn Arg Gly Thr Thr Ser Tyr Ala Asp Ser Val Lys Gly
1               5                  10                  15

Arg Phe Thr

<210> SEQ ID NO 127
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Val Ile Tyr Gly Ser Ser Thr Tyr Tyr Ala Asp Ala Val Lys Gly Arg
1               5                  10                  15

Phe Thr

<210> SEQ ID NO 128
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Tyr Val Thr Ser Arg Gly Thr Ser Asn Val Ala Asp Ser Val Lys Gly
1               5                  10                  15

Arg Phe Thr

<210> SEQ ID NO 129
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129
```

Phe Ile Ser Ser Gly Gly Ser Thr Asn Val Arg Asp Ser Val Lys Gly
1               5                   10                  15

Arg Phe Ser

<210> SEQ ID NO 130
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Arg Ile Ser Gly Arg Gly Val Val Asp Tyr Val Glu Ser Val Lys Gly
1               5                   10                  15

Arg Phe Thr

<210> SEQ ID NO 131
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Arg Ile Ser Gly Arg Gly Val Val Asp Tyr Val Glu Ser Val Lys Gly
1               5                   10                  15

Arg Phe Thr

<210> SEQ ID NO 132
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Phe Ile Ser Ser Gly Gly Ser Thr Asn Val Arg Asp Ser Val Lys Gly
1               5                   10                  15

Arg Phe Thr

<210> SEQ ID NO 133
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Phe Ile Ser Ser Gly Gly Ser Thr Asn Val Arg Asp Ser Val Lys Gly
1               5                   10                  15

Arg Phe Thr

<210> SEQ ID NO 134
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

```
Phe Ile Ser Ser Gly Gly Ser Thr Asn Val Arg Asp Ser Val Lys Gly
1               5                   10                  15

Arg Phe Thr

<210> SEQ ID NO 135
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Val Ile Tyr Gly Ser Ser Thr Tyr Tyr Ala Asp Ala Val Lys Gly Arg
1               5                   10                  15

Phe Thr

<210> SEQ ID NO 136
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Val Ile Tyr Gly Ser Ser Thr Tyr Tyr Ala Asp Ala Val Lys Gly Arg
1               5                   10                  15

Phe Thr

<210> SEQ ID NO 137
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Val Ile Tyr Gly Ser Ser Thr Tyr Tyr Ala Asp Ala Val Lys Gly Arg
1               5                   10                  15

Phe Thr

<210> SEQ ID NO 138
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Tyr Val Thr Ser Arg Gly Thr Ser Asn Val Ala Asp Ser Val Lys Gly
1               5                   10                  15

Arg Phe Thr

<210> SEQ ID NO 139
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 139

Tyr Val Thr Ser Arg Gly Thr Ser Asn Val Ala Asp Ser Val Lys Gly
1               5                   10                  15

Arg Phe Thr

<210> SEQ ID NO 140
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Tyr Val Thr Ser Arg Gly Thr Ser Asn Val Ala Asp Ser Val Lys Gly
1               5                   10                  15

Arg Phe Thr

<210> SEQ ID NO 141
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gly Pro Tyr
1

<210> SEQ ID NO 142
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Gly Arg Phe Lys Gly Asp Tyr Ala Gln Arg Ser Gly Met Asp Tyr
1               5                   10                  15

<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gln Arg Ser Gly Val Arg Ala Phe
1               5

<210> SEQ ID NO 144
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Asp Arg Val Glu Gly Thr Ser Gly Gly Pro Gln Leu Arg Asp Tyr
1               5                   10                  15
```

<210> SEQ ID NO 145
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 145

Arg Thr Tyr Thr Arg His Asp Tyr
1               5

<210> SEQ ID NO 146
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 146

Gly Gly Gly Pro Leu Gly Ser Arg Trp Leu Arg Gly Arg His
1               5                   10

<210> SEQ ID NO 147
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 147

Arg Arg Thr Tyr Leu Pro Arg Arg Phe Gly Ser
1               5                   10

<210> SEQ ID NO 148
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 148

Ala Pro Gly Ala Ala Arg Asn Tyr
1               5

<210> SEQ ID NO 149
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 149

Ala Pro Gly Ala Ala Arg Asn Val
1               5

<210> SEQ ID NO 150
<211> LENGTH: 8
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 150

Gly Gly Ser Leu Ser Arg Ser Ser
1               5

<210> SEQ ID NO 151
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Val Arg Gly Trp Leu Asp Glu Arg Pro Gly Pro Gly Pro Ile Val Tyr
1               5                   10                  15

<210> SEQ ID NO 152
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Asn Arg Gly Ser Tyr Glu Tyr
1               5

<210> SEQ ID NO 153
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Ile Ala Asp Trp Arg Gly Tyr
1               5

<210> SEQ ID NO 154
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Arg Arg Arg Gly Trp Gly Arg Thr Leu Glu Tyr
1               5                   10

<210> SEQ ID NO 155
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Ser Asp Phe Arg Arg Gly Thr Gln Tyr
1               5

<210> SEQ ID NO 156
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 156

Gln Arg Trp Gly Arg Gly Pro Gly Thr Thr
1               5                   10

<210> SEQ ID NO 157
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Asp Asp Ser Gly Ile Ala Arg Asp Tyr
1               5

<210> SEQ ID NO 158
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Tyr Arg Arg Phe Gly Ile Asn Lys Asn Tyr
1               5                   10

<210> SEQ ID NO 159
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Leu Arg Thr Tyr Tyr Leu Asn Asp Pro Val Val Phe Ser
1               5                   10

<210> SEQ ID NO 160
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Tyr Ile Pro Leu Arg Gly Thr Leu His Asp Tyr
1               5                   10

<210> SEQ ID NO 161
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Arg Lys Trp Gly Arg Asn Tyr
1               5
```

<210> SEQ ID NO 162
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Lys Arg Arg Glu Trp Ala Lys Asp Phe Glu Tyr
1               5                   10

<210> SEQ ID NO 163
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Ile Ala Asp Trp Arg Gly Tyr
1               5

<210> SEQ ID NO 164
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Tyr Ile Pro Tyr Gly Gly Thr Leu His Asp Phe
1               5                   10

<210> SEQ ID NO 165
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Ile Ala Asp Trp Arg Gly Tyr
1               5

<210> SEQ ID NO 166
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Asp Thr Ile Gly Thr Ala Arg Asp Tyr
1               5

<210> SEQ ID NO 167
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Arg Thr Thr Ser Tyr Pro Val Asp Phe
1               5

<210> SEQ ID NO 168
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Tyr Ile Pro Tyr Gly Gly Thr Leu His Asp Phe
1               5                   10

<210> SEQ ID NO 169
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Ala Ser Tyr
1

<210> SEQ ID NO 170
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Ala Ser Tyr
1

<210> SEQ ID NO 171
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Tyr Ile Pro Tyr Gly Gly Thr Leu His Asp Phe
1               5                   10

<210> SEQ ID NO 172
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Tyr Ile Pro Tyr Gly Gly Thr Leu His Asp Phe
1               5                   10

<210> SEQ ID NO 173
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Tyr Ile Pro Tyr Gly Gly Thr Leu His Asp Phe
1               5                   10

<210> SEQ ID NO 174
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Asp Thr Ile Gly Thr Ala Arg Asp Tyr
1               5

<210> SEQ ID NO 175
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Asp Thr Ile Gly Thr Ala Arg Asp Tyr
1               5

<210> SEQ ID NO 176
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Asp Thr Ile Gly Thr Ala Arg Asp Tyr
1               5

<210> SEQ ID NO 177
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Arg Thr Thr Ser Tyr Pro Val Asp Phe
1               5

<210> SEQ ID NO 178
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Arg Thr Thr Ser Tyr Pro Val Asp Phe
```

```
1               5

<210> SEQ ID NO 179
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Arg Thr Thr Ser Tyr Pro Val Asp Phe
1               5

<210> SEQ ID NO 180
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Gln Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 181
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Gln Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 182
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Gln Val Gln Leu Val Glu Ser Gly Gly Gly Leu Val Gln Ala Gly Gly
1               5                   10                  15

Ser Leu Arg Leu Ser Cys Ala Phe Ser
            20                  25

<210> SEQ ID NO 183
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Gln Val Gln Leu Val Glu Ser Gly Gly Gly Leu Val Gln Ala Gly Gly
```

```
1               5                   10                  15

Ser Leu Arg Leu Ser Cys Val Ala Ser
            20                  25

<210> SEQ ID NO 184
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Gln Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 185
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Gln Val Arg Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 186
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Gln Val Arg Leu Val Glu Ser Gly Gly Gly Leu Val Gln Ala Gly Glu
1               5                   10                  15

Ser Leu Arg Leu Ser Cys Ala Ala Ser
            20                  25

<210> SEQ ID NO 187
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Gln Val Gln Pro Val Glu Ser Gly Gly Gly Leu Val Gln Pro Gly Gly
1               5                   10                  15

Ser Leu Arg Leu Ser Cys Val Val Ser
            20                  25

<210> SEQ ID NO 188
<211> LENGTH: 25
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 188

Gln Val Gln Pro Val Glu Ser Gly Gly Gly Leu Val Gln Pro Gly Gly
1               5                   10                  15

Ser Leu Arg Leu Ser Cys Val Val Ser
            20                  25

<210> SEQ ID NO 189
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Glu Val Gln Leu Val Glu Ser Gly Gly Gly Leu Val Gln Pro Gly Asn
1               5                   10                  15

Ser Leu Arg Leu Ser Cys Ala Ala Ser
            20                  25

<210> SEQ ID NO 190
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Gln Val Gln Ile Val Glu Ser Gly Gly Gly Leu Val Gln Ala Gly Gly
1               5                   10                  15

Ser Leu Arg Leu Ser Cys Val Ala Ser
            20                  25

<210> SEQ ID NO 191
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Gln Val Gln Leu Val Glu Ser Gly Gly Gly Leu Val Gln Thr Gly Gly
1               5                   10                  15

Ser Leu Arg Leu Ser Cys Ala Ala Ser
            20                  25

<210> SEQ ID NO 192
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Gln Val Gln Leu Val Glu Ser Gly Gly Gly Leu Val Gln Ala Gly Gly
1               5                   10                  15

Ser Leu Arg Leu Ser Cys Ala Ala Ser
            20                  25
```

<210> SEQ ID NO 193
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Gln Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 194
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Gln Val Gln Leu Gly Glu Ser Gly Gly Gly Leu Val Gln Ala Gly Gly
1               5                   10                  15

Ser Leu Arg Leu Ser Cys Ala Ala Ser
            20                  25

<210> SEQ ID NO 195
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Gln Val Gln Leu Val Glu Ser Gly Gly Gly Leu Val Pro Ser Gly Gly
1               5                   10                  15

Ser Leu Arg Leu Ser Cys Ala Ala Ser
            20                  25

<210> SEQ ID NO 196
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Gln Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 197
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

```
Gln Val Gln Leu Val Glu Ser Gly Gly Gly Leu Val Gln Ala Gly Glu
1               5                   10                  15

Ser Arg Arg Leu Ser Cys Ala Val Ser
            20                  25

<210> SEQ ID NO 198
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Gln Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 199
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Gln Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 200
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Gln Val Gln Leu Val Glu Ser Gly Gly Gly Leu Val Gln Ala Gly Gly
1               5                   10                  15

Ser Leu Arg Leu Ser Cys Val Ala Ser
            20                  25

<210> SEQ ID NO 201
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Gln Val Gln Leu Val Glu Ser Gly Gly Gly Leu Val Gln Ala Arg Gly
1               5                   10                  15

Ser Leu Arg Leu Ser Cys Thr Ala Ser
            20                  25

<210> SEQ ID NO 202
<211> LENGTH: 25
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 202

Gln Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 203
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Gln Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 204
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Gln Val Gln Leu Val Glu Ser Gly Gly Gly Leu Val Gln Ala Gly Gly
1               5                   10                  15

Ser Leu Arg Leu Ser Cys Thr Thr Ser
            20                  25

<210> SEQ ID NO 205
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Gln Val Gln Leu Val Glu Ser Gly Gly Gly Leu Val Gln Ala Gly Gly
1               5                   10                  15

Ser Leu Thr Leu Ser Cys Ala Ala Ser
            20                  25

<210> SEQ ID NO 206
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Gln Val Gln Leu Val Glu Ser Gly Gly Gly Leu Val Gln Ala Gly Gly
1               5                   10                  15

Ser Leu Arg Leu Ser Cys Val Ala Ser
            20                  25
```

<210> SEQ ID NO 207
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Gln Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 208
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 209
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 210
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Glu Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 211
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 212
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 213
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Gln Val Gln Leu Val Glu Ser Gly Gly Gly Val Val Gln Ala Gly Gly
1               5                   10                  15

Ser Leu Arg Leu Ser Cys Ala Ala Ser
            20                  25

<210> SEQ ID NO 214
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Gln Val Gln Leu Val Glu Ser Gly Gly Gly Val Val Gln Pro Gly Gly
1               5                   10                  15

Ser Leu Arg Leu Ser Cys Ala Ala Ser
            20                  25

<210> SEQ ID NO 215
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Gln Val Gln Leu Val Glu Ser Gly Gly Gly Val Val Gln Pro Gly Gly
1               5                   10                  15

Ser Leu Arg Leu Ser Cys Ala Ala Ser
            20                  25

<210> SEQ ID NO 216
<211> LENGTH: 25
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 216

Glu Val Gln Leu Val Glu Ser Gly Gly Gly Leu Val Gln Ala Gly Gly
1               5                   10                  15

Ser Leu Arg Leu Ser Cys Val Ala Ser
            20                  25

<210> SEQ ID NO 217
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 218
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 219
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Trp Tyr Arg Gln Ala Gly Asn Asn Arg Ala Leu Val Ala
1               5                   10

<210> SEQ ID NO 220
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Trp Tyr Arg Gln Ala Pro Gly Lys Gln Arg Glu Leu Val Ala
1               5                   10

<210> SEQ ID NO 221
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 221

Trp Tyr Arg Gln Ala Pro Gly Lys Gln Arg Thr Val Val Ala
1               5                   10

<210> SEQ ID NO 222
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Trp Tyr Arg Gln Ala Pro Gly Lys Glu Arg Glu Leu Val Ala
1               5                   10

<210> SEQ ID NO 223
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Trp Tyr Arg Gln Ala Pro Gly Lys Gln Arg Glu Leu Val Ala
1               5                   10

<210> SEQ ID NO 224
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Trp Tyr Arg Gln Asp Pro Ser Lys Gln Arg Glu Trp Val Ala
1               5                   10

<210> SEQ ID NO 225
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Trp Tyr Arg Gln Ala Pro Gly Lys Gln Arg Glu Leu Val Ala
1               5                   10

<210> SEQ ID NO 226
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Trp Tyr Arg Gln Ala Ser Gly Lys Glu Arg Glu Ser Val Ala
1               5                   10
```

<210> SEQ ID NO 227
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Trp Tyr Arg Gln Ala Ser Gly Lys Glu Arg Glu Ser Val Ala
1               5                   10

<210> SEQ ID NO 228
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Trp Val Arg Gln Ala Pro Gly Lys Gly Leu Glu Trp Val Ser
1               5                   10

<210> SEQ ID NO 229
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Trp Tyr Arg Gln Ala Pro Gly Lys Glu Arg Glu Met Val Ala
1               5                   10

<210> SEQ ID NO 230
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Trp Phe Arg Gln Ala Pro Gly Lys Gln Arg Glu Trp Val Ala
1               5                   10

<210> SEQ ID NO 231
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Trp Tyr Arg Gln Ala Gln Gly Lys Gln Arg Glu Pro Val Ala
1               5                   10

<210> SEQ ID NO 232
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 232

Trp Phe Arg Gln Ala Pro Gly Lys Glu Arg Gln Phe Val Ala
1               5                   10

<210> SEQ ID NO 233
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Trp His Arg Gln Ala Pro Gly Lys Gln Arg Glu Pro Val Ala
1               5                   10

<210> SEQ ID NO 234
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Trp Tyr Arg Arg Ala Pro Gly Gln Val Arg Glu Met Val Ala
1               5                   10

<210> SEQ ID NO 235
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Trp Tyr Arg Gln Ala Pro Gly Thr Glu Arg Asp Leu Val Ala
1               5                   10

<210> SEQ ID NO 236
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Trp Tyr Arg Gln Ala Pro Gly Ala Gln Arg Glu Leu Leu Ala
1               5                   10

<210> SEQ ID NO 237
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Trp Tyr Arg Gln Ala Pro Gly Lys Gln Arg Glu Leu Val Ala
1               5                   10

<210> SEQ ID NO 238
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Trp Tyr Arg Gln Ala Pro Gly Lys Glu Arg Glu Leu Val Ala
1               5                   10

<210> SEQ ID NO 239
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Trp Tyr Arg Gln Ala Pro Gly Lys Gln Arg Glu Leu Val Ala
1               5                   10

<210> SEQ ID NO 240
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Trp Tyr Arg Gln Ala Pro Gly Asn Gln Arg Glu Leu Val Ala
1               5                   10

<210> SEQ ID NO 241
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Trp Tyr Arg Gln Ala Pro Gly Lys Gln Arg Glu Pro Val Ala
1               5                   10

<210> SEQ ID NO 242
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Trp Phe Arg Gln Ala Pro Gly Glu Glu Arg Glu Leu Val Ala
1               5                   10

<210> SEQ ID NO 243
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Trp Tyr Arg Gln Ala Pro Gly Asn Gln Arg Glu Pro Val Ala
```

<210> SEQ ID NO 244
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Trp Tyr Arg Gln Ala Pro Gly Thr Glu Arg Asp Leu Val Ala
1               5                   10

<210> SEQ ID NO 245
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Trp His Arg Gln Ala Pro Gly Asn Glu Arg Glu Leu Val Ala
1               5                   10

<210> SEQ ID NO 246
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Trp Tyr Arg Gln Ala Pro Gly Lys Glu Arg Glu Leu Val Ala
1               5                   10

<210> SEQ ID NO 247
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Trp Tyr Arg Gln Ala Pro Gly Lys Gln Arg Glu Leu Val Ala
1               5                   10

<210> SEQ ID NO 248
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Trp Val Arg Gln Ala Pro Gly Lys Gly Leu Glu Trp Val Ser
1               5                   10

<210> SEQ ID NO 249
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 249

Trp Tyr Arg Gln Ala Pro Gly Lys Glu Arg Glu Leu Val Ala
1               5                   10

<210> SEQ ID NO 250
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Trp Tyr Arg Gln Ala Pro Gly Lys Glu Arg Glu Leu Val Ala
1               5                   10

<210> SEQ ID NO 251
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Trp Val Arg Gln Ala Pro Gly Lys Gly Leu Glu Trp Val Ser
1               5                   10

<210> SEQ ID NO 252
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Trp Tyr Arg Gln Ala Pro Gly Thr Glu Arg Asp Leu Val Ala
1               5                   10

<210> SEQ ID NO 253
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Trp Tyr Arg Gln Ala Pro Gly Lys Glu Arg Glu Leu Val Ala
1               5                   10

<210> SEQ ID NO 254
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Trp Val Arg Gln Ala Pro Gly Lys Gly Leu Glu Trp Val Ser
1               5                   10

<210> SEQ ID NO 255

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Trp His Arg Gln Ala Pro Gly Asn Glu Arg Glu Leu Val Ala
1               5                   10

<210> SEQ ID NO 256
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Trp His Arg Gln Ala Pro Gly Lys Glu Arg Glu Leu Val Ala
1               5                   10

<210> SEQ ID NO 257
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Trp Val Arg Gln Ala Pro Gly Lys Gly Leu Glu Trp Val Ser
1               5                   10

<210> SEQ ID NO 258
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Ile Ser Trp Asp Ile Ala Glu Asn Thr Val Tyr Leu Gln Met Asn Ser
1               5                   10                  15

Leu Asn Ser Glu Asp Thr Thr Val Tyr Tyr Cys Asn Ser
            20                  25

<210> SEQ ID NO 259
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Ile Ser Gly Asp Asn Val Arg Asn Met Val Tyr Leu Gln Met Asn Ser
1               5                   10                  15

Leu Lys Pro Glu Asp Thr Ala Ile Tyr Tyr Cys Ser Ala
            20                  25

<210> SEQ ID NO 260
<211> LENGTH: 29
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 260

Ile Ser Gly Glu Asn Gly Lys Asn Thr Val Tyr Leu Gln Met Asn Ser
1               5                   10                  15

Leu Lys Leu Glu Asp Thr Ala Val Tyr Tyr Cys Leu Gly
            20                  25

<210> SEQ ID NO 261
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Ile Ser Arg Asp Asn Ala Asn Asn Ala Ile Tyr Leu Glu Met Asn Ser
1               5                   10                  15

Leu Lys Pro Glu Asp Thr Ala Val Tyr Val Cys Asn Ala
            20                  25

<210> SEQ ID NO 262
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Ile Ser Arg Asp Asn Ala Glu Asn Thr Val Ser Leu Gln Met Asn Thr
1               5                   10                  15

Leu Lys Pro Glu Asp Thr Ala Val Tyr Phe Cys Asn Ala
            20                  25

<210> SEQ ID NO 263
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Ile Ser Lys Asp Ser Thr Arg Asn Thr Val Tyr Leu Gln Met Asn Met
1               5                   10                  15

Leu Arg Pro Glu Asp Thr Ala Val Tyr Tyr Cys Asn Ala
            20                  25

<210> SEQ ID NO 264
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Ile Ser Arg Asp Asn Ala Lys Asn Thr Val Tyr Leu Gln Met Asn Ser
1               5                   10                  15

Leu Lys Pro Glu Asp Thr Ala Val Tyr Tyr Cys Asn Ala
            20                  25
```

<210> SEQ ID NO 265
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Ile Ser Arg Asp Ile Asp Lys Lys Thr Val Tyr Leu Gln Met Asp Asn
1               5                   10                  15

Leu Lys Pro Glu Asp Thr Gly Val Tyr Tyr Cys Asn Ser
            20                  25

<210> SEQ ID NO 266
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Ile Ser Arg Asp Ile Tyr Lys Lys Thr Val Tyr Leu Gln Met Asp Asn
1               5                   10                  15

Leu Lys Pro Glu Asp Thr Gly Val Tyr Tyr Cys Asn Ser
            20                  25

<210> SEQ ID NO 267
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Ile Ser Arg Asp Asn Ala Lys Thr Thr Leu Tyr Leu Gln Met Asn Ser
1               5                   10                  15

Leu Arg Pro Glu Asp Thr Ala Val Tyr Tyr Cys Thr Ile
            20                  25

<210> SEQ ID NO 268
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Ile Ser Lys Glu Asn Ala Lys Asn Thr Val Tyr Leu Gln Met Asn Ser
1               5                   10                  15

Leu Lys Pro Glu Asp Thr Ala Val Tyr Tyr Cys His Ile
            20                  25

<210> SEQ ID NO 269
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Ile Ser Arg Asp Asn Ala Lys Ser Thr Val Tyr Leu Gln Met Asn Ser
1               5                   10                  15

Leu Lys Pro Glu Asp Thr Ala Ile Tyr Tyr Cys Lys Ala
            20                  25

<210> SEQ ID NO 270
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Ile Ser Arg Asp Asn Ala Lys Asn Thr Val Tyr Leu Gln Met Asn Ser
1               5                   10                  15

Leu Lys Pro Glu Asp Thr Ala Ile Tyr Thr Cys His Val
            20                  25

<210> SEQ ID NO 271
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Ile Ser Arg Asp Asn Ala Ala Asn Thr Phe Tyr Leu Gln Met Asn Asn
1               5                   10                  15

Leu Arg Pro Asp Asp Thr Ala Val Tyr Tyr Cys Asn Val
            20                  25

<210> SEQ ID NO 272
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Val Ser Arg Asp Ile Val Lys Asn Thr Met Tyr Leu Gln Met Asn Ser
1               5                   10                  15

Leu Lys Pro Glu Asp Thr Ala Val Tyr Tyr Cys Ser Tyr
            20                  25

<210> SEQ ID NO 273
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Ile Ser Arg Asp Asn Thr Gln Asn Leu Val Tyr Leu Gln Met Asn Asn
1               5                   10                  15

Leu Gln Pro His Asp Thr Ala Ile Tyr Tyr Cys Gly Ala
            20                  25

<210> SEQ ID NO 274
<211> LENGTH: 29
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 274

Ile Ser Arg Asp Asn Ala Lys Asn Thr Leu Tyr Leu Gln Met Asn Asn
1               5                   10                  15

Leu Lys Pro Glu Asp Thr Ala Val Tyr Tyr Cys Asn Ala
            20                  25

<210> SEQ ID NO 275
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Ile Ser Arg Asp Asn Ala Lys Asn Thr Val Tyr Leu Gln Met Asn Arg
1               5                   10                  15

Leu Thr Pro Glu Asp Thr Asp Val Tyr Tyr Cys Arg Phe
            20                  25

<210> SEQ ID NO 276
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Ile Ser Arg Asp Asn Ala Lys Asn Thr Val Tyr Leu Gln Met Glu Ser
1               5                   10                  15

Leu Val Ala Glu Asp Thr Ala Val Tyr Tyr Cys Asn Ala
            20                  25

<210> SEQ ID NO 277
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Val Ser Arg Asp Ser Ala Lys Asn Ile Val Tyr Leu Gln Met Asn Ser
1               5                   10                  15

Leu Thr Pro Glu Asp Thr Ala Val Tyr Tyr Cys Asn Thr
            20                  25

<210> SEQ ID NO 278
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Ile Ser Arg Asp Asn Ala Lys Asn Thr Val Tyr Leu Gln Met Asn Ser
1               5                   10                  15

Leu Lys Pro Glu Asp Thr Ala Val Tyr Tyr Cys Asn Ala

```
            20                  25

<210> SEQ ID NO 279
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Ile Ser Arg Asp Asn Ala Lys Asn Thr Val Tyr Leu Gln Met Asn Ser
1               5                   10                  15

Leu Lys Pro Glu Asp Thr Ala Val Tyr Tyr Cys Asn Thr
            20                  25

<210> SEQ ID NO 280
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Ile Ser Arg Asp Asn Ala Lys Asn Thr Val Tyr Leu Gln Met Asn Ser
1               5                   10                  15

Leu Lys Pro Glu Asp Thr Ala Ile Tyr Thr Cys His Val
            20                  25

<210> SEQ ID NO 281
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Val Ser Arg Asp Ser Ala Lys Asn Ile Val Tyr Leu Gln Met Asn Arg
1               5                   10                  15

Leu Lys Pro Glu Asp Thr Ala Val Tyr Tyr Cys Asn Thr
            20                  25

<210> SEQ ID NO 282
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Ile Ser Arg Asp Asn Ala Arg Asn Thr Val Tyr Leu Gln Met Asp Ser
1               5                   10                  15

Leu Lys Pro Glu Asp Thr Ala Ile Tyr Thr Cys His Val
            20                  25

<210> SEQ ID NO 283
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 283

Ile Ser Arg Asp Asn Ala Lys Asn Thr Leu Tyr Leu Gln Met Asn Asn
1               5                   10                  15

Leu Lys Pro Glu Asp Thr Ala Val Tyr Tyr Cys Asn Ala
            20                  25

<210> SEQ ID NO 284
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Ile Ser Arg Asp Asn Ala Lys Asn Thr Ala Tyr Leu Gln Met Asn Ser
1               5                   10                  15

Leu Lys Pro Glu Asp Thr Ala Val Tyr Tyr Cys Ser Val
            20                  25

<210> SEQ ID NO 285
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Val Ser Arg Asp Ser Ala Lys Asn Ile Val Tyr Leu Gln Met Asn Ser
1               5                   10                  15

Leu Lys Pro Glu Asp Thr Ala Val Tyr Tyr Cys Asn Thr
            20                  25

<210> SEQ ID NO 286
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Ile Ser Arg Asp Asn Ser Lys Asn Thr Leu Tyr Leu Gln Met Asn Ser
1               5                   10                  15

Leu Arg Ala Glu Asp Thr Ala Val Tyr Tyr Cys Ala Val
            20                  25

<210> SEQ ID NO 287
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Ile Ser Arg Asp Asn Ser Lys Asn Thr Leu Tyr Leu Gln Met Asn Ser
1               5                   10                  15

Leu Arg Ala Glu Asp Thr Ala Val Tyr Tyr Cys Ala Val
            20                  25

<210> SEQ ID NO 288
<211> LENGTH: 29
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Ile Ser Arg Asp Asn Ser Lys Asn Thr Leu Tyr Leu Gln Met Asn Ser
1               5                   10                  15
Leu Arg Ala Glu Asp Thr Ala Val Tyr Tyr Cys Asn Thr
            20                  25

<210> SEQ ID NO 289
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Ile Ser Arg Asp Asn Ser Lys Asn Thr Leu Tyr Leu Gln Met Asn Ser
1               5                   10                  15
Leu Arg Ala Glu Asp Thr Ala Val Tyr Tyr Cys Asn Thr
            20                  25

<210> SEQ ID NO 290
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Ile Ser Arg Asp Asn Ser Lys Asn Thr Leu Tyr Leu Gln Met Asn Ser
1               5                   10                  15
Leu Arg Ala Glu Asp Thr Ala Val Tyr Tyr Cys Asn Thr
            20                  25

<210> SEQ ID NO 291
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Ile Ser Arg Asp Asn Ser Lys Asn Thr Leu Tyr Leu Gln Met Asn Ser
1               5                   10                  15
Leu Arg Ala Glu Asp Thr Ala Val Tyr Tyr Cys Asn Ala
            20                  25

<210> SEQ ID NO 292
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Ile Ser Arg Asp Asn Ser Lys Asn Thr Leu Tyr Leu Gln Met Asn Ser
1               5                   10                  15
```

Leu Arg Ala Glu Asp Thr Ala Val Tyr Tyr Cys Asn Ala
            20                  25

<210> SEQ ID NO 293
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Ile Ser Arg Asp Asn Ser Lys Asn Thr Leu Tyr Leu Gln Met Asn Ser
1               5                   10                  15

Leu Arg Ala Glu Asp Thr Ala Val Tyr Tyr Cys Asn Ala
            20                  25

<210> SEQ ID NO 294
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Ile Ser Arg Asp Asn Ser Lys Asn Thr Leu Tyr Leu Gln Met Asn Ser
1               5                   10                  15

Leu Arg Ala Glu Asp Thr Ala Val Tyr Tyr Cys Ser Val
            20                  25

<210> SEQ ID NO 295
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Ile Ser Arg Asp Asn Ser Lys Asn Thr Leu Tyr Leu Gln Met Asn Ser
1               5                   10                  15

Leu Arg Ala Glu Asp Thr Ala Val Tyr Tyr Cys Ser Val
            20                  25

<210> SEQ ID NO 296
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Ile Ser Arg Asp Asn Ser Lys Asn Thr Leu Tyr Leu Gln Met Asn Ser
1               5                   10                  15

Leu Arg Ala Glu Asp Thr Ala Val Tyr Tyr Cys Ser Val
            20                  25

<210> SEQ ID NO 297
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 297

Trp Gly Gln Gly Thr Gln Val Thr Val Ser Ser
1               5                   10

<210> SEQ ID NO 298
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Trp Gly Lys Gly Thr Leu Val Thr Val Ser Ser
1               5                   10

<210> SEQ ID NO 299
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Trp Gly Gln Gly Thr Gln Val Thr Val Ser Ser
1               5                   10

<210> SEQ ID NO 300
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Phe Gly Gln Gly Thr Gln Val Thr Val Ser Ser
1               5                   10

<210> SEQ ID NO 301
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Trp Gly Gln Gly Thr Gln Val Thr Val Ser Ser
1               5                   10

<210> SEQ ID NO 302
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Trp Gly Gln Gly Thr Gln Val Thr Val Ser Ser
1               5                   10

<210> SEQ ID NO 303
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 303

Trp Gly Gln Gly Thr Gln Val Thr Val Ser Ser
1               5                   10

<210> SEQ ID NO 304
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Trp Gly Gln Gly Thr Gln Val Thr Val Ser Ser
1               5                   10

<210> SEQ ID NO 305
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Trp Gly Gln Gly Thr Gln Val Thr Val Ser Ser
1               5                   10

<210> SEQ ID NO 306
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Gln Gly Thr Leu Val Thr Val Ser Ser
1               5

<210> SEQ ID NO 307
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Trp Gly Gln Gly Thr Gln Val Thr Val Ser Ser
1               5                   10

<210> SEQ ID NO 308
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Trp Gly Gln Gly Thr Gln Val Thr Val Ser Ser
1               5                   10
```

```
<210> SEQ ID NO 309
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Trp Gly Gln Gly Thr Gln Val Thr Val Ser Ser
1               5                   10

<210> SEQ ID NO 310
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Trp Gly Gln Gly Thr Gln Val Thr Val Ser Ser
1               5                   10

<210> SEQ ID NO 311
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Trp Gly Gln Gly Thr Gln Val Thr Val Ser Ser
1               5                   10

<210> SEQ ID NO 312
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Trp Gly Gln Gly Thr Gln Val Thr Val Ser Ser
1               5                   10

<210> SEQ ID NO 313
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Trp Gly Gln Gly Thr Gln Val Thr Val Ser Ser
1               5                   10

<210> SEQ ID NO 314
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 314

Trp Gly Gln Gly Thr Gln Val Thr Val Ser Ser
1               5                   10

<210> SEQ ID NO 315
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Trp Gly Gln Gly Thr Gln Val Thr Val Ser Ser
1               5                   10

<210> SEQ ID NO 316
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Trp Gly Gln Gly Thr Gln Val Thr Val Ser Ser
1               5                   10

<210> SEQ ID NO 317
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Trp Gly Gln Gly Thr Gln Val Thr Val Ser Ser
1               5                   10

<210> SEQ ID NO 318
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Trp Gly Gln Gly Thr Gln Val Thr Val Ser Ser
1               5                   10

<210> SEQ ID NO 319
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Trp Gly Gln Gly Thr Gln Val Thr Val Ser Ser
1               5                   10

<210> SEQ ID NO 320
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 320

Trp Gly Gln Gly Thr Gln Val Thr Val Ser Ser
1               5                   10

<210> SEQ ID NO 321
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Trp Gly Gln Gly Thr Gln Val Thr Val Ser Ser
1               5                   10

<210> SEQ ID NO 322
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Trp Gly Gln Gly Thr Gln Val Thr Val Ser Ser
1               5                   10

<210> SEQ ID NO 323
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Trp Gly Gln Gly Thr Gln Val Thr Val Ser Ser
1               5                   10

<210> SEQ ID NO 324
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Trp Gly Gln Gly Thr Gln Val Thr Val Ser Ser
1               5                   10

<210> SEQ ID NO 325
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Trp Gly Gln Gly Thr Leu Val Thr Val Ser Ser
1               5                   10
```

```
<210> SEQ ID NO 326
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Trp Gly Gln Gly Thr Leu Val Thr Val Ser Ser
1               5                   10

<210> SEQ ID NO 327
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Trp Gly Gln Gly Thr Leu Val Thr Val Ser Ser
1               5                   10

<210> SEQ ID NO 328
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Trp Gly Gln Gly Thr Leu Val Thr Val Ser Ser
1               5                   10

<210> SEQ ID NO 329
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Trp Gly Gln Gly Thr Leu Val Thr Val Ser Ser
1               5                   10

<210> SEQ ID NO 330
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Trp Gly Gln Gly Thr Leu Val Thr Val Ser Ser Gly Gly
1               5                   10

<210> SEQ ID NO 331
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 331

Trp Gly Gln Gly Thr Leu Val Thr Val Ser Ser Gly Gly
1               5                   10

<210> SEQ ID NO 332
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Trp Gly Gln Gly Thr Leu Val Thr Val Ser Ser Gly Gly
1               5                   10

<210> SEQ ID NO 333
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Trp Gly Gln Gly Thr Leu Val Thr Val Ser
1               5                   10

<210> SEQ ID NO 334
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Trp Gly Gln Gly Thr Leu Val Thr Val Ser Ser
1               5                   10

<210> SEQ ID NO 335
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Trp Gly Gln Gly Thr Leu Val Thr Val Ser Ser
1               5                   10

<210> SEQ ID NO 336
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 336

His His His His His His
1               5
```